(12) United States Patent
Basser et al.

(10) Patent No.: US 11,835,611 B2
(45) Date of Patent: Dec. 5, 2023

(54) ISOTROPIC GENERALIZED DIFFUSION TENSOR MRI

(71) Applicant: The United States of America, as represented by the Secretary, Department of Health and Human Services, Bethesda, MD (US)

(72) Inventors: Peter J. Basser, Washington, DC (US); Alexandru V. Avram, Gaithersburg, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 620 days.

(21) Appl. No.: 16/603,205

(22) PCT Filed: Apr. 6, 2018

(86) PCT No.: PCT/US2018/026584
§ 371 (c)(1),
(2) Date: Oct. 4, 2019

(87) PCT Pub. No.: WO2018/187764
PCT Pub. Date: Oct. 11, 2018

(65) Prior Publication Data
US 2020/0379072 A1  Dec. 3, 2020

Related U.S. Application Data

(60) Provisional application No. 62/482,637, filed on Apr. 6, 2017.

(51) Int. Cl.
*G01V 3/00* (2006.01)
*G01R 33/563* (2006.01)
(Continued)

(52) U.S. Cl.
CPC ........ *G01R 33/56341* (2013.01); *A61B 5/004* (2013.01); *A61B 5/0042* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 5,853,365 A * 12/1998 Yamagata ........ G01R 33/56308
324/309
2012/0209741 A1* 8/2012 Bonner .................... H04W 4/20
705/26.3

(Continued)

FOREIGN PATENT DOCUMENTS

CN     102736046 A  * 10/2012  ....... G01R 33/56341
CN     103142229 B  * 12/2015
(Continued)

OTHER PUBLICATIONS

Tomotsugu, Inspecting Method and Inspecting System Using Nuclear Magnetic Resonance, Dec. 5, 1995 (Year: 1995).*
(Continued)

*Primary Examiner* — Walter L Lindsay, Jr.
*Assistant Examiner* — Frederick Wenderoth
(74) *Attorney, Agent, or Firm* — Leydig, Voit & Mayer, Ltd.

(57) ABSTRACT

Isotropic generalized diffusion tensor imaging methods and apparatus are configured to obtain signal attenuations using selected sets of applied magnetic field gradient directions whose averages produce mean apparent diffusion constants (mADCs) over a wide range of b-values, associated with higher order diffusion tensors (HOT). These sets are selected based on analytical descriptions of isotropic HOTs and the
(Continued)

associated averaged signal attenuations are combined to produce mADCs, or probability density functions of intra-voxel mADC distributions. Estimates of biologically-specific rotation-invariant parameters for quantifying tissue water mobilities or other tissue characteristics can be obtained such as Traces of HOTs associated with diffusion and mean t-kurtosis.

29 Claims, 27 Drawing Sheets

(51) Int. Cl.
| | |
|---|---|
| *A61B 5/00* | (2006.01) |
| *A61B 5/055* | (2006.01) |
| *G01R 33/385* | (2006.01) |
| *G01R 33/56* | (2006.01) |
| *G01R 33/565* | (2006.01) |
| *A61B 5/20* | (2006.01) |

(52) U.S. Cl.
CPC ............ *A61B 5/0044* (2013.01); *A61B 5/055* (2013.01); *G01R 33/385* (2013.01); *G01R 33/5608* (2013.01); *G01R 33/56509* (2013.01); *A61B 5/20* (2013.01); *A61B 5/4029* (2013.01); *A61B 5/416* (2013.01); *A61B 5/4244* (2013.01); *A61B 5/4255* (2013.01); *A61B 5/4343* (2013.01); *A61B 5/4381* (2013.01); *A61B 5/4519* (2013.01)

(58) Field of Classification Search
USPC ......................................................... 324/309
See application file for complete search history.

(56) References Cited

U.S. PATENT DOCUMENTS

2016/0343129 A1\* 11/2016 Novikov ................. G06V 10/42
2016/0356873 A1\* 12/2016 Topgaard ............... A61B 5/055

FOREIGN PATENT DOCUMENTS

| CN | 105980876 A | \* | 9/2016 | ............. A61B 5/055 |
| GB | 2270763 A | \* | 3/1994 | ......... G01R 33/5615 |
| JP | 2016054994 A | \* | 4/2016 | |
| WO | WO-9504940 A1 | \* | 2/1995 | ....... G01R 33/56341 |

OTHER PUBLICATIONS

Avram et al., "Efficient Experimental Designs for Isotropic Generalized Diffusion Tensor MRI (IGDTI)," *Magnetic Resonance in Medicine*, 79:180-194 (published online May 7, 2017).

Avram et al., "Isotropic Diffusion Relaxometry Imaging (IDRI)," ISMRM 25$^{th}$ Annual Meeting & Exhibition Apr. 22-27, 2017, 3 pages (Nov. 14, 2016).

Avram et al., "Isotropic Diffusion Weighted Mri (IDWI)—a novel, efficient clinical method for quantifying orientationally-averaged features of water diffusion in tissues," ISMRM 25$^{th}$ Annual Meeting & Exhibition Apr. 22-27, 2017, 4 pages (Nov. 14, 2016).

Dhital et al., "Isotropic Diffusion Weighting Provides Insight on Diffusion Compartments in Human Brain White Matter In vivo," Proceedings of the International Society for Magnetic Resonance in Medicine, 23$^{rd}$ Annual Meeting and Exhibition May 30-Jun. 5, 2015, 23:2788 (May 15, 2015).

International Search Report and Written Opinion from International Application No. PCT/US2018/026584, dated Jul. 23, 2018, 21 pages.

Jones, "The Effect of Gradient Sampling Schemes on Measures Derived from Diffusion Tensor MRI: A Monte Carlo Study," *Magnetic Resonance in Medicine*, 51:807-815 (Mar. 26, 2004).

Liu et al., "Generalized Diffusion Tensor Imaging (GDTI): A Method for Characterizing and Imaging Diffusion Anisotropy Caused by Non-Gaussian Diffusion," *Israel Journal of Chemistry*, 43:145-154 (Nov. 1, 2003).

Ozarslan et al., "Generalized Diffusion Tensor Imaging and Analytical Relationships Between Diffusion Tensor Imaging and High Angular Resolution Diffusion Imaging," *Magnetic Resonance in Medicine*, 50:955-965 (2003).

Pierpaoli et al., "TORTOISE: an integrated software package for processing of diffusion MRI data," *Proc. Intl. Soc. Mag. Reson. Med.*, 18:1597 (Apr. 17, 2010).

\* cited by examiner

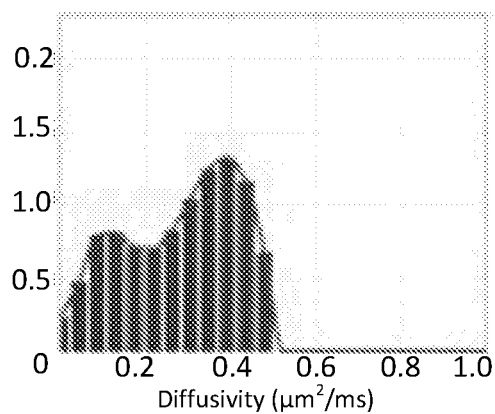
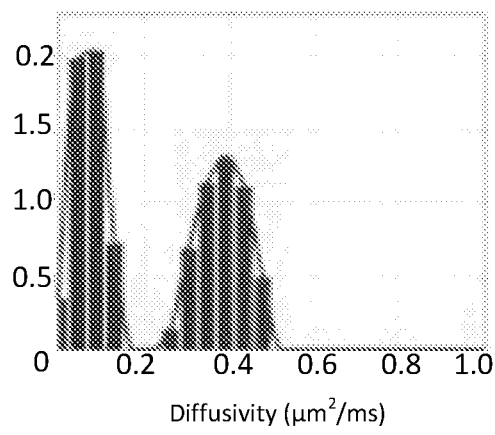
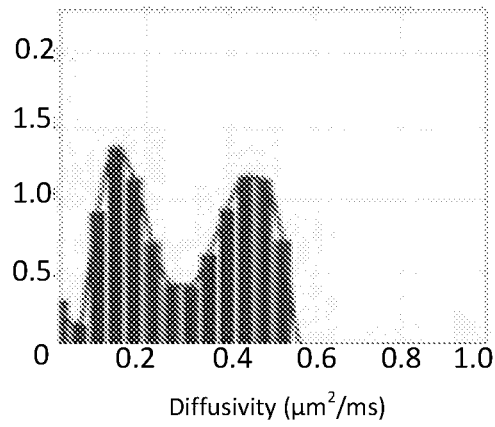
FIG. 14

Diffusivity (μm²/ms)  Diffusivity (μm²/ms)  Diffusivity (μm²/ms)
GRAY MATTER VOXEL  WHITE MATTER VOXEL  CEREBROSPINAL FLUID VOXEL FIG. 17
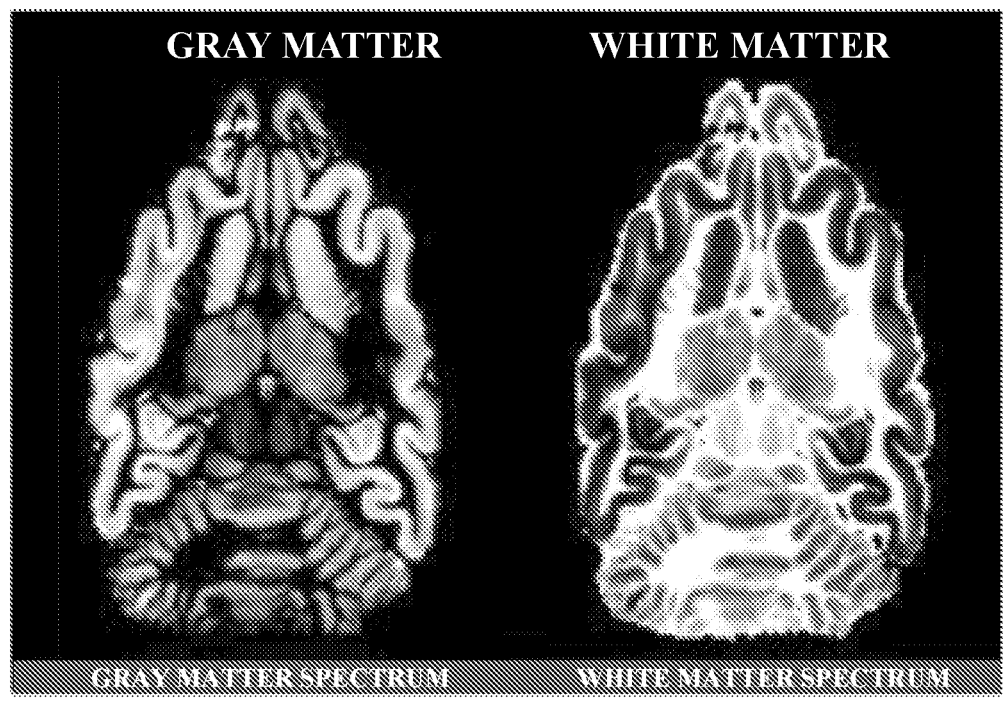
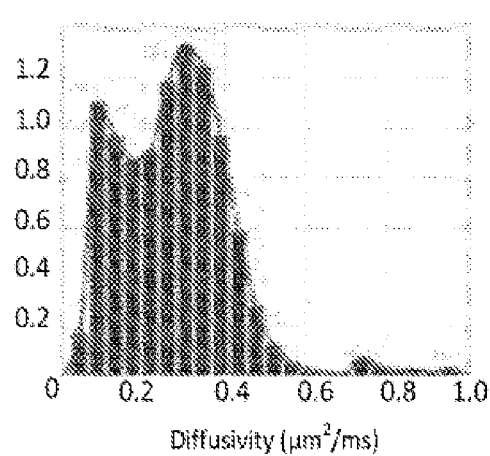
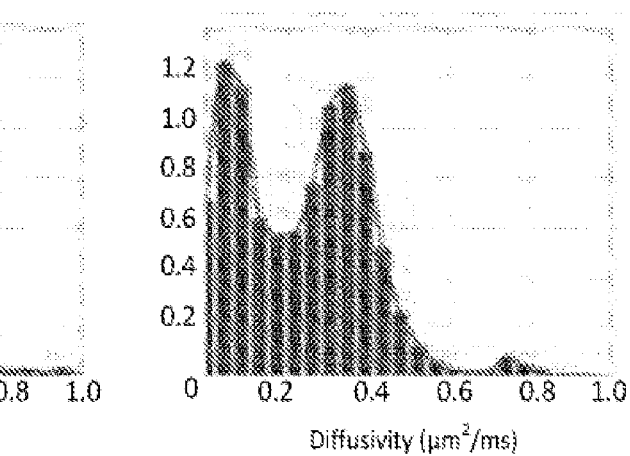
FIG. 18

FIG. 19
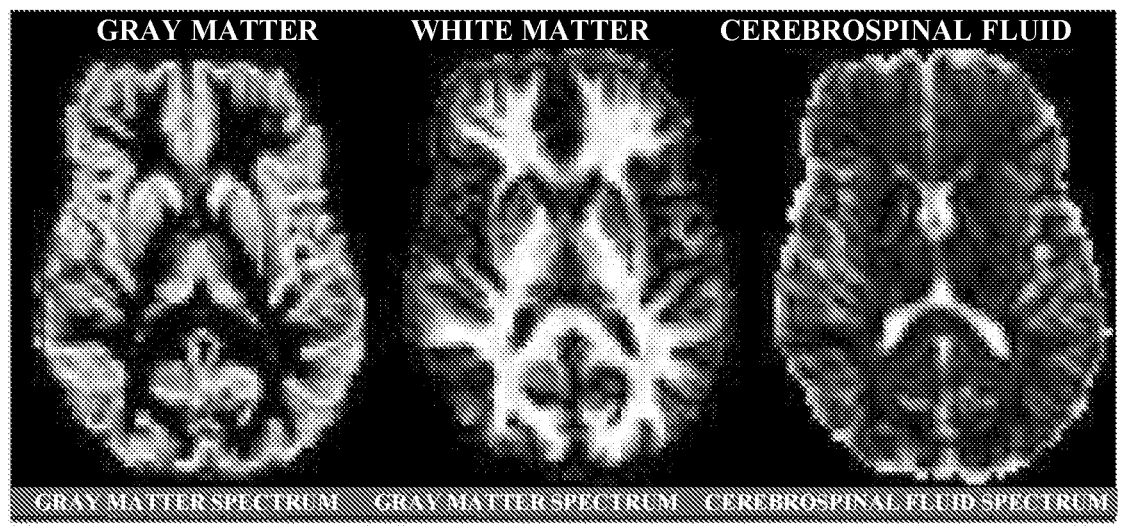
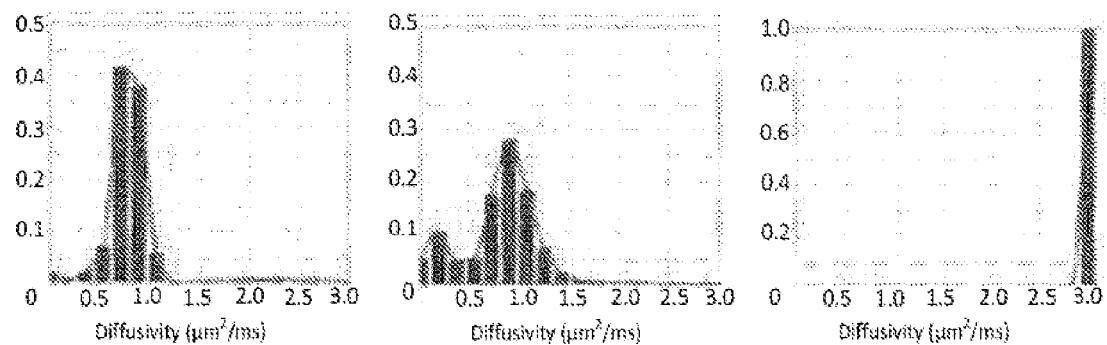
FIG. 20

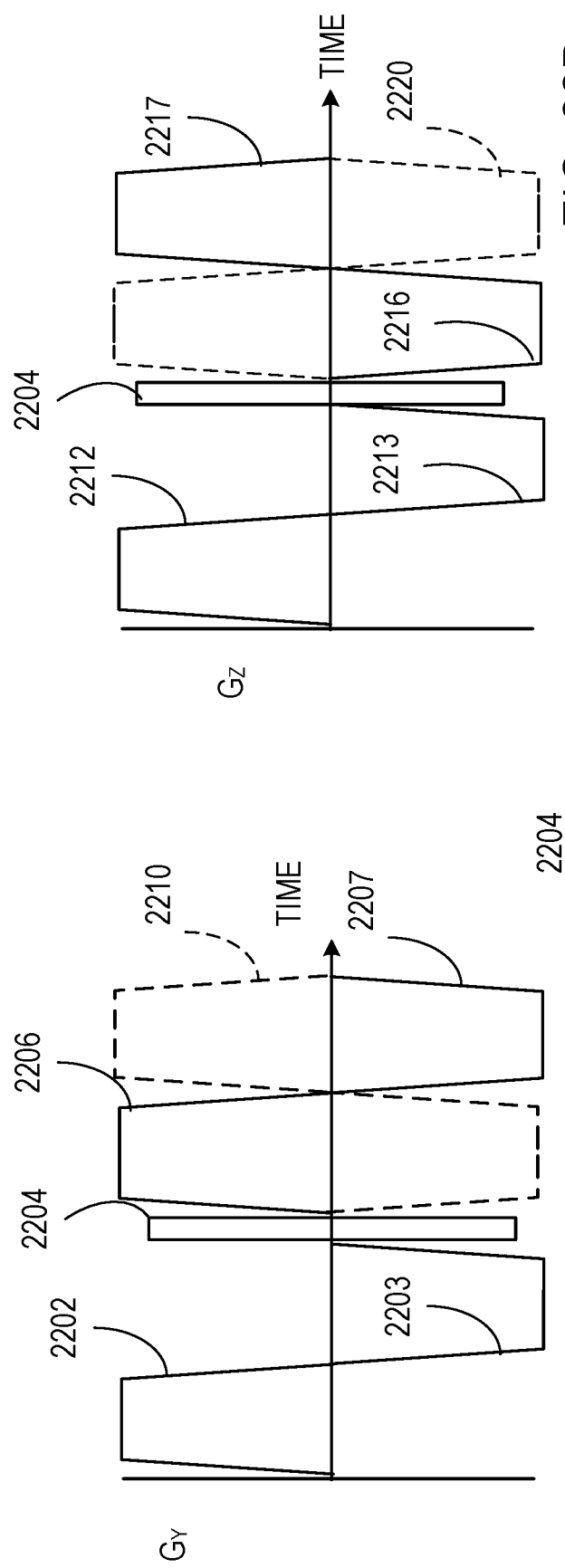
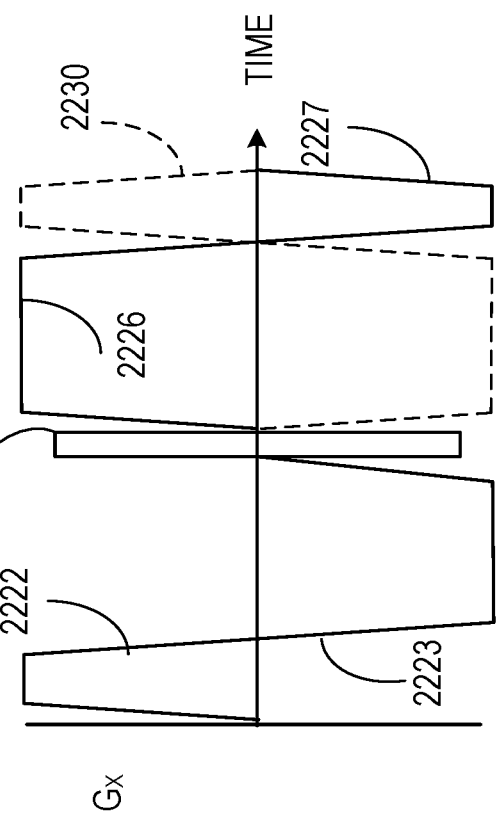
FIG. 22A
FIG. 22B
FIG. 22C

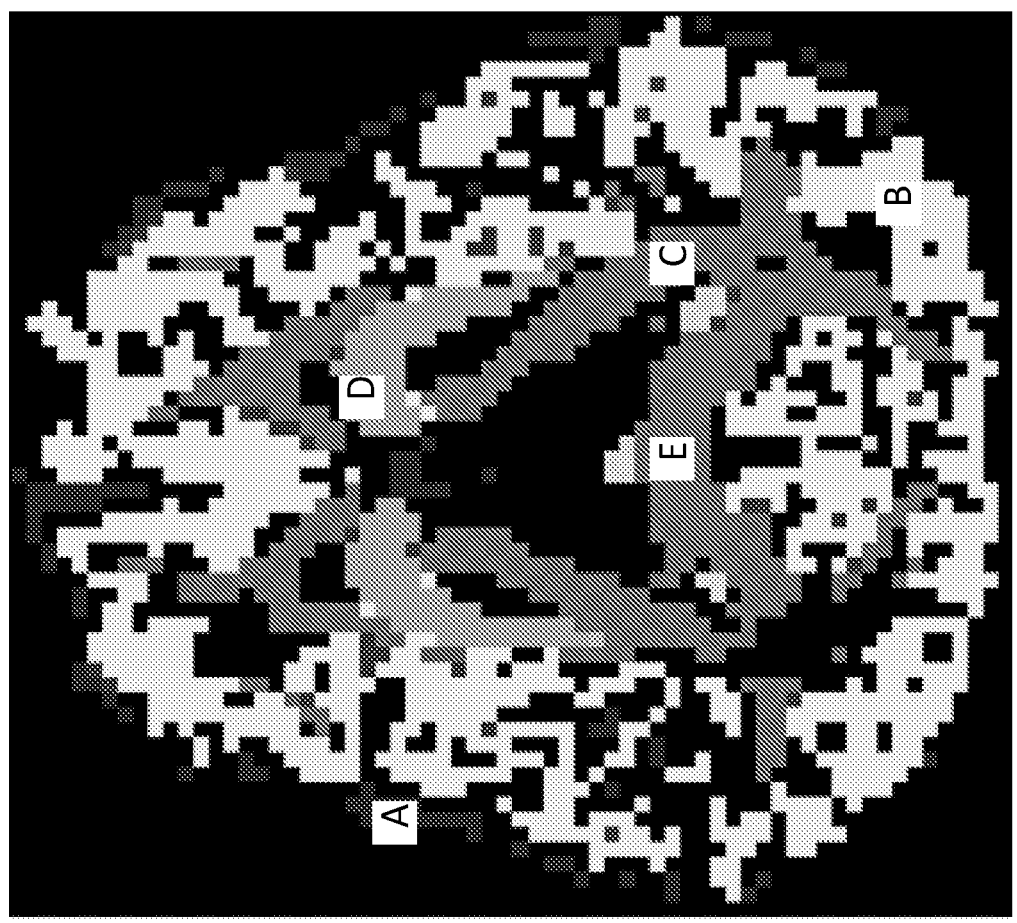
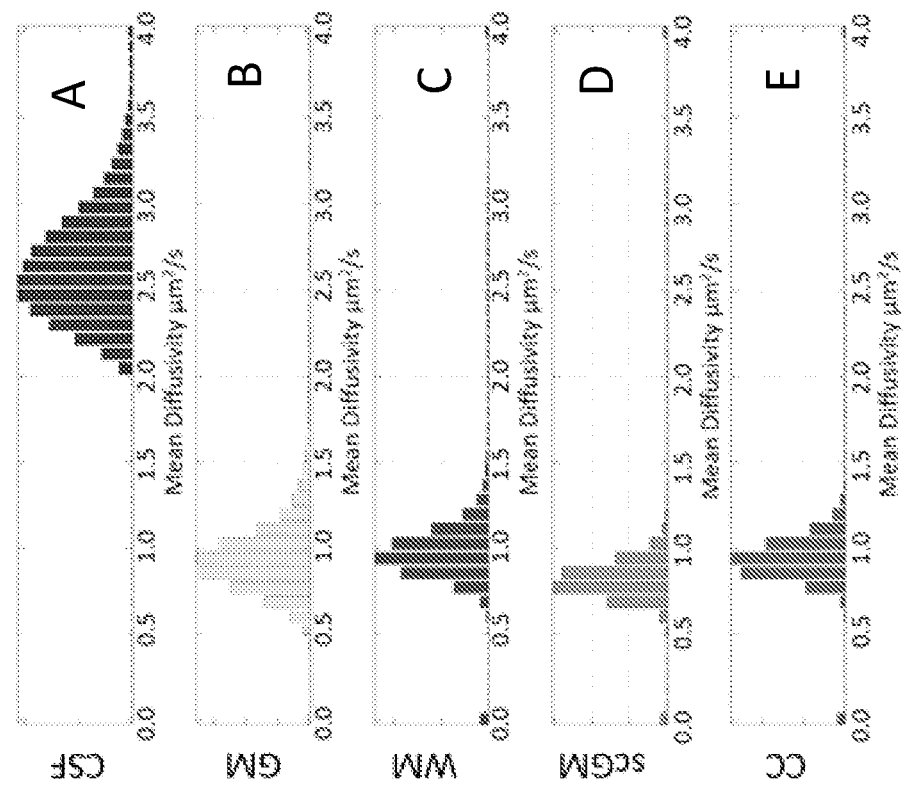
FIG. 27B
FIG. 27A

ISOTROPIC GENERALIZED DIFFUSION TENSOR MRI

CROSS REFERENCE TO RELATED APPLICATIONS

This application is the U.S. National Stage of International Application No. PCT/US2018/026584, filed Apr. 6, 2018, which was published in English under PCT Article 21(2), which in turn claims the benefit of U.S. Provisional Application No. 62/482,637, filed Apr. 6, 2017, which is herein incorporated by reference in its entirety.

FIELD OF THE DISCLOSURE

The disclosure pertains to diffusion magnetic resonance imaging.

BACKGROUND

Rotation-invariant parameters, such as the mean apparent diffusion coefficient (mADC), have proven to be sensitive, robust, and reliable quantitative clinical imaging biomarkers for noninvasive detection and characterization of hypoxic ischemic brain injury and other pathologies. For a given diffusion sensitization, b, the mADC quantifies the apparent diffusion coefficient averaged uniformly over all orientations u on the unit sphere:

$$mADC(b) = -\frac{1}{4\pi} \int \frac{1}{b} \ln \frac{S_b(u)}{S_0} d\Omega_u,$$

wherein $S_b(u)$ is the diffusion weighted signal along orientation u, $S_0$ is the non-diffusion weighted (baseline) signal, and $d\Omega_u$ is the solid angle in the direction of u. For small b-values (i.e., in the Gaussian diffusion regime), the mADC equals one-third the Trace of the $2^{nd}$-order diffusion tensor, and can be measured from several diffusion weighted images (DWIs) using multiple methods, typically by taking the geometric mean of multiple DWIs acquired with the diffusion gradient orientations uniformly sampling the unit sphere. As a rotation-invariant structural parameter immune to diffusion anisotropy, the mADC provides a robust and eloquent biomarker of tremendous clinical value for detecting and characterizing tissue changes such as those occurring in stroke and cancer.

Technological advances in radio-frequency (RF) and magnetic field gradient hardware on clinical magnetic resonance imaging (MRI) systems have enabled measurements of mADCs using higher diffusion sensitizations that were previously inaccessible. Clinical studies have shown that the mADC measured at higher b-values improves conspicuity and discrimination in prostate tumors, breast lesions, and cerebral gliomas, and provides a better marker for cell viability.

Nevertheless, the ability of the Trace of the $2^{nd}$-order diffusion tensor to quantify orientationally-averaged bulk properties of tissue water in the brain is limited to low diffusion sensitizations (up to b-values ~1000 s/mm$^2$) for which the Gaussian approximation of the signal phase distribution underlying diffusion tensor imaging (DTI) is valid. At higher b-values, signal modulations due to diffusion anisotropy become more prominent, especially in regions with complex microstructure (such as crossing white matter fiber pathways), potentially leading to confounds in the interpretation of clinical findings. mADC-weighted signals with higher diffusion sensitization can be obtained by averaging a large number of DWIs acquired with multiple orientations uniformly sampled over the unit sphere. Alternatively, one could analytically approximate the diffusion signal equation using a cumulant expansion and measure the higher order diffusion tensors (HOTs) using an extension of DTI called generalized diffusion tensor imaging (GDTI). Both approaches for measuring orientation-averaged diffusion properties at high b-values require long scan durations to accommodate the acquisition of a large number of DWI data sets with dense orientational sampling schemes, rendering these experimental designs impractical for clinical use.

A more efficient gradient sampling scheme consisting of only 12 DWIs and one baseline non-diffusion weighted (b=0 s/mm$^2$) image has been proposed for estimating the mean kurtosis tensor, i.e., the mean t-kurtosis, $\overline{W}$. This rotation-invariant parameter is analogous to the mean kurtosis (MK) in diffusion kurtosis imaging (DKI), which can be derived from the Traces of the $2^{nd}$- and $4^{th}$-order diffusion tensors. Similar to the mADC in stroke, it has been claimed that microstructural parameters computed from generalized Traces of HOTs, such as the mean t-kurtosis, may provide eloquent (and potentially more biologically specific) clinical markers for many neuropathologies. However, there remains a need for extending the clinical quantitation of rotation-invariant diffusion tissue properties to higher b-values and for designing efficient diffusion-encoding schemes to measure intrinsic HOT-derived microstructural parameters.

SUMMARY OF THE DISCLOSURE

Disclosed herein are approaches referred to as "isotropic generalized diffusion tensor imaging" (IGDTI) that can produce diffusion weightings that are analytically related to the orientational complexity of a bulk diffusion signal as described by higher order tensors (HOTs) and can efficiently remove the effect of angular modulations in the MR signal due to diffusion anisotropy. IGDTI-based methods and apparatus can permit measurements within clinically feasible scan durations of orientationally-averaged DWIs and mADCs over a wide range of b-values, and estimation of various rotation-invariant microstructural parameters, such as HOT-Traces or mean t-kurtosis, as well as estimation of the probability density function (pdf) of orientationally-averaged diffusivities, (i.e., the isotropic diffusivity distribution or spectrum) within each imaging voxel and the signal fractions of various tissue types based on tissue-specific isotropic diffusivity spectra. Thus, the disclosed approaches can provide diffusion MRI methods that estimate biologically-specific rotation-invariant parameters for quantifying tissue water mobilities or other intrinsic tissue characteristics in clinical applications. Typical examples include traces of HOTs, mean t-kurtosis, isotropic diffusivity spectra, and tissue signal fractions.

Magnetic resonance imaging apparatus comprise at least one gradient coil situated to produce a magnetic field gradient in a specimen in a plurality of orientations, the plurality of orientations including (1) three mutually orthogonal directions at low b-values and (2) four directions evenly distributed over 4π steradians at intermediate b-values. At least one signal RF coil is situated to acquire signal attenuations corresponding to each of the gradient orientations. A data acquisition system is coupled to the signal coil, and operable to produce a first signal attenuation average based on the signal attenuations associated with the three mutually orthogonal directions and a second signal attenuation average associated with the four directions evenly distributed over 4π steradians. A display is coupled to the data acquisition system so as to display an image based on one or more of the first signal attenuation average and the second signal attenuation average.

In some examples, the first signal attenuation average and the second signal attenuation average are combined to produce an image associated with a $4^{th}$-order mean apparent diffusion coefficient. In other examples, the first signal attenuation average and the second signal attenuation average are combined to produce a first image associated with a $2^{nd}$-order diffusion tensor trace TR(2) or mean diffusivity D(2) and a second image associated with a $4^{th}$-order diffusion tensor trace Tr(4) or mean diffusivity D(4) In still further examples, the data acquisition system is operable to produce a third signal attenuation average associated with gradient fields applied in six directions corresponding to two mutually orthogonal directions in each of three mutually orthogonal planes at high b-values. In particular examples, the first signal attenuation average and the third signal attenuation average are combined to produce a first image associated with the $2^{nd}$-order diffusion tensor trace TR(2) or mean diffusivity D(2) and a second image associated with the $4^{th}$-order diffusion tensor trace TR(4) or mean diffusivity D(4). According to other examples, the first signal attenuation average, the second signal attenuation average, and the third signal attenuation average are combined to produce an image associated with a $6^{th}$-order diffusion tensor trace TR(6) or mean diffusivity D(6). The sets of gradient directions are selected based on b-values. At low b-values, the mADC is equal to ⅓ of the trace of the 2nd order tensor. At higher b-values, the mADC is computed from orientationally-averaged DWIs and represents a weighted average of traces (or mean diffusivities) of higher order tensors. The 2nd order trace and mean diffusivity are related by the scaling factor of ⅓. 4th order trace and mean diffusivity are related by the scaling factor of ⅕, and the 6th order trace and mean diffusivity are related by the scaling ⅐.

Methods comprise applying gradient magnetic fields to a specimen in at least two sets of selected directions, wherein a first set is three mutually orthogonal directions, a second set is four directions evenly distributed over the unit sphere, and a third set is six directions corresponding to two mutually orthogonal directions in each of three mutually orthogonal planes, so as to acquire respective signal attenuation averages. Based on the signal attenuation averages associated with at least two selected sets, estimating at least one of a $2^{nd}$-order mean apparent diffusion coefficient, a $4^{th}$-order mean apparent diffusion coefficient, and a $6^{th}$-order mean apparent diffusion coefficient. In some examples, based on signal attenuation averages associated with at least two selected sets, the $2^{nd}$-order mean apparent diffusion coefficient, the $4^{th}$-order mean apparent diffusion coefficient, and the $6^{th}$-order mean apparent diffusion coefficient are estimated, and an image associated with at least one of the $2^{nd}$-order, $4^{th}$-order, and $6^{th}$-order mADC is obtained. According to an embodiment, the gradient magnetic fields are applied to the specimen in the three sets of selected directions and signal attenuation averages associated with each of the three sets of selected directions are obtained. Averages of the log signal attenuations or geometric averages of the signals can be used. Based on the signal attenuation averages associated with the three sets of selected directions, at least one of the $2^{nd}$-order mean apparent diffusion coefficient, the $4^{th}$-order mean apparent diffusion coefficient, and the $6^{th}$-order mean apparent diffusion coefficient is estimated. In some embodiments, based on the signal attenuation averages associated with the three sets of selected directions, the $2^{nd}$-order mADC, the $4^{th}$-order mADC, and the $6^{th}$-order mADC are estimated. In one example, the selected sets of directions includes the first set, and the second order mADC is estimated based on the average signal attenuation associated with the first set of directions. In further examples, the selected sets of directions includes the second set, and the $2^{nd}$-order mADC is estimated based on the signal attenuation average associated with the second set of directions. In some examples, a magnitude of a diffusion-sensitizing magnetic field gradient is selected based on an order of an average mean diffusion coefficient to be estimated. In typical examples, the signal attenuation averages are performed voxel by voxel so that an estimate of a selected mADC is a voxel by voxel estimate that defines an associated image, and can be measured and mapped.

A magnetic resonance imaging method for producing images associated with mADCs in a specimen comprises, with respect to a selected three dimensional rectilinear coordinate system, applying gradient fields along each coordinate axis and averaging associated signal attenuations specified by [1,0,0], [0,1,0], [0,0,1] to obtain a signal attenuation average, M3; applying gradient fields along each direction specified by $$\left[\frac{1}{\sqrt{3}}, \frac{1}{\sqrt{3}}, \frac{1}{\sqrt{3}}\right], \left[\frac{-1}{\sqrt{3}}, \frac{1}{\sqrt{3}}, \frac{1}{\sqrt{3}}\right],$$
$$\left[\frac{1}{\sqrt{3}}, \frac{-1}{\sqrt{3}}, \frac{1}{\sqrt{3}}\right], \left[\frac{1}{\sqrt{3}}, \frac{1}{\sqrt{3}}, \frac{-1}{\sqrt{3}}\right]$$

and averaging associated signal attenuations to obtain a signal attenuation average, M4; and applying gradient fields along each direction specified by $$\left[\frac{1}{\sqrt{2}}, \frac{1}{\sqrt{2}}, 0\right], \left[\frac{1}{\sqrt{2}}, \frac{-1}{\sqrt{2}}, 0\right], \left[0, \frac{1}{\sqrt{2}}, \frac{1}{\sqrt{2}}\right],$$
$$\left[0, \frac{1}{\sqrt{2}}, \frac{-1}{\sqrt{2}}\right], \left[\frac{1}{\sqrt{2}}, 0, \frac{1}{\sqrt{2}}\right], \left[\frac{-1}{\sqrt{2}}, 0, \frac{1}{\sqrt{2}}\right]$$

and averaging associated signal attenuations to obtain a signal attenuation average, M6. One or more diffusion images is produced based on at least one of the signal attenuation averages: M3, M4, or M6. In some examples, the one or more diffusion images includes images associated with one or more of a $2^{nd}$-order mADC, a $4^{th}$-order mADC, and a $6^{th}$-order mADC. In representative examples, the one or more diffusion images includes images associated with one or more of a Trace of a $2^{nd}$-order diffusion tensor, a $4^{th}$-order diffusion tensor, and a $6^{th}$-order diffusion tensor.

These sets of gradient directions can be rotated in any way so long as long as the relative orientations within each set are the same. For example, for the 3-direction set, any 3 orthogonal orientations can be used, for the for the 4-direction set, any configuration of 4 directions uniformly sampling the unit sphere can be used.

Methods comprise obtaining isotropic diffusion tensor images (IGDTIs) associated with at least one of a $2^{nd}$-order, $4^{th}$-order or $6^{th}$-order diffusion tensor at a plurality of magnetic field gradient magnitudes. Based on the obtained IGDTIs at the plurality of magnetic field gradient magnitudes, determining at least one distribution of mADCs associated with at least one of a $2^{nd}$-order, $4^{th}$-order or $6^{th}$-order diffusion tensor. In other examples, the IGDTIs are obtained by applying magnetic field gradients in directions associated with at least two sets of directions associated with at least one of the $2^{nd}$-order, $4^{th}$-order or $6^{th}$-order diffusion tensor. Signal attenuations associated with the magnetic field gradients in each of the sets are combined to produce a least a first signal attenuation average and a second single attenuation average and the first and second signal attenuation averages are combined to determine the at least one distribution of mADCs. In typical examples, the at least one distribution of mADCs is associated a $4^{th}$-order or $6^{th}$-order diffusion tensor.

In other examples, single shot methods comprise applying three-dimensional, refocusing balanced magnetic field gradient pulse sequences to a specimen at a plurality of b-values. During each pulse sequence for each b-valued, gradients are applied along three linearly independent (typically orthogonal) axes simultaneously. Signal decays associated with a plurality of voxels of a specimen are obtained in response, and based on the signal decays, mean diffusivity distributions (MDDs) are estimated for each of the plurality of voxels.

The foregoing and other features and advantages will become more apparent from the following detailed description of several embodiments which proceeds with reference to the accompanying figures.

BRIEF DESCRIPTION OF THE FIGURES

FIG. 8A illustrates a direction-encoded color (DEC) map. FIG. 8B illustrates a baseline (non-diffusion weighted) image. FIG. 8C illustrates IGDTI with b=8500 s/mm$^2$ (signal scaled by 25) and FIG. 8D illustrates mADC at b=8500 s/mm$^2$ computed with clinical IGDTI.

FIG. 10 shows mean and standard deviation maps quantified across 200 simulated experiments with SNR=70 and SNR dependence (mean—dark markers, standard deviation—error bars) in representative gray matter (GM) (labelled) and white matter (WM) (unlabeled) voxels.

FIG. 14 illustrates CDF spectra in three representative voxels containing gray matter, white matter, and mixed brain tissue and corresponding to the images of FIG. 13. Peaks at 0.015 and 0.035 µm$^2$/ms are clearly discernible in the white matter spectrum.

FIG. 17 illustrates tissue signal fractions f (top row) for gray and white matter signals, respectively, measured in fixed ferret brain.

FIG. 18 illustrates averaged diffusivity spectra associated with the images of FIG. 17.

FIG. 19 illustrates tissue signal fractions f (top row) for gray matter, white matter, and cerebrospinal fluid, respectively, measured in live human brain.

FIG. 20 illustrates averaged diffusivity spectra associated with the images of FIG. 19.

FIGS. 22A-22C illustrate magnetic field gradient pulse sequences such as illustrated in FIG. 21 in greater detail.

FIG. 27A illustrates normalized tissue-specific MDDs averaged over whole-brain ROIs defined in CSF—A; cGM—B; WM—C; scGM containing mainly the putamen, the globus pallidum, and caudate nucleus—D; and the CC—E.

FIG. 27B illustrates a representative slice showing the ROIs; voxels at tissue interfaces were excluded from the ROIs to minimize contributions from partial volume effects.

DETAILED DESCRIPTION OF SEVERAL EMBODIMENTS

Figure 1:
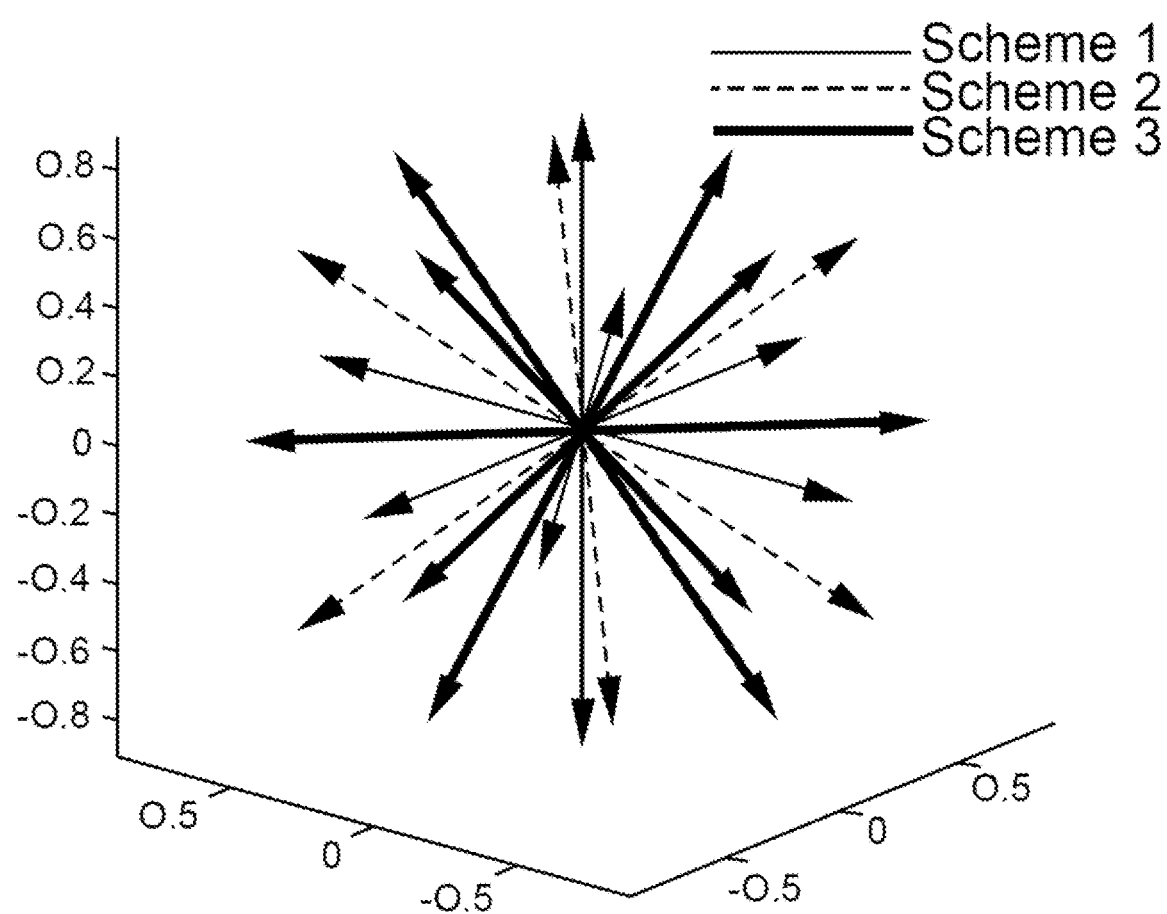
FIG. 1 illustrates representative diffusion gradient orientations for measuring average log signal attenuations $M_3(b)$, $M_4(b)$, and $M_6(b)$ for three representative IGDTI sampling schemes.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items unless indicated.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus are referred to as "lowest", "best", "minimum," or the like. It will be appreciated that such descriptions are intended to indicate that a selection among many used functional alternatives can be made, and such selections need not be better, smaller, or otherwise preferable to other selections.

Examples are described with reference to directions indicated as "above," "below," "upper," "lower," and the like. These terms are used for convenient description, but do not imply any particular spatial orientation. Similarly, particular coordinate axes are used, but other orientations of coordinate axes can be used. While directions of applied electric or magnetic fields, including gradient fields, are referred to as orthogonal or parallel to one another, such directions can be with 10, 5, 2, 1, 0.5, or 0.1 degrees from geometrically orthogonal or parallel. In general, directions associated with vectors are within 10, 5, 2, 1, 0.5, or 0.1 degrees of mathematically prescribed directions.

Signals obtained from diffusion-sensitized MR measurements are customarily referred to as signal attenuations, and are typically normalized with reference to a baseline MR image that is not diffusion-sensitized. Signals can be obtained that correspond to a single sample or sample volume, or a plurality of volume elements (voxels) that represent a sample image. As used herein, "image" refers to a visual image such as presented on a display device, or image data stored in one or more computer-readable media devices such as random access memory (RAM), hard disks, hard drives, CDs, DVDs. Such data can be stored in a variety of formats such as JEPG, TIFF, BMP, PNG, GIF, and others. Magnetic resonance (MR) images obtained with diffusion weightings are referred to as diffusion weighted images (DWIs). In the discussion below, processing of DWIs generally refers to voxel by voxel processing, i.e., processing operations are applied to voxels individually.

Directions are specified using vectors (typically unit vectors) expressed as [x, y, z], wherein x, y, z refer to corresponding coordinates in a rectilinear coordinate system. Vectors are alternatively expressed as column vectors instead of row vectors in the form $[x,y,z]^T$, wherein the superscript T denotes the transpose operation. Vectors can be expressed in other ways as well, and the notation used herein is chosen for convenient explanation. For convenience herein, vector and tensor quantities are shown in boldface text.

Gradient field diffusion sensitizations can be associated with different field strengths and gradient pulse durations. Typically, such sensitizations are described with reference to a b-value given by $$b = \gamma^2 G^2 \delta^2 \left(\Delta - \frac{\delta}{3}\right),$$

wherein, $\gamma$, $\delta$, and $\Delta$, are the magnetogyric ratio, a diffusion gradient pulse duration, a pulse separation, and G is a gradient field magnitude. Such b-values can depend on gradient pulse shape, but ranges can be specified using the expression above.

Generalized Multi-Order Diffusion Weighting

Diffusion tensor imaging (DTI) uses a $2^{nd}$ order tensor to model the diffusion signal measured in tissues using low b-values (up to ~1200 mm²/s). The diffusion signal measured in tissue at higher b-values is more anisotropic and higher order tensor (HOT) corrections are required to accurately describe it. HOT corrections to be determined depend on the magnitude of the b-value, and can conveniently be divided into three b-value groups (low, intermediate, high). Additional groups can be used depending on the selected range of b-values, particularly if many HOT corrections are of interest. The ranges used in the following description are one example. In the following, b-values ranges referred to as low, intermediate, and high are typically provided that are suitable for in vivo brain imaging. It may be preferred to adjust these ranges for other tissue types (e.g., liver, muscle, etc.) or experimental conditions (fixed brain, contrast agents).

IGDTI General Overview

IGDTI generally can provide orientationally-averaged diffusion measurements for a wide range of b-values. For example, IGDTI can produce orientationally-averaged measurements such as mADC-weighted images over a wide range of b-values as well as estimates of rotation invariant parameters such as the Traces of higher order diffusion tensors Tr(4), Tr(6), mean diffusivities of higher order diffusion tensor D(4), D(6)—these diffusivities are scaled versions of the traces, and t-mean diffusional kurtoses—derived from Tr(4) and Tr(2), or Tr(6) and Tr(2) respectively.

IGDTI can allow efficient acquisition of multiple orientationally-averaged (i.e., mADC-weighted images) over a wide range of b-values within clinically feasible scan durations. These data can be processed to estimate a probability density function (i.e., spectrum) of intravoxel orientationally-averaged mean diffusivities, (mADCs), in each imaging voxel, potentially allowing the visualization/discrimination of biologically-specific microscopic water pools characterized by different water mobilities in healthy and pathological tissues.

Sparse spatial-spectral whole-brain intravoxel mADC spectra can be displayed in a more intuitive manner by displaying the cumulative density function computed from the normalized probability density function in each voxel. In each voxel, the intravoxel normalized mADC spectrum can be decomposed into different tissue components (signal fractions) using tissue-specific orientationally-averaged mean diffusivity spectra known a priori, or estimated as an average normalized spectrum in a region-of-interest (ROI), or from normative values computed in atlases of healthy and patient populations. These signal fractions can be used to extract and visualize biologically-specific signal based on orientationally-averaged water diffusion properties (i.e., water mobilities).

Obtaining mADC-weighted data with multiple b-values for estimating intravoxel mADC spectra can be done by using IGDTI with:
a. 3-direction sampling for low b-values
b. 3-direction+4-direction sampling for intermediate b-values
c. 3-direction+4-direction+6-direction sampling for high b-values The nested structure of the angular sampling allows the possibility of acquiring similar orientations for images with different b-values (e.g., the same 3-direction scheme at all b-values). DWIs acquired along these directions with one b-value can be used as reference images for image registration (i.e., motion correction) of DWIs acquired along the same directions with a slightly different b-value. More generally, signal attenuation (geometric) averages acquired using a sampling scheme at a particular b-value can be used as reference images for image registration (i.e., motion correction) of signal attenuation (geometric) averages acquired using the same sampling scheme at a slightly different b-value.

Low Range (b Between 0 s/mm$^2$ and ~1200 s/mm$^2$)

For a fixed low b-value in this range, the orientational variation of the measured diffusion signal in tissue can be described with a $2^{nd}$ order diffusion tensor model and an mADC-weighted image is an image associated with the Trace of the $2^{nd}$ order diffusion tensor, Tr(2) or the mean diffusivity of the $2^{nd}$ order diffusion tensor, D(2)=⅓ Tr(2). An mADC-weighted image can be derived from any one of the three signal attenuation (geometric) average computed from images acquired with the same low b-value using one of the three orientation sampling schemes: 3-direction, 4-direction, or 6-direction, respectively. Either a geometric average of the signal attenuation or an arithmetic average of the log signal attenuation it typically used. These sampling schemes (described in detail below) can be rotated in any way as long as relative orientations within each scheme are the same. The Trace of the $2^{nd}$ order diffusion tensor (DTI) can be computed from one baseline (non-diffusion-weighted) image and one mADC-weighted image derived as described in 1c from measurements with a low b-value. For example, one baseline image at b=0 s/mm$^2$, and a 3-directional measurement at b=1000 s/mm$^2$.

Intermediate Range (Between ~1200 s/mm$^2$ and ~3600 s/mm$^2$)

For a fixed intermediate b-value, the orientational variation of the measured diffusion signal in tissue can be described with a $4^{th}$ order tensor model. An mADC-weighted image is an image associated with the Trace of the $2^{nd}$ order diffusion tensor, Tr(2)=3 D(2) and the Trace of the 4th order correction diffusion tensor, Tr(4)=5 D(4). For a fixed intermediate b-value, a mADC-weighted image can be derived from any two of the three signal attenuation (geometric) averages computed from images acquired with the same intermediate b-value using any two of the three orientation sampling schemes: 3-direction, 4-direction, and 6-direction, respectively. The Trace of the $2^{nd}$ order diffusion tensor (DTI) and the Trace of the $4^{th}$ order correction diffusion tensor can be computed from one baseline (non-diffusion-weighted) image, one mADC-weighted image with low b-value derived, and one mADC-weighted image with intermediate b-value derived as described in 2c. For example, one baseline b=0 s/mm$^2$, 3-direction scheme at b=1000 s/mm$^2$, and 3-direction scheme+4-direction scheme at b=2500 s/mm$^2$.

The signal averages can be combined linearly to give an mADC-weighted image at an intermediate b-value. However, it is not necessary to explicitly compute these averages. The same mADC-weighted image can be computed directly from a weighted average of 7 DWIs acquired with the same intermediate b-value using the 3-direction and 4-direction schemes, respectively (or any other combination of two schemes). Computing the averages for each scheme are intermediate steps (that can be omitted) that illustrate how these 7 directions can be combined to provide an orientationally-averaged result.

High Range (Between ~3600 s/mm$^2$ and ~10800 s/mm$^2$

For a fixed high b-value, the orientational variation of the measured diffusion signal in tissue can be described with a 6th order tensor model. For a fixed high b-value, an mADC-weighted image is an image associated with the Trace of the 2nd order diffusion tensor, the Trace of the 4th order correction diffusion tensor, and the Trace of the 6th order correction diffusion tensor. For a fixed high b-value, an mADC-weighted image can be derived from the three signal attenuation (geometric) averages computed from images acquired with the same high b-value and the 3-direction, 4-direction, and 6-direction, sampling schemes, respectively. The Trace of the 2nd order diffusion tensor (DTI), the Trace of the 4th order correction diffusion tensor, and the Trace of the 6th order correction diffusion tensor can be computed from one baseline (non-diffusion-weighted) image, one mADC-weighted image with low b-value, one mADC-weighted image with intermediate b-value, and one mADC-weighted with high b-value derived. For example, one baseline b=0 s/mm², 3-direction scheme at b=1000 s/mm², 3-direction scheme+4-direction scheme at b=2500 s/mm², 3-direction+4-direction+6-direction at b=5000 s/mm².

IGDTI Detailed Discussion

A diffusion MR signal S(G) produced by a pulsed-field gradient (PFG) spin-echo diffusion preparation with gradient $G = Gu^T = G[u_x, u_y, u_z]^T = G[\sin\theta\cos\phi, \sin\theta\sin\phi, \cos\theta]^T$ can be approximated in terms of HOTs using a cumulant expansion of the MR signal phase. Using the Einstein convention for tensor summation, a logarithm of diffusion signal attenuation S(G) can be expressed as:

$$\ln\frac{S(G)}{S_0} = \sum_{n=1}^{N} i^n b^{(n)}_{i_1 i_2 \ldots i_n} D^{(n)}_{i_1 i_2 \ldots i_n} \quad (1)$$

wherein $S_0$ is a baseline (non-diffusion weighted image), $D^{(n)}_{i_1 i_2 \ldots i_n}$ is a HOT of rank n in three-dimensional space ($i_k$=x, y, z) with physical units of mm$^n$/s, and $$b^{(n)}_{i_1 i_2 \ldots i_n} = \gamma^n \delta^n G^n \left(\Delta - \frac{n-1}{n+1}\delta\right) u_{i_1} u_{i_2} \ldots u_{i_n} \quad (2)$$

is a corresponding rank-n b-tensor with units of (s/mm)$^n$. In addition, $\gamma$, $\delta$, and $\Delta$, are the magnetogyric ratio, a diffusion gradient pulse duration, and a pulse separation, respectively.

In a long diffusion-time limit and in the absence of flow, the net displacement probability function of diffusing spins is symmetric with respect to an origin of a net displacement coordinate system and only tensors with even rank n contribute to the signal expansion in Eq. 1. Moreover, because these tensors are fully symmetric, tensor components with permuted spatial indices are equal. For example, for the 4th-order tensor $D^{(4)}$, $D^{(4)}_{xxyz} = D^{(4)}_{zxxy} = \ldots = D^{(4)}_{yzxx}$. These assumptions are generally valid for both in vivo and fixed-brain imaging and can permit significant reductions a number of unknown tensor components that need to be estimated with GDTI.

It is convenient to adopt the so-called "occupation number" notation by which $D^{(n)}_{n_x n_y n_z}$ denotes all equal (degenerate) tensor elements $D^{(n)}_{i_1 i_2 \ldots i_n}$ obtained from all possible permutations in which the spatial indices x, y, and z appear $n_x$, $n_y$, and $n_z$ times, respectively. With this notation, Eq. 1 can be written more compactly for fully symmetric diffusion processes by retaining only HOTs with even rank:

$$\ln\frac{S(G)}{S_0} = \sum_{n=2,4,6\ldots}^{N_{max}} \sum_{n_x+n_y+n_z=n} (-1)^{\frac{n}{2}} \beta_n u_x^{n_x} u_y^{n_y} u_z^{n_z} \mu_{n_x n_y n_z} D^{(n)}_{n_x n_y n_z}, \quad (3)$$

wherein $$\mu_{n_x n_y n_z} = \frac{n!}{n_x! n_y! n_z!}$$

represents the multiplicity of each unique HOT component $D^{(n)}_{n_x n_y n_z}$ of rank $n = n_x + n_y + n_z$, and the scalar $$\beta_n = \gamma^n \delta^n G^n \left(\Delta - \frac{n-1}{n+1}\delta\right)$$

is an orientation-averaged diffusion sensitization factor for order n. In most image acquisitions in which b-values are varied, the gradient magnitude G is varied and the pulse duration is fixed.

An orientationally-averaged (isotropic) measurement of the log attenuation $$\left\langle \ln\frac{S(G)}{S_0} \right\rangle_S$$

can be obtained by integrating Eq. 3 over all possible orientations on the unit sphere. Using the following identity derived in Mathematical Supplement A below:

$$\frac{1}{4\pi}\int u_x^{n_x} u_y^{n_y} u_z^{n_z} d\Omega_u = \frac{K_{n_x n_y n_z}}{(n+1)} \frac{\mu_{\frac{n_x}{2} \frac{n_y}{2} \frac{n_z}{2}}}{\mu_{n_x n_y n_z}}, \quad (4)$$

wherein $K_{n_x n_y n_z} = 1$ when $n_x$, $n_y$, and $n_z$ are all even, and $K_{n_x n_y n_z} = 0$ otherwise. The integral of Eq. 3 over all orientations on the unit sphere becomes:

$$\left\langle \ln\frac{S(G)}{S_0} \right\rangle_S = \sum_{n=2,4,6\ldots}^{N_{max}} \sum_{n_x+n_y+n_z=n} (-1)^{\frac{n}{2}} K_{n_x n_y n_z} \beta_n \frac{\mu_{\frac{n_x}{2} \frac{n_y}{2} \frac{n_z}{2}}}{(n+1)} D^{(n)}_{n_x n_y n_z}. \quad (5)$$

Note that the orientation-averaged signal is weighted by the generalized traces of HOTs of even ranks, n defined as:

$$TrD^{(n)} = \sum_{n_x+n_y+n_z=n} K_{n_x n_y n_z} \mu_{\frac{n_x}{2} \frac{n_y}{2} \frac{n_z}{2}} D^{(n)}_{n_x n_y n_z}, \quad (6)$$

which is related to the generalized mean diffusivity of order n:

$$\overline{D}^{(n)} = \frac{TrD^{(n)}}{n+1}.$$

Eq. 5 describes the orientation-averaged signal at arbitrary diffusion sensitization obtained from a very large number of DWIs acquired with orientations uniformly sampling the unit sphere.

In practice the acquisition of such large data sets is infeasible for pre-clinical and clinical applications. In the next section a general strategy for efficient diffusion gradient sampling schemes is described that allows fast computation of rotation-invariant diffusion weightings at high b-values using only a few image acquisitions.

Efficient Isotropic GDTI (IGDTI)

The weightings of unique tensor elements $D_{n_x n_y n_z}^{(n)}$ in the expression for the orientation-averaged (i.e., trace-weighted) log signal attenuation in Eq. 5 generally satisfy two properties:

1. Only diffusion tensor components with all even indices, $n_x$, $n_y$, $n_z$ have non-zero weightings (i.e., $K_{n_x n_y n_z}=0$, unless $n_x$, $n_y$, $n_z$ are all even); and
2: The non-zero weightings of $D_{n_x n_y n_z}^{(n)}$ (i.e., $$\mu_{\frac{n_x n_y n_z}{2 2 2}})$$

do not depend on the order of the spatial indices x, y, and z. Diffusion gradient sampling schemes can be selected to achieve signal weightings satisfying these conditions via linear combinations of measured log(DWI). Second, multiple signals can be linearly combined to obtain precise weightings for $D_{n_x n_y n_z}^{(n)}$ required for an orientationally-averaged measurement (Eq. 5) and for the computation of the HOT generalized Traces (Eq. 6) from a small total number of DWIs.

Starting with an arbitrary orientation for the applied diffusion gradient vector $u^T = [u_x, u_y, u_z]^T$, wherein $u^T$ is a unit vector, an orientationally averaged weighting scheme satisfying both (1) and (2) can be constructed using only 12 DWIs. First, to achieve zero weighting for all HOT components with at least one odd index $n_x$, $n_y$, $n_z$ (1), the log signal attenuations (Eq. 3) of 4 DWIs acquired with the same b-value and the following four gradient orientations $[-u_x, u_y, u_z]^T$, $[u_x, -u_y, u_z]^T$, $[u_x, u_y, -u_z]^T$, and $[-u_x, -u_y, -u_z]^T$ are averaged to obtain:

$$\left\langle \ln \frac{S(G)}{S_0} \right\rangle_4 = \tag{7}$$

$$\sum_{n=2,4,6...}^{N_{max}} \sum_{n_x+n_y+n_z=n} (-1)^{\frac{n}{2}} K_{n_x n_y n_z} \beta_n u_x^{n_x} u_y^{n_y} u_z^{n_z} \mu_{n_x n_y n_z} D_{n_x n_y n_z}^{(n)}$$

Second, to ensure that all tensor components $D_{n_x n_y n_z}^{(n)}$ have the same weighting in Eq. 7 when the spatial indices x, y, and z are permuted (2), the first step is repeated for three unit vectors $[u_x, u_y, u_z]^T$, $[u_z, u_x, u_y]^T$, and $[u_y, u_z, u_x]^T$ derived from the unit vector $u^T$. The general expression for the log signal attenuation averaged over the 12 DWIs is:

$$\left\langle \ln \frac{S(G)}{S_0} \right\rangle_{12} = \tag{8}$$

$$\frac{1}{3} \sum_{n=2,4,6...}^{N_{max}} \sum_{n_x+n_y+n_z=n} (-1)^{\frac{n}{2}} K_{n_x n_y n_z} \beta_n \left( u_x^{n_x} u_y^{n_y} u_z^{n_z} + u_x^{n_z} u_y^{n_x} u_z^{n_y} + u_x^{n_y} u_y^{n_z} u_z^{n_x} \right) \mu_{n_x n_y n_z} D_{n_x n_y n_z}^{(n)}$$

Note that in the above, there are a total of 12 independent possibilities, the four gradient directions and the three permutations of each. Note that selection of these gradient directions permits signal acquisition based on HOTs, but gradient directions that are substantially different and satisfy the above constraints can enhance measurements.

Due to the inherent symmetries of the HOTs, the number of DWIs necessary for computing the average log signal attenuations satisfying (1a) and (2) in Eq. 8 can be significantly reduced for three special cases of the unit vector, u (see FIG. 1):

Scheme 1:

Starting with $u=[1,0,0]^T$ only three of the twelve measurements are unique. Therefore the average log signal attenuation in Eq. 8, henceforth denoted by $M_3(b)$ for this sampling scheme, can be measured from only three DWIs. The associated gradient directions are $[1,0,0]^T$, $[0,1,0]^T$, $[0,0,1]^T$. In general, any three orthogonal directions can be used.

Scheme 2: Starting with $$u = \left[ \frac{1}{\sqrt{3}}, \frac{1}{\sqrt{3}}, \frac{1}{\sqrt{3}} \right]^T,$$

only four of the twelve measurements are unique. Therefore the average log signal attenuation in Eq. 8, henceforth denoted by $M_4(b)$ for this sampling scheme, can be measured from only four DWIs. The associated gradient directions are:

$$\left[ \frac{1}{\sqrt{3}}, \frac{1}{\sqrt{3}}, \frac{1}{\sqrt{3}} \right]^T, \left[ \frac{-1}{\sqrt{3}}, \frac{1}{\sqrt{3}}, \frac{1}{\sqrt{3}} \right]^T,$$

$$\left[ \frac{1}{\sqrt{3}}, \frac{-1}{\sqrt{3}}, \frac{1}{\sqrt{3}} \right]^T, \left[ \frac{1}{\sqrt{3}}, \frac{1}{\sqrt{3}}, \frac{-1}{\sqrt{3}} \right]^T.$$

In general, any four directions that are evenly spaced in the unit sphere can be used, and the above is a representative example expressed with respect to a particular coordinate system.

Scheme 3: Starting with $$u = \left[ \frac{1}{\sqrt{2}}, \frac{1}{\sqrt{2}}, 0 \right]^T$$

only six of the twelve measurements are unique. Therefore the average log signal attenuation in Eq. 8, henceforth denoted by $M_6(b)$ for this sampling scheme, can be measured from only six DWIs. The associated gradient directions are $$\left[ \frac{1}{\sqrt{2}}, \frac{1}{\sqrt{2}}, 0 \right]^T, \left[ \frac{-1}{\sqrt{2}}, \frac{1}{\sqrt{2}}, 0 \right]^T, \left[ \frac{1}{\sqrt{2}}, \frac{-1}{\sqrt{2}}, 0 \right]^T,$$

-continued $$\left[\frac{1}{\sqrt{2}}, \frac{1}{\sqrt{2}}, 0\right]^T, \left[0, \frac{1}{\sqrt{2}}, \frac{1}{\sqrt{2}}\right]^T, \left[\frac{1}{\sqrt{2}}, 0, \frac{1}{\sqrt{2}}\right]^T.$$

In general, any six directions defined by two orthogonal axes in each of three mutually orthogonal planes are suitable. Typically, the orthogonal planes are defined by coordinate axes that define a rectilinear coordinate system such as xy, xz, and yz planes, and the two orthogonal axes in each of these planes are at angles of 45 degrees with respect to the coordinate axes that define the planes. Each of the two orthogonal axes is angularly equidistant from directions of the coordinate axes that define the associated orthogonal plane. As in all schemes, any particular direction and its antipodal direction are equivalent due diffusion tensor symmetry. The gradient orientations are summarized in Table 1 below.

TABLE 1

Reduced Sets of Gradient Directions

| Scheme | # DWIs | Diffusion Gradient Orientations | M(b) |
|---|---|---|---|
| 1 | 3 | [1, 0, 0], [0, 1, 0], [0, 0, 1] | $M_3(b)$ |
| 2 | 4 | $\left[\frac{1}{\sqrt{3}}, \frac{1}{\sqrt{3}}, \frac{1}{\sqrt{3}}\right], \left[\frac{-1}{\sqrt{3}}, \frac{1}{\sqrt{3}}, \frac{1}{\sqrt{3}}\right], \left[\frac{1}{\sqrt{3}}, \frac{-1}{\sqrt{3}}, \frac{1}{\sqrt{3}}\right], \left[\frac{1}{\sqrt{3}}, \frac{1}{\sqrt{3}}, \frac{-1}{\sqrt{3}}\right]$ | $M_4(b)$ |
| 3 | 6 | $\left[\frac{1}{\sqrt{2}}, \frac{1}{\sqrt{2}}, 0\right], \left[\frac{1}{\sqrt{2}}, \frac{-1}{\sqrt{2}}, 0\right], \left[0, \frac{1}{\sqrt{2}}, \frac{1}{\sqrt{2}}\right],$ $\left[0, \frac{1}{\sqrt{2}}, \frac{-1}{\sqrt{2}}\right], \left[\frac{1}{\sqrt{2}}, 0, \frac{1}{\sqrt{2}}\right], \left[\frac{-1}{\sqrt{2}}, 0, \frac{1}{\sqrt{2}}\right]$ | $M_6(b)$ |

FIG. 1 illustrates gradient directions associated with Schemes 1, 2, and 3 with reference to a particular coordinate system.

The average log signal attenuations, $M_3(b)$, $M_4(b)$, and $M_6(b)$, derived from sampling Schemes 1, 2, and 3, respectively, satisfy (1) and (2) and can be linearly combined to achieve the precise weightings of HOT elements $D_{n_x n_y n_z}^{(n)}$ (up to n=6) required for an orientationally-averaged (i.e., isotropic or mADC-weighted) measurements with high b-value (Eq. 6). Table 2 summarizes the relative weightings of unique tensor elements $D_{n_x n_y n_z}^{(n)}$ in $M_3(b)$, $M_4(b)$, and $M_6(b)$, as well as in $Tr^{(n)}$ and $\overline{D^{(n)}}$ (up to n=6).

TABLE 2

Relative Weightings of HOT Elements

| HOT component | $M_3$ (3 DWIs) | $M_4$ (4 DWIs) | $M_6$ (6 DWIs) | $Tr^{(n)}$ | $\overline{D^{(n)}}$ |
|---|---|---|---|---|---|
| $D_{200}$ | 1/3 | 1/3 | 1/3 | 1 | 1/3 |
| $D_{400}$ | 1/3 | 1/9 | 1/6 | 1 | 1/5 |
| $D_{220}$ | 0 | 2/3 | 1/2 | 2 | 2/5 |
| $D_{600}$ | 1/3 | 1/27 | 1/12 | 1 | 1/7 |
| $D_{420}$ | 0 | 5/9 | 15/24 | 3 | 3/7 |
| $D_{222}$ | 0 | 10/3 | 0 | 6 | 6/7 |

Table 3 summarizes linear combinations of $M_3(b)$, $M_4(b)$, and $M_6(b)$ that achieve orientation-averaged diffusion weightings for selected combinations of HOTs in different b-value ranges suggested based on the diffusivities of fixed and live brain tissue.

TABLE 3

Signal Combinations for mADCs obtained from HOTs

| | | | | b-value range (s/mm$^2$) | |
|---|---|---|---|---|---|
| Order | Schemes | # DWIs | Orientation Averaged Signal | In vivo | Fixed brain |
| 2 | 1 | 3 | $M_3(b) \cong -\beta_2 \overline{D^{(2)}}$ | 0-1200 | 0-2000 |
| | 2 | 4 | $M_4(b) \cong -\beta_2 \overline{D^{(2)}}$ | | |
| | 3 | 6 | $M_6(b) \cong -\beta_2 \overline{D^{(2)}}$ | | |

TABLE 3-continued

Signal Combinations for mADCs obtained from HOTs

| Order | Schemes | # DWIs | Orientation Averaged Signal | b-value range (s/mm²) In vivo | b-value range (s/mm²) Fixed brain |
|---|---|---|---|---|---|
| 4 | 1 and 2 | 3 + 4 | $\frac{1}{5}(2M_3(b) + 3M_4(b)) \cong -\beta_2\overline{D^{(2)}} + \beta_4\overline{D^{(4)}}$ | 1200-3600 | 2000-6000 |
|  | 1 and 3 | 3 + 6 | $\frac{1}{5}(1M_3(b) + 4M_6(b)) \cong -\beta_2\overline{D^{(2)}} + \beta_4\overline{D^{(4)}}$ |  |  |
| 6 | 1, 2, and 3 | 3 + 4 + 6 | $\frac{1}{7}\left(\frac{10}{5}M_3(b) + \frac{9}{5}M_4(b) + \frac{16}{5}M_6(b)\right) \cong -\beta_2\overline{D^{(2)}} + \beta_4\overline{D^{(4)}} - \beta_6\overline{D^{(6)}}$ | 3600-10800 | 6000-18000 |

Mean values can be computed by solving the linear equations in Table 3. Note that the signals are scaled by a parameter β so that HOT terms become more significant for larger values of b, the diffusion encoding gradient.

IGDTI-Derived Microstructural Parameters

Depending on the b-value and tissue mean diffusivity, the diffusion signal can often be adequately approximated by truncating the sum in Eq. 5 and ignoring contributions from generalized diffusion tensors with higher order. With the appropriate truncations (see Table 3), Schemes 1, 2, and 3 can be combined for efficient IGDTI measurements that achieve rotation-invariant (i.e., mADC) weightings for a wide range of diffusion sensitizations. The most efficient IGDTI sampling schemes that achieve isotropic HOT weighting up to orders 2, 4, and 6 require 3, 7, and 13 DWIs, respectively, and are shaded in Table 3. Specifically, mADC-weighted DWIs can be produced from only one baseline image and 3 DWIs for low b-values, 3+4=7 DWIs for intermediate b-values, and 3+4+6=13 DWIs for high b-values. Moreover, from at least three mADC-weighted DWIs sampled in different b-value regimes (which can be obtained from one baseline image and 3+7+13=23 DWIs), generalized mean diffusivities $\overline{D^{(2)}}$, $\overline{D^{(4)}}$, and $\overline{D^{(6)}}$, respectively (and implicitly HOT Traces $TrD^{(2)}$, $TrD^{(4)}$, $TrD^{(6)}$) can be obtained by solving the linear system of equations corresponding to the shaded rows in Table 3. Other useful rotation-invariant microstructural parameters that are related to these generalized mean diffusivities can be determined, such as the mean t-kurtosis:

$$\overline{W} = \frac{6\overline{D^{(4)}}\left(\Delta - \frac{3\delta}{5}\right)}{\overline{D^{(2)}}^2\left(\Delta - \frac{\delta}{3}\right)^2} \quad (9)$$

Note that $\overline{W}$ is dimensionless and is derived from a polynomial expansion of the log signal attenuation (a cumulant expansion) with respect to the b-matrix, not the q-vector, hence the additional factors related to gradient pulse timings in Eq. 9. In the limit of an infinitely short gradient pulse duration, δ, the two approaches are identical for fully symmetric diffusion.

Mathematical Supplement A

The orientationally-averaged diffusivity (generalized mean diffusivity) for an HOT of order n, $D^{(n)}$ can be determined by evaluating the following integral over the unit sphere:

$$\overline{D^{(n)}} = \frac{1}{4\pi}\int \sum_{n_x+n_y+n_z=n} \mu_{n_x n_y n_z} u_x^{n_x} u_y^{n_y} u_z^{n_z} D_{n_x n_y n_z} d\Omega_u \quad (A1)$$

wherein $$\mu_{n_x n_y n_z} = \frac{(n_x + n_y + n_z)!}{n_x! n_y! n_z!} \quad (A2)$$

are the multiplicities (degeneracies) of the equal components $D_{n_x n_y n_z}$ in the fully symmetric tensor of even rank n, $D^{(n)}$ with $n_x+n_y+n_z=n$, and $u^T=[u_x, u_y, u_z]^T$ is a unit vector.

Note that $\int u_x^{n_x} u_y^{n_y} u_z^{n_z} d\Omega_u$ reduces to 0 if any of the indices $n_x$, $n_y$, or $n_z$ is odd. Writing $u^T=[\sin\theta\cos\phi, \sin\theta\sin\phi, \cos\theta]^T$ in spherical coordinates, then:

$$\int u_x^{n_x} u_y^{n_y} u_z^{n_z} d\Omega_u = \quad (A3)$$
$$K_{n_x n_y n_z}\int_0^\pi (\sin\theta)^{n_1+n_2+1}(\cos\theta)^{n_3}d\theta \int_0^{2\pi}(\sin\phi)^{n_2}(\cos\phi)^{n_1}d\phi$$

wherein $K_{n_x n_y n_z}=1$ when $n_x$, $n_y$, $n_z$ are all even, and $K_{n_x n_y n_z}=0$ otherwise.

Next, using the definition of the Beta function, or the Euler integral of the first kind:

$$B(x, y) = \int_0^1 t^{x-1}(1-t)^{y-1}dt \quad (A4)$$

After a change of variable t→(sin θ)²:

$$B(x, y) = 2\int_0^{\frac{\pi}{2}}(\sin\theta)^{2x-1}(\cos\theta)^{2y-1}d\theta \quad (A5)$$

Substituting Eq. A5 in A3

$$\int u_x^{n_x} u_y^{n_y} u_z^{n_z} d\Omega_u = 2B\left(\frac{n_1}{2}+\frac{n_2}{2}+1, \frac{n_3}{2}+\frac{1}{2}\right)B\left(\frac{n_2}{2}+\frac{1}{2}, \frac{n_1}{2}+\frac{1}{2}\right) \quad (A6)$$

and using the relationship between the Beta and Gamma functions $$B(x, y) = \frac{\Gamma(x)\Gamma(y)}{\Gamma(x+y)} \quad (A7)$$

then $$\int u_x^{n_x} u_y^{n_y} u_z^{n_z} d\Omega_u = 2 \frac{\Gamma\left(\frac{n_1}{2} + \frac{1}{2}\right)\Gamma\left(\frac{n_2}{2} + \frac{1}{2}\right)\Gamma\left(\frac{n_3}{2} + \frac{1}{2}\right)}{\Gamma\left(\frac{n_1 + n_2 + n_3}{2} + \frac{3}{2}\right)} \quad (A8)$$

Finally, using the property of the Gamma function $$\Gamma\left(n + \frac{1}{2}\right) = \frac{(2n)!}{4^n n!}\sqrt{\pi} \quad (A9)$$

for a positive integer n:

$$\int u_x^{n_x} u_y^{n_y} u_z^{n_z} d\Omega_u = \quad (A10)$$

$$\frac{4\pi}{(n_1 + n_2 + n_3 + 1)} \frac{\left(\frac{n_1}{2} + \frac{n_2}{2} + \frac{n_3}{2}\right)!}{(n_1 + n_2 + n_3)!} \frac{\frac{n_1}{2}!\frac{n_2}{2}!\frac{n_3}{2}!}{n_1!n_2!n_3!} = \frac{4\pi}{n+1} \frac{\mu_{\frac{n_x n_y n_z}{2\,2\,2}}}{\mu_{n_x n_y n_z}}$$

Substituting this result back into Eq. A1 gives $$\overline{D^{(n)}} = \frac{1}{n+1} \sum_{n_x + n_y + n_z = n} K_{n_x n_y n_z} \frac{\mu_{\frac{n_x n_y n_z}{2\,2\,2}}}{2\,2\,2} D_{n_x n_y n_z} \quad (A11)$$

Mathematical Supplement B

The definition of W and $\overline{W}$ can be extended to HOTs using a cumulant expansion. The $4^{th}$-order kurtosis tensor, W, quantifies the statistical standardized central moment of the probability density function (PDF) of spin displacements, P(r), and can be related to the $4^{th}$-order statistical cumulant tensor of P(r)

$$W_{ijkl} = \quad (B1)$$

$$9\frac{\langle r_i r_j r_k r_l\rangle - \langle r_i r_j\rangle\langle r_m r_n\rangle - \langle r_i r_m\rangle\langle r_j r_n\rangle - \langle r_i r_n\rangle\langle r_j r_m\rangle}{\langle r \cdot r\rangle^2} = 9\frac{Q^{(4)}_{ijkl}}{\langle r \cdot r\rangle^2}$$

In general, assuming fully symmetric diffusion, the cumulant tensor of rank-n, $Q_{ijkl}^{(n)}$ is related to the generalized diffusion tensor as described in (12)

$$Q^{(n)} = (-1)^n n! D^{(n)}\left(\Delta - \frac{n-1}{n+1}\delta\right) \quad (B2)$$

We can generalize W with respect to the HOTs $D^{(n)}$, and define the dimensionless rank-n tensor, $W^{(n)}$, as the standardized statistical cumulants of P(r)

$$W^{(n)} = \frac{n! D^{(n)}\left(\Delta - \frac{(n-1)}{(n+1)}\delta\right)}{2^{\frac{n}{2}} \overline{D^{(2)}}^{\frac{n}{2}} \left(\Delta - \frac{\delta}{3}\right)^{\frac{n}{2}}} \quad (B3)$$

The mean of tensor $W^{(n)}$, $\overline{W^{(n)}}$, is directly related to the mean of $D^{(n)}$ and implicitly to the generalized Trace, $\text{Tr}D^{(n)}$.

It is important to note that $\overline{W^{(4)}} = \overline{W}$ and $W^{(4)}$ quantifies the apparent diffusional kurtosis along any direction u, K(u), i.e., the $4^{th}$-order standardized central moment of P(r), as defined in (16):

$$K(u) = \frac{\langle (r \cdot u)^4\rangle}{\langle (r \cdot u)^2\rangle^2} - 3 = \sum_{i,j,k,l} \frac{\overline{D}^2}{[D(u)]^2} u_i u_j u_k u_l W_{ijkl} \quad (B4)$$

Where $\overline{D}$ is the mean diffusivity from DTI (i.e., $\overline{D^{(2)}}$) and D(u) is the apparent diffusivity along u, $$D(u) = \frac{\langle (r \cdot u)^2\rangle}{2t} = \sum_{i,j} u_i u_j D_{ij} = \sum_{i,j} u_i u_j \frac{\langle r_i r_j\rangle}{2t}, \quad (B6)$$

wherein $$D_{ij} = \frac{\langle r_i r_j\rangle}{2t}$$

represents the components of the diffusion tensor, r is the microscopic net spin displacement, t is the diffusion time, and the operation $\langle \cdot \rangle$ represents the ensemble average over the spin population in P(r). For n>4, $W^{(n)}$ depends on the standardized central moment tensors $$\frac{\langle (r \cdot u)^n\rangle}{\langle (r \cdot u)^2\rangle^{\frac{n}{2}}}$$

up to order n. For example, if n=6 the relation is:

$$\sum_{i,j,k,l} \frac{\overline{D}^3}{[D(u)]^3} u_i u_j u_k u_l u_m u_n W^{(6)}_{ijklmn} = \frac{\langle (r \cdot u)^6\rangle}{\langle (r \cdot u)^2\rangle^3} - 15\frac{\langle (r \cdot u)^4\rangle}{\langle (r \cdot u)^2\rangle^2} + 30. \quad (B7)$$

Representative MR Measurement Apparatus

Figure 2:
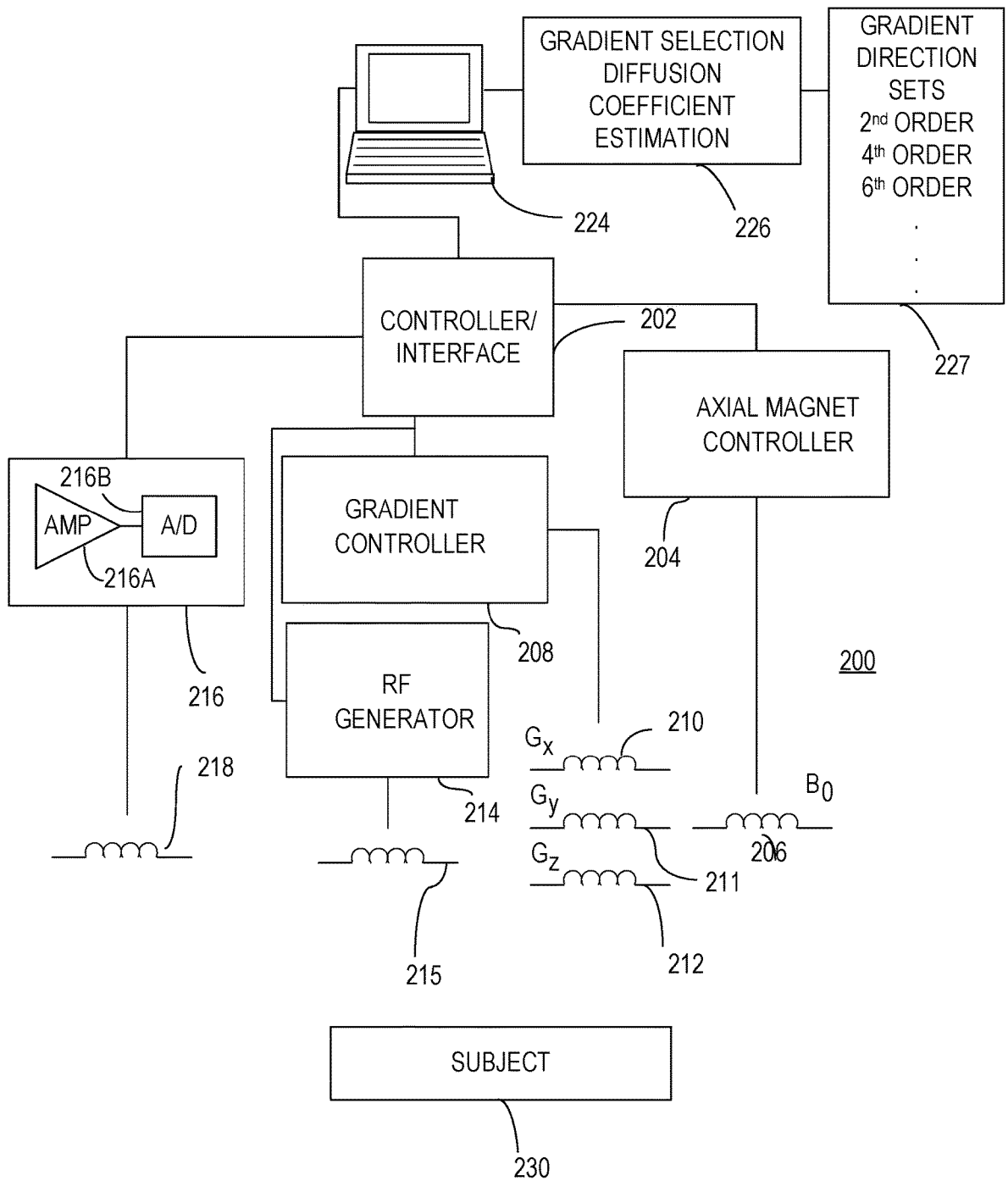
FIG. 2 illustrates a representative magnetic resonance imaging (MRI) system that includes signal processing so as to estimate mean apparent diffusion coefficients (mADCs).

MR measurements can be obtained using an MRI apparatus 200 as illustrated in FIG. 2. The apparatus 200 includes a controller/interface 202 that can be configured to apply selected magnetic fields such as constant or pulsed field gradients to a subject 230 or other specimen. An axial magnet controller 204 is in communication with an axial magnet 206 that is generally configured to produce a substantially constant magnetic field Bo. A gradient controller 208 is configured to apply a constant or time-varying magnetic field gradient in a selected direction or in a set of directions such as shown above using magnet coils 210-212 to produce respective magnetic field gradient vector components $G_x$, $G_y$, $G_z$ or combinations thereof. An RF generator 214 is configured to deliver one or more RF pulses to a specimen using a transmitter coil 215. An RF receiver 216 is in communication with a receiver coil 218 and is configured to detect or measure net magnetization of spins. Typically, the RF receiver includes an amplifier 216A and an analog-to-digital convertor 216B that detect and digitized received signals. Slice selection gradients can be applied with the same hardware used to apply the diffusion gradients. The gradient controller 208 can be configured to produce pulses or other gradient fields along one or more axes using any of Schemes 1-3 above, or other schemes. By selection of such gradients and other applied pulses, various imaging and/or measurement sequences can be applied. Sequences that produce variations that are functions of diffusion coefficients including coefficients of HOTs are typically based on sensitizing gradient fields.

For imaging, specimens are divided into volume elements (voxels) and MR signals for a plurality of gradient directions are acquired as discussed above. In some cases, MR signals are acquired as a function of b-values as well. In typical examples, signals are obtained for some or all voxels of interest. A computer 224 or other processing system such as a personal computer, a workstation, a personal digital assistant, laptop computer, smart phone, or a networked computer can be provided for acquisition, control and/or analysis of specimen data. The computer 224 generally includes a hard disk, a removable storage medium such as a floppy disk or CD-ROM, and other memory such as random access memory (RAM). Data can also be transmitted to and from a network using cloud-based processors and storage. N.B. Data could be uploaded to the Cloud or stored elsewhere. Computer-executable instructions for data acquisition or control can be provided on a floppy disk or other storage medium, or delivered to the computer 224 via a local area network, the Internet, or other network. Signal acquisition, instrument control, and signal analysis can be performed with distributed processing. For example, signal acquisition and signal analysis can be performed at different locations. The computer 224 can also be configured to select gradient field directions, determine mADCs based on acquired signals, and select b-values using suitable computer-executable instructions stored in a memory 227. In addition, field directions can be stored in the memory 227. Signal evaluation can be performed remotely from signal acquisition by communicating stored data to a remote processor. In general, control and data acquisition with an MRI apparatus can be provided with a local processor, or via instruction and data transmission via a network.

Representative Data Acquisition and Control Apparatus

Figure 3:
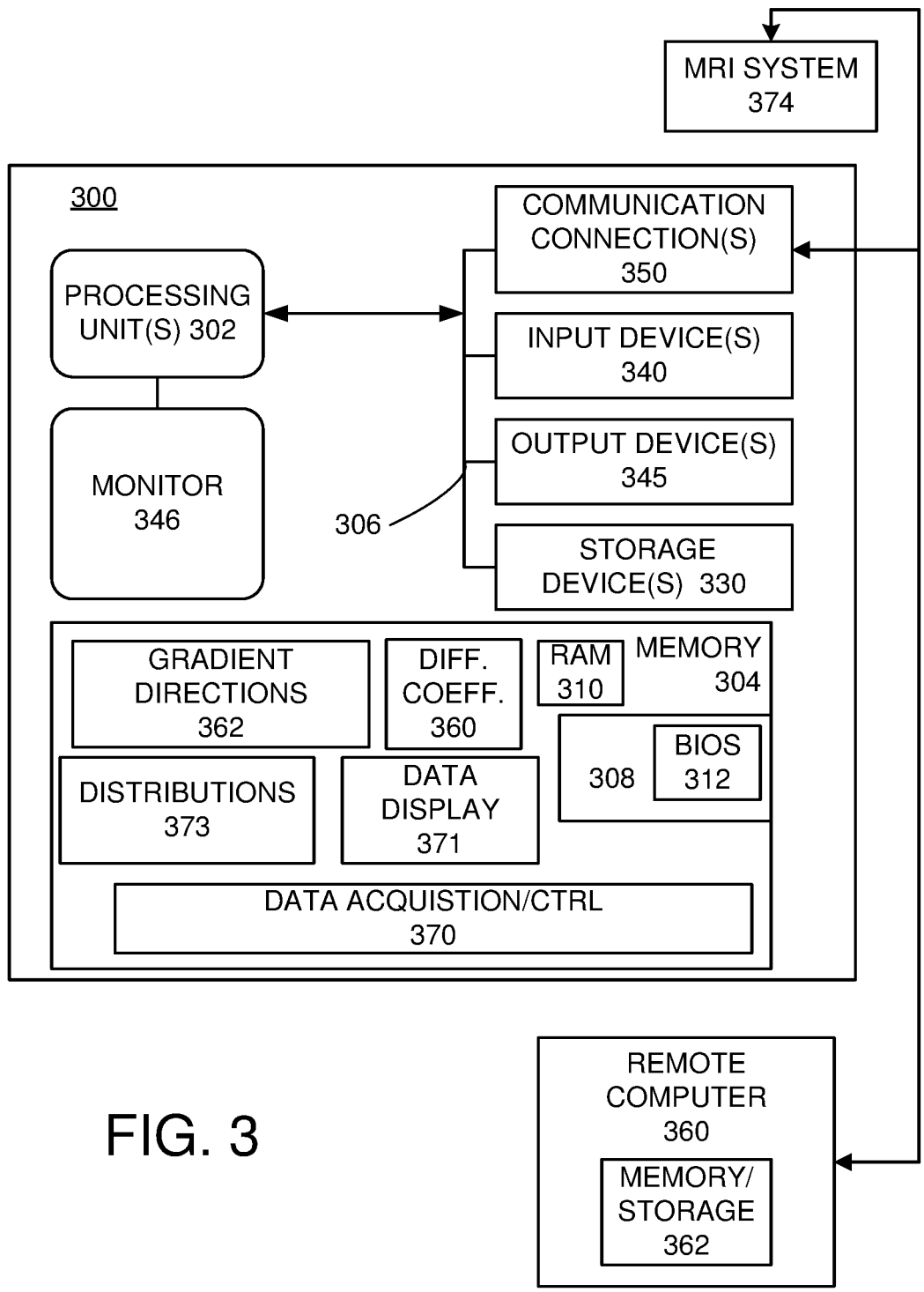
FIG. 3 illustrates a representative computing and control environment for measuring and processing IGDTI signal attenuations.

FIG. 3 and the following discussion are intended to provide a brief, general description of an exemplary computing/data acquisition environment in which the disclosed technology may be implemented. Although not required, the disclosed technology is described in the general context of computer executable instructions, such as program modules, being executed by a personal computer (PC), a mobile computing device, tablet computer, or other computational and/or control device. Generally, program modules include routines, programs, objects, components, data structures, etc., that perform particular tasks or implement particular abstract data types. Moreover, the disclosed technology may be implemented with other computer system configurations, including hand held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 3, an exemplary system for implementing the disclosed technology includes a general purpose computing device in the form of an exemplary conventional PC 300, including one or more processing units 302, a system memory 304, and a system bus 306 that couples various system components including the system memory 304 to the one or more processing units 302. The system bus 306 may be any of several types of bus structures including a memory bus or memory controller, a peripheral bus, and a local bus using any of a variety of bus architectures. The exemplary system memory 304 includes read only memory (ROM) 308 and random access memory (RAM) 310. A basic input/output system (BIOS) 312, containing the basic routines that help with the transfer of information between elements within the PC 300, is stored in ROM 308.

The exemplary PC 300 further includes one or more storage devices 330 such as a hard disk drive for reading from and writing to a hard disk, a magnetic disk drive for reading from or writing to a removable magnetic disk, an optical disk drive for reading from or writing to a removable optical disk (such as a CD-ROM or other optical media), and a solid state drive. Such storage devices can be connected to the system bus 306 by a hard disk drive interface, a magnetic disk drive interface, an optical drive interface, or a solid state drive interface, respectively. The drives and their associated computer readable media provide nonvolatile storage of computer-readable instructions, data structures, program modules, and other data for the PC 300. Other types of computer-readable media which can store data that is accessible by a PC, such as magnetic cassettes, flash memory cards, digital video disks, CDs, DVDs, RAMs, ROMs, and the like, may also be used in the exemplary operating environment.

A number of program modules may be stored in the storage devices 330 including an operating system, one or more application programs, other program modules, and program data. A user may enter commands and information into the PC 300 through one or more input devices 340 such as a keyboard and a pointing device such as a mouse. Other input devices may include a digital camera, microphone, joystick, game pad, satellite dish, scanner, or the like. These and other input devices are often connected to the one or more processing units 302 through a serial port interface that is coupled to the system bus 306, but may be connected by other interfaces such as a parallel port, game port, or universal serial bus (USB). A monitor 346 or other type of display device is also connected to the system bus 306 via an interface, such as a video adapter. Other peripheral output devices, such as speakers and printers (not shown), may be included.

The PC 300 may operate in a networked environment using logical connections to one or more remote computers, such as a remote computer 360. In some examples, one or more network or communication connections 350 are included. The remote computer 360 may be another PC, a server, a router, a network PC, or a peer device or other common network node, and typically includes many or all of the elements described above relative to the PC 300, although only a memory storage device 362 has been illustrated in FIG. 3. The personal computer 300 and/or the remote computer 360 can be connected to a logical a local area network (LAN) and a wide area network (WAN). Such networking environments are commonplace in offices, enterprise wide computer networks, intranets, and the Internet.

When used in a LAN networking environment, the PC 300 is connected to the LAN through a network interface. When used in a WAN networking environment, the PC 300 typically includes a modem or other means for establishing communications over the WAN, such as the Internet. In a networked environment, program modules depicted relative to the personal computer 300, or portions thereof, may be stored in the remote memory storage device or other locations on the LAN or WAN. The network connections shown are exemplary, and other means of establishing a communications link between the computers may be used.

The memory 304 generally includes computer-executable instructions for selecting gradient field directions, averaging acquired signals, and estimation on one or more higher order mADCs or other related specimen characteristics. For example, memory portion 362 can store computer-executable instructions for selected gradient field directions based on schemes as illustrated above. Computer-executable instructions for processing acquired signals (for example, combining as described above) can be stored in a memory portion 363. Computer-executable instructions for data acquisition and control are stored in a memory portion 370. Acquired and processed data (e.g., mADC based images) can be displayed using computer-executable instructions stored at memory portion 371. Computer-executable instructions for determining distributions of higher order mADCs can be provided in a memory portion 373. As noted above, data acquisition, processing, and instrument control can be provided at an MRI system 374, or distributed at one or more processing devices using a LAN or WAN.

Representative Methods

Figure 4:
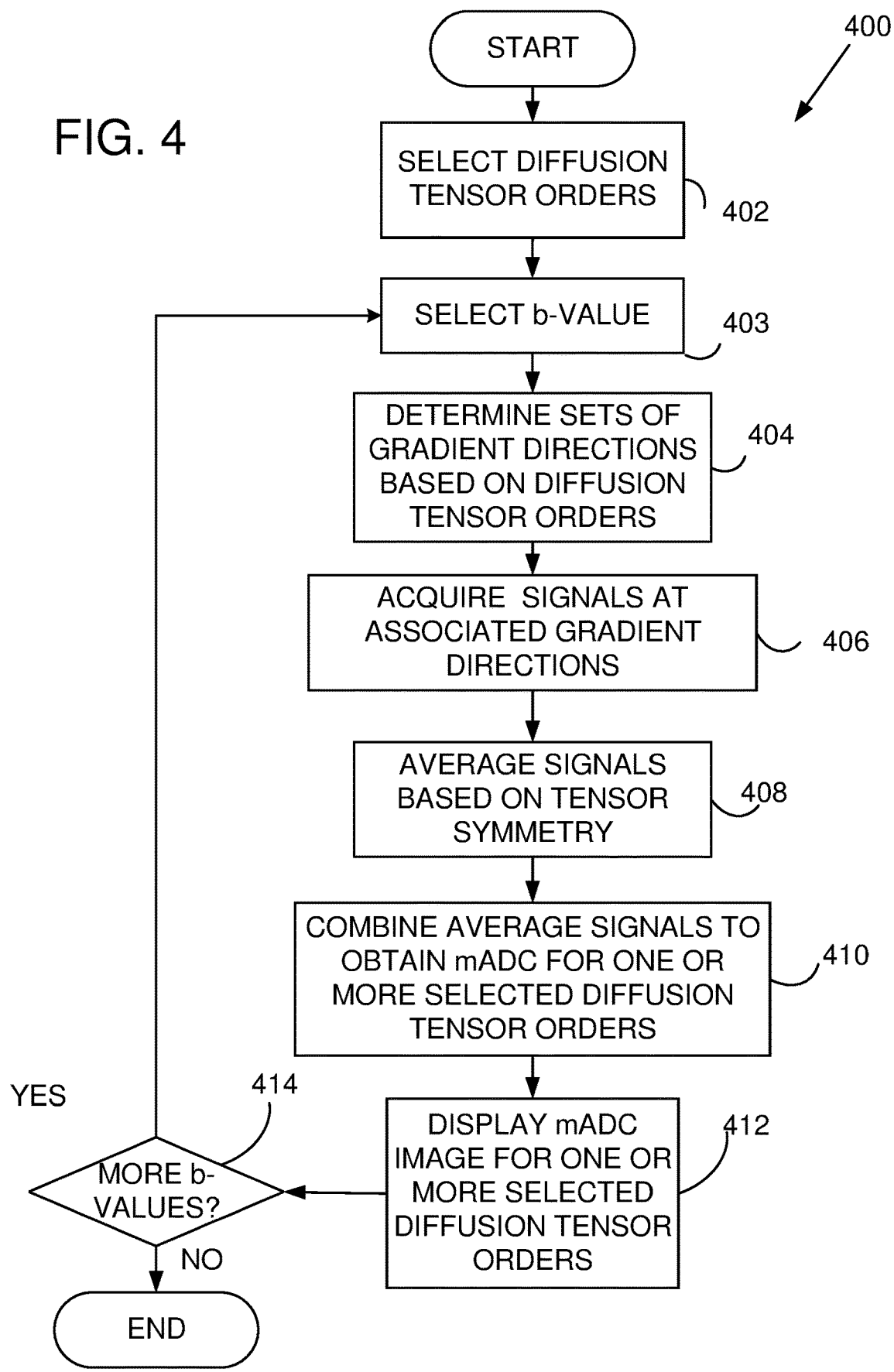
FIG. 4 illustrates a representative method of acquiring MR signal attenuations suitable for IGDTI.

Referring to FIG. 4, a method 400 includes selecting one or more diffusion tensor orders at 402. Alternatively, data associated with various orders can be collected and processed as needed later. At 403, a b-value is selected, in some cases, from a set of b-values, and at 404, sets of gradient directions are selected corresponding to the HOTs of interest. At 406, signals are acquired for the selected gradient directions and at 408, the signals within set are averaged as shown in Table 2 based on selected HOT symmetry. At 410, the averaged signals are combined by, for example, solving linear equations such as shown in Table 3, so as to obtain a diffusion related parameter such as one or more mADCs or Traces associated with corresponding HOTs. At 412, images associated with selected HOT orders can be displayed. In some cases, mADCs associated with each voxel in a specimen region are computed and used to form a displayed image. Other specimen characteristics such a mean kurtosis, standard deviation of mADCs, or others can be used in displayed images as well. If additional b-values are to be used as determined at 414, a b-value is again selected as 403 to acquire additional data. While FIG. 4 illustrates acquisition of images for all gradient directions at a single b-value before changing b-value, b-values and gradient directions can be selected arbitrarily and images need not be acquired in any particular order. From multiple mADC-weighted (i.e., orientationally-averaged) measurements over a wide range of b-values a spectrum of orientationally-averaged diffusivities in each voxel can be computed. The spatial-spectral diffusivity data can be visualized efficiently by displaying the cumulative distribution functions (CDF) derived from the diffusivity spectra or probability density function (PDF) in each voxel. The normalized spectra can be averaged over a certain region of interest to estimate tissue-specific orientationally-averaged diffusivity spectra (e.g., in normal appearing white matter, in gray matter, in a tumor, or in a brain lesion). Using tissue-specific orientationally-averaged diffusivity spectra known a priori (estimated from an atlas derived from a healthy or patient population, or estimated from an average over a region-of-interest (ROI) in a single subject—i.e., internal control) the diffusivity spectra in each voxel can be decomposed into tissue signal fractions to discriminate and visualize intra-voxel signal components associated with specific tissue types based on the water mobility properties within each tissue type.

REPRESENTATIVE EXAMPLES

In the following, some examples and aspects of the disclosed technology are illustrated with referenced to both ex vivo and in vivo imaging. However, signals can be obtained for a single ROI if desired, and mADCs and similar sample values obtained.

Example 1. Fixed Ferret Brain Data

A brain specimen from an adult male ferret was prepared for ex vivo MRI scanning following cardiac perfusion. The animal was housed and treated according to national guidelines and an approved institutional review board (IRB) protocol. On the day of perfusion the animal was deeply anesthetized by isoflurane inhalation (5% in oxygen) and euthanized with an intraperitoneal overdose of Euthasol (50 mg/kg). Upon cessation of reflexes, the ferret was transcardially perfused with 1 L of ice-cold phosphate buffered saline (PBS) (pH 7.4) followed by 1L of 4% paraformaldehyde solution in PBS (Santa Cruz Biotechnology) containing 47.6 mg of heparin (Sigma-Aldrich). The brain was harvested, post-fixed in 4% paraformaldehyde for 8-10 days, and then transferred to a storage solution containing 0.03% sodium azide in PBS (PBS-NaN$_3$). Following over one month of rehydration in this solution, the specimen was immersed in Fluorinert (FC-3283, 3M, St. Paul, Minn.) in a 25 mm glass NMR tube for imaging.

The ferret brain specimen was imaged using a 7T Bruker vertical bore micro-imaging scanner with a 25 mm linear RF coil. A 3D multi-slice, multi-echo (MSME) pulse sequence was used with TE/TR=30/3000 ms, with the following spatial parameters: FOV=26×40×20 mm$^3$, matrix=104× 160×80 for isotropic voxel dimension of 250 μm$^3$. A large GDTI data set containing 278 brain volumes was acquired with multiple b-values: b=500, 1500, 3000, 4500, 8000, and 13500 s/mm$^2$, and 4, 19, 25, 61, 74, and 95 directions, respectively, uniformly sampling the unit sphere at each b-value. To compute orientation-averaged DWIs efficiently a separate IGDTI data set at 5 b-values b=1500, 3000, 4500, 8000, and 13500 s/mm$^2$ was acquired using the efficient gradient sampling schemes in Table 3, with 3, 3+4, 3+4, 3+4+6, 3+4+6 orientations, respectively. Finally, to assess the rotation-invariance of the proposed method the aforementioned IGDTI experiment was repeated by rotating all gradient sampling orientations using a 3D rotation matrix R=R$_y$(54.74°)R$_z$(45°) composed of rotations along the y and z axes by 54.74° (magic angle) and 45° respectively. All DWIs were collected with the same spatial geometry and dimensions as the MSME scan, using a 3D EPI pulse sequence with TE/TR=36/700 ms, NEX=1, 8 segments and 1 repetition and diffusion weighting parameters of $\delta$=3.2 ms and $\Delta$=20 ms.

Example 2. In Vivo Human Data

A healthy volunteer was scanned on a clinical Siemens Prisma 3T MRI scanner, equipped with a maximum gradient strength of 8 G/cm/axis using a 32 channel RF coil under an approved clinical protocol. Using a conventional single-shot spin-echo diffusion EPI clinical pulse sequence, several series of MRI scans with different diffusion gradient sampling schemes but the same imaging parameters were collected. Whole brain DWIs were acquired with $\delta$=34.6 ms and $\Delta$=40.2 ms, a 21 cm field-of-view (FOV), an in-plane resolution of 2.5 mm, a 5 mm slice thickness, and TE/TR=93/7000 ms. The GDTI data set contained 7 baseline images and 278 DWIs with multiple b-values=500, 1000, 1700, 2500, 4000, and 6000 s/mm$^2$, and 4, 19, 25, 61, 74, and 95 orientations, respectively, uniformly sampling the unit sphere at each b-value. In addition, an IGDTI data set was acquired (2 averages) with b=1000, 2500, and 6000 s/mm$^2$ using the efficient gradient sampling schemes in Table 2, with 3, 3+4, 3+4+6 orientations, respectively, to achieve isotropic HOT weighting up to orders 2, 4 and 6, respectively. To assess the rotational invariance of IGDTI this experiment was repeated with rotated gradient sampling schemes. Finally, in a short clinical IGDTI scan using the 3+4+6 gradient design for high b-values (Table 3), mADC was measured with b=8500s/mm$^2$ and the same imaging parameters as above, except TE=100 ms.

Example 3. Post-Processing and Data Analysis

All fixed-brain and clinical diffusion MRI data discussed above were processed using the TORTOISE software package (Pierpaoli et al., "TORTOISE: an integrated software package for processing of diffusion MRI data," Stockholm, Sweden. p 159 (2010)) to register DWI volumes resampled to isotropic resolution (250 µm and 2.5 mm, respectively) and to remove potential distortions due to eddy currents and other sources of magnetic field inhomogeneities. The analysis of GDTI and IGDTI data sets was identical for both micro MRI and clinical MRI experiments. To derive orientationally-averaged DWIs and measure the mADCs at each b-value in the GDTI averaging approach, the log signal attenuations were obtained with dense gradient orientations uniformly sampling the unit sphere. In addition, the HOTs were measured by fitting the densely sampled GDTI data sets to Eq. 3 and the HOT Traces and generalized mean diffusivities $\overline{D^{(n)}}$ computed up to order 6 using Eq. 6, and subsequently, the mean t-kurtosis using Eq. 9. From the IGDTI data sets, the orientation-averaged DWIs and mADCs at each diffusion sensitization were computed using the linear combinations of log signal attenuations described in Table 2 for the corresponding b-value range, and the results compared with the corresponding images derived from the GDTI data. Subsequently, the HOT Traces TrD$^{(n)}$, and generalized mean diffusivities $\overline{D^{(n)}}$ for n=2, 4, and 6 were computed by fitting the IGDTIs to the polynomial equations in Table 2, and the results compared to those obtained by directly measuring the HOTs with GDTI. The same analysis was applied to the IGDTI data sets acquired with rotated gradient sampling schemes and the results were compared to those of the original sampling scheme (Table 2) to assess the rotation invariance of IGDTI. Finally, from the IGDTI-derived generalized mean diffusivities $\overline{D^{(n)}}$ of order 2 and 4, the mean t-kurtosis was computed using Eq. 9, and the results compared to those obtained from the GDTI analysis.

Example 4. Precision, Accuracy, and Rotation-Invariance

Numerical simulations were conducted to assess the precision, accuracy, and rotation-invariance of estimated microstructural parameters using IGDTI. From the HOT components measured in vivo using GDTI analysis (from 278 DWIs) ground-truth values for TrD$^{(n)}$ and $\overline{W}$ were derived and DWI signals expected for the proposed gradient sampling scheme using 3, 3+4, and 3+4+6 gradient orientations at b-values 1000 s/mm$^2$, 2500 s/mm$^2$, and 6000 s/mm$^2$, respectively, were generated. Gaussian noise was added to the real and imaginary channels to simulate different signal-to-noise ratios (SNR) from 10 to 100 in increments of 10, and the mean and standard deviation of the estimated microstructural parameters TrD$^{(n)}$ and $\overline{W}$ obtained from 200 independent instances of noisy measurements were computed. Accuracy was calculated as the absolute error of the mean with respect to the ground-truth value and the precision as the standard deviation. To quantitatively assess the rotation invariance of IGDTI-based measurement of microstructural tissue parameters, from ground-truth HOT values. DWI signals were generated with SNR=70 using the proposed gradient sampling scheme re-oriented with 256 different rotations R=$R_x(X)R_y(Y)R_z(0°)$, wherein Euler angles X, and Y were varied independently between ~45° and 45° in 16 steps. Finally, the means and standard deviations of the microstructural parameters TrD$^{(n)}$ and $\overline{W}$, calculated with different rotations of the gradient sampling scheme were quantified.

Example 5. Sample Results

Figure 5:
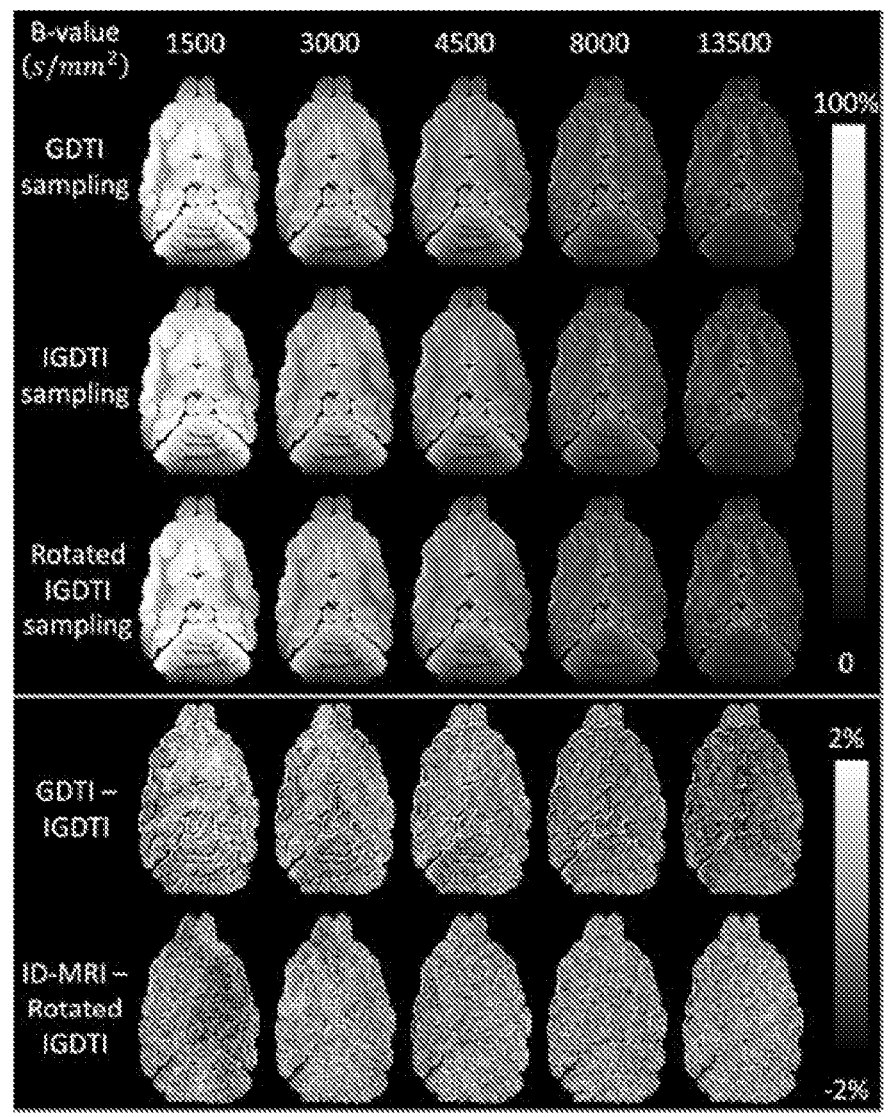
FIG. 5 includes orientationally-averaged (i.e., mADC-weighted) DWIs of a ferret brain specimen at five different b-values generated from a GDTI data set with dense and uniform angular sampling at each b-value, IGDTI using the efficient gradient sampling schemes in FIG. 1 and Table 1, and IGDTI using a rotated gradient sampling scheme. The small values in the difference images, on the order of 2%, demonstrate the rotation-invariance and high accuracy of IGDTI in eliminating the effects of diffusion anisotropy and generating isotropic diffusion measurements over a wide range of b-values.
Figure 6:
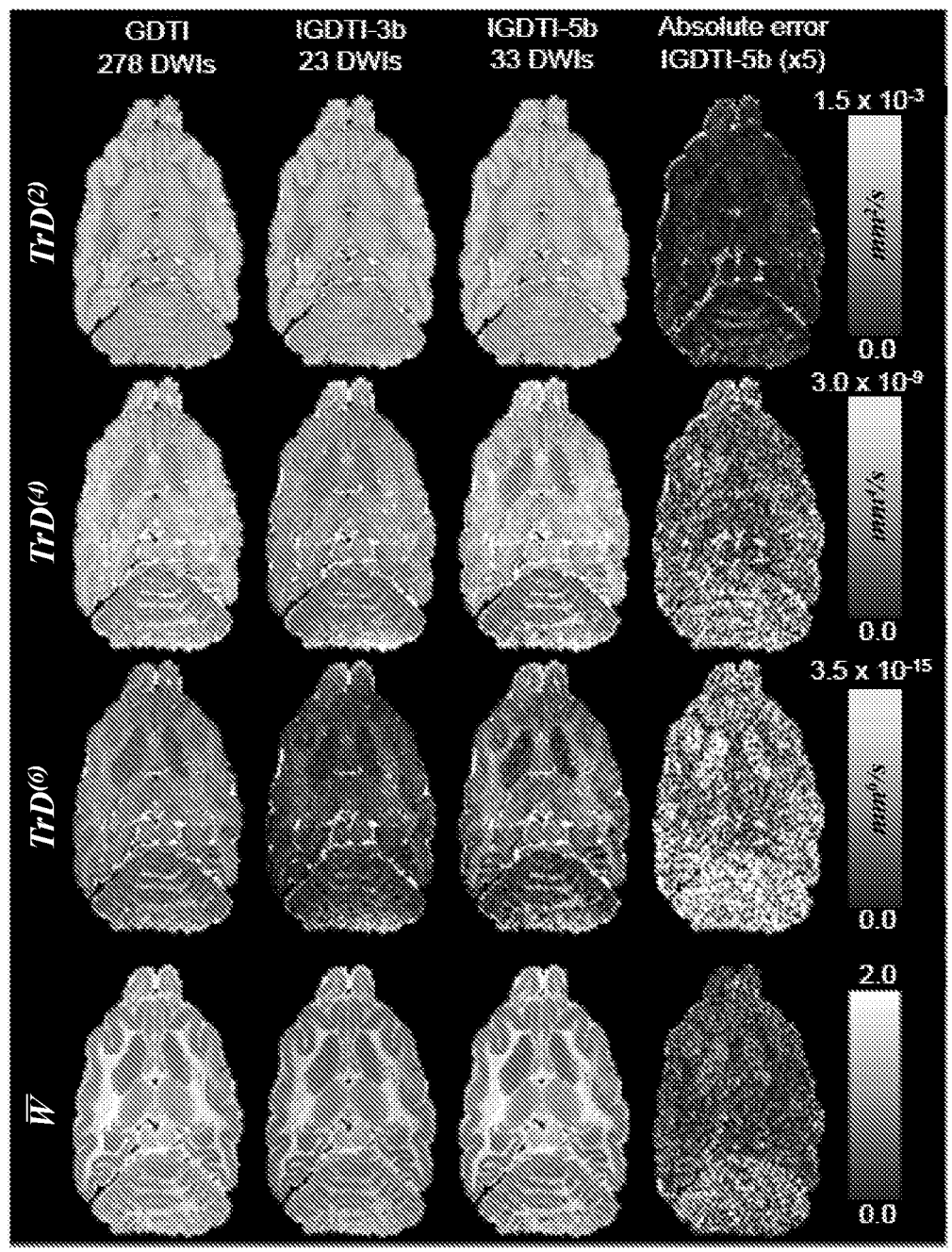
FIG. 6 illustrates images based on traces of diffusion tensors, $TrD^{(n)}$ for orders 2, 4, and 6, and mean t-kurtosis $\overline{W}$ in a fixed ferret brain measured with GDTI, IGDTI with 3 b-values, and IGDTI with 5 b-values. The difference images illustrate the ability of IGDTI to efficiently quantify rotation-invariant HOT diffusion parameters in fixed-brain tissues. A larger number of b-values improves the stability of measuring these parameters with IGDTI.

The accuracy and degree of rotation invariance of IGDTI measured over a large range of b-values is satisfactorily demonstrated in FIG. 5 using data from a ferret brain specimen. Orientationally-averaged (i.e., mADC-weighted) DWIs measured with IGDTI are remarkably consistent with those derived from densely sampled data sets with significantly finer angular resolution, and show virtually no distinguishable anatomical features in difference maps. The same level of agreement can be observed between IGDTI mADC-weighted DWIs acquired with rotated sampling schemes, confirming the rotation invariance of IGDTI in quantifying isotropic bulk diffusion signals in brain tissues. FIG. 6 shows images associated with HOTs obtained using GDTI and IGDTI at several b-values and associated error images.

Figure 7:
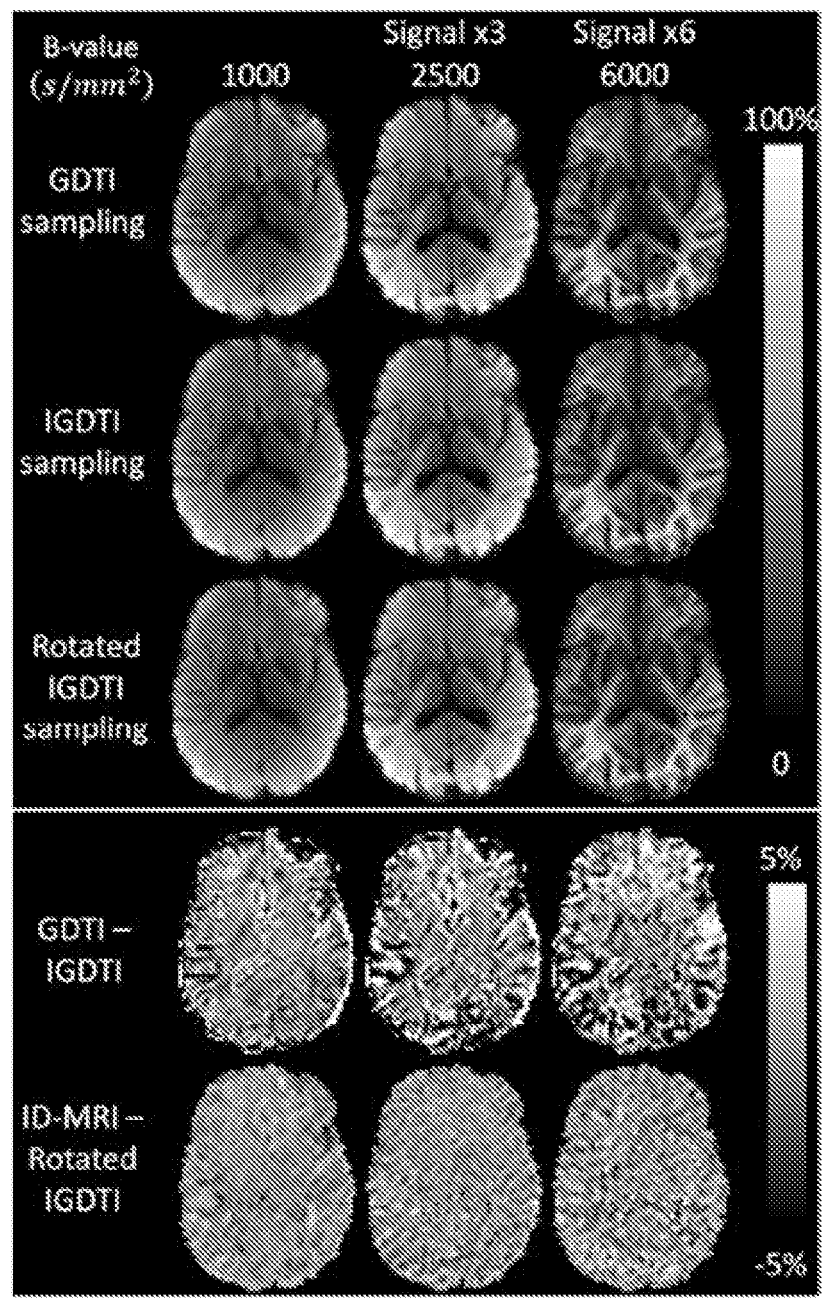
FIG. 7 illustrates orientationally-averaged (i.e., mADC-weighted) DWIs in clinical MRI scans at three different b-values generated from a GDTI data set with dense and uniform sampling at each b-value and IGDTI using the efficient gradient sampling schemes in FIG. 1 and Table 1, and IGDTI using a rotated gradient sampling scheme. The small values in the difference images in brain tissue regions illustrate the high accuracy and rotation-invariance of IGDTI in eliminating the effects of diffusion anisotropy and generating isotropic diffusion measurements over a wide range of b-values in clinical applications. Note that both DWIs and difference images for b=2500 and 6000 s/mm$^2$ are scaled by factors of 3, and 6 respectively to improve conspicuity.
Figure 8:
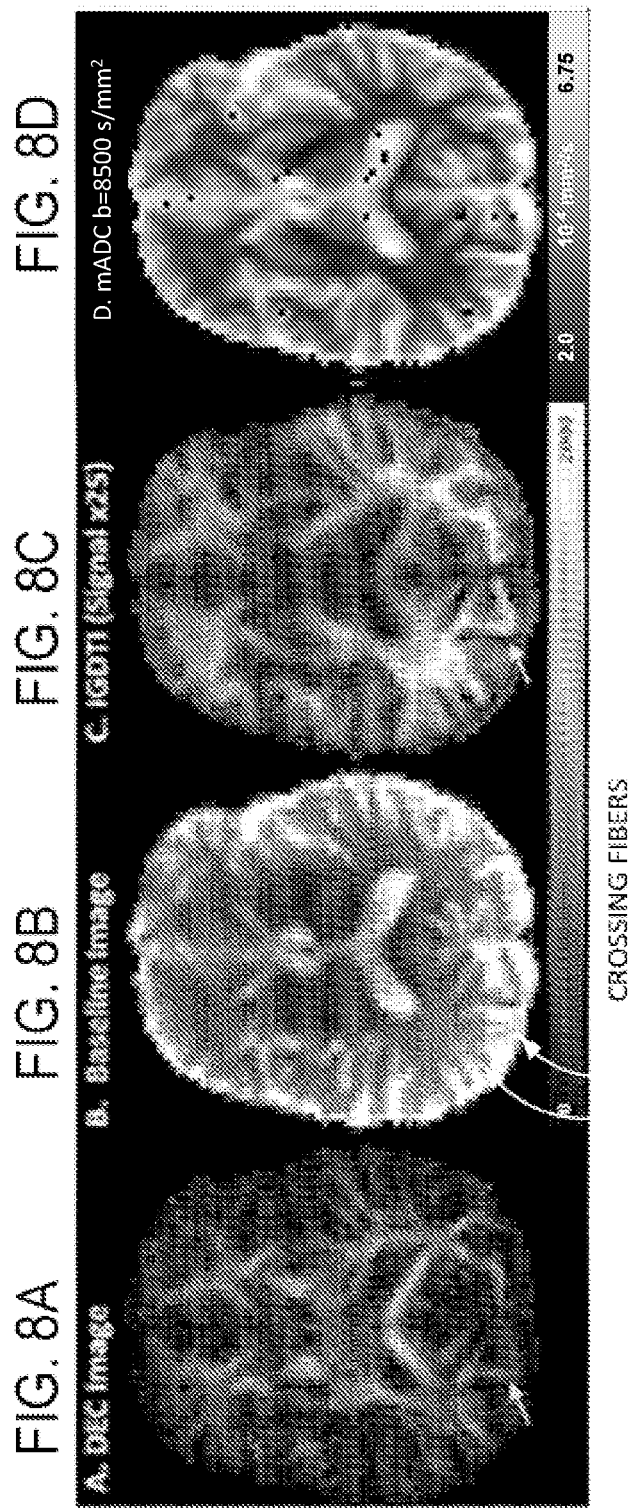
FIGS. 8A-8D illustrate tissue contrast at high diffusion sensitization measured efficiently with IGDTI acquired in less than 2 minutes.

The accuracy and rotation invariance of the IGDTI mADC-weighted measurements were replicated in the clinical MRI experiments (FIG. 7). Compared to the fixed brain results in FIG. 5, slightly larger differences between orientation-averaged signals measured with GDTI and IGDTI occurred primarily at tissue boundaries and may be due to subject motion between the two acquisitions. The clinical potential of IGDTI is best illustrated with measurements obtained at very high b-values (FIGS. 8A-8D) in under two minutes. The in vivo mADC-weighted IGDTI signal at b=8500 s/mm$^2$ reveals a tissue contrast that resembles the fractional anisotropy (FA) modulating the direction-encoded colored (DEC) map but may be less affected by architectural features of the tissue, such as crossing white matter pathways. At the same time, the mADC measured at high b-value (FIG. 8D) shows improved contrast around the putamen and globus pallidus compared to the $T_2$-weighted (i.e., non-diffusion weighted) image (FIG. 8B).

Figure 9:
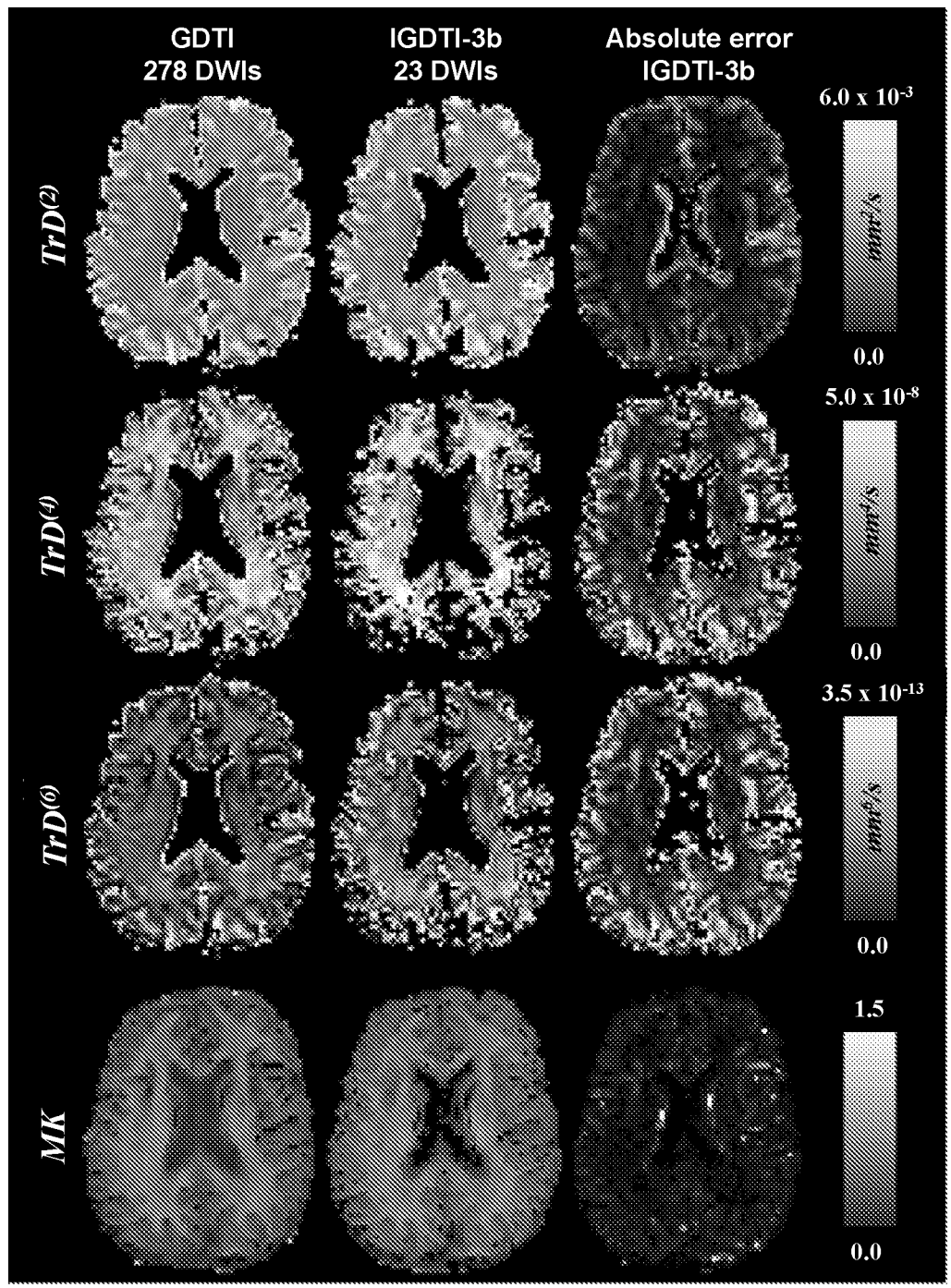
FIG. 9 shows images that permit comparison of Traces of diffusion tensors, $TrD^{(n)}$ for orders 2, 4, and 6, and mean t-kurtosis (MK) $\overline{W}$ measured in vivo with GDTI and IGDTI with 3 b-values showing the ability of IGDTI to quantify rotation-invariant HOT-derived diffusion parameters in brain tissue within a clinically feasible scan duration.

As shown in FIG. 9, $TrD^{(n)}$ and $\overline{W}$ measured with IGDTI in clinically feasible scan durations and with GDTI show good agreement especially in brain tissue regions that are not affected by partial volume contamination with cerebrospinal fluid (CSF) and which are therefore less prone to quantitation errors due to subject motion. The relatively high apparent $TrD^{(4)}$ and $TrD^{(6)}$ measured in vivo in the CSF are likely biased by low SNR in high b-value DWIs as well as CSF partial volume contributions at the tissue interface. Biases in the estimated HOT parameters due to the noise floor (caused by rectified Gaussian noise in both real and imaginary RF receive channels) may be mitigated with the use of regularization methods. Meanwhile biases due to partial volume contributions owing to having different tissue types and compartments occupying the same voxel) may use higher-order corrections to the signal model or water elimination.

Figure 10:
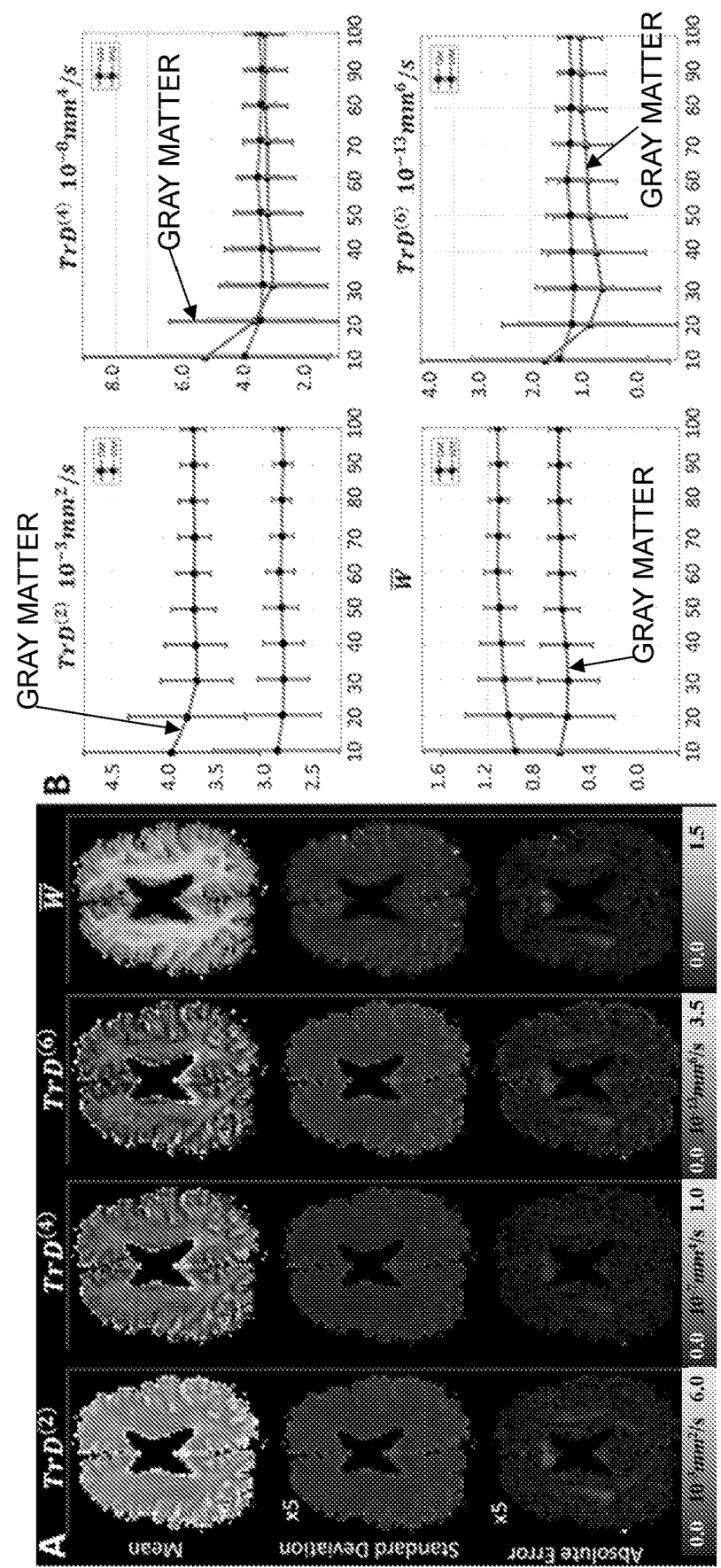
FIG. 10 illustrates numerical simulations of signal-to-noise ratio (SNR) dependence of tissue parameters $TrD^{(n)}$ and $\overline{W}$ estimated using efficient IGDTI sampling schemes.

The numerical simulations results in FIG. 10 show that biases in the estimation of $TrD^{(n)}$ and $\overline{W}$ using the sampling schemes in experiments are expected for SNR levels <50. For SNR levels higher than 50, the precision of the estimated parameters improves with increasing SNR. For the in vivo experiment, the ("temporal") SNR level in white matter ranged between 60-75, as computed from six b=0 s/mm² images acquired throughout the duration of the experiment. Estimates of the microstructural parameters $TrD^{(n)}$ and $\overline{W}$ show little dependence on the orientation of the gradient sampling scheme, which is in agreement with the empirical results (FIGS. 6 and 9). However, increasing orientational sampling at lower b-values may improve the both the accuracy and the rotation-invariance of these estimated parameters.

Errors in the quantitation of diffusion properties may arise from several sources:
1. Inaccurate DWI registration and correction for distortions due to magnetic field inhomogeneities and gradient-induced eddy currents. These errors are more difficult to correct in DWIs acquired with high b-values.
2. Contributions to the diffusion-encoding gradient field due to gradient eddy currents, concomitant fields, gradient non-linearities, as well as from background field gradients in tissue, imaging gradients and magnetic field inhomogeneities. These errors in quantifying the effective diffusion sensitization (b-value) may bias the estimates of higher-order diffusion tensor components, in particular.
3. Physiological and subject motion during in vivo experiments, which may require reorientation of the applied diffusion gradients while performing data analysis.

These errors are especially problematic in long scans. Discrepancies between microstructural parameters estimated with GDTI and IGDTI (FIGS. 6 and 9) may also be attributed to: 1) Increased effective SNR in the GDTI data set due to the larger number of DWIs, 2) restricted diffusion, partial volume and/or noise floor effects along any particular diffusion orientation that may require higher order truncations of the cumulant expansion at high b-values. Asymmetric diffusion (e.g., due to flow or diffusion in asymmetric pores at short diffusion times) violating the assumption that only even order HOTs contribute to the diffusion signal expansion in Eq. 3.

As shown above, these results indicate that, given the sensitivities of micro-imaging and clinical experiments, the effects of bulk anisotropy on the MR diffusion signal in tissue can be eliminated using a $6^{th}$-order tensor model even at high diffusion sensitizations. Nevertheless, for a given experiment, the IGDTI sampling scheme should preferably be chosen based on both the desired diffusion sensitization (b-value) and the expected average water mobility in the sample. These experiments confirmed the expected lower tissue water mobility in fixed-brain compared favorably to in vivo experiments. This difference in diffusivities is consistent with the literature and may be attributed to: 1) microstructural alterations (e.g., cell shrinkage) in the presence of fixation agents; 2) lower sample temperature (room vs. body), and 3) absence of any physiological active or passive transport mechanisms (e.g., owing to cell death) in fixed tissue. The b-value ranges for micro-imaging and clinical experiments suggested in Table 2 are based on the aforementioned considerations.

Example 6. Summary of Selected Example IGDTI Results

IGDTI measures orientationally-averaged diffusion signals over a wide range of b-values by matching the weightings of all HOT elements in Eq. 6. This is achieved by: 1) generating weightings, such as $M_3(b)$, $M_4(b)$, and $M_6(b)$, with similar symmetry properties (Conditions 1 and 2) as the Trace-Weighting in Eq. 6, and 2) forming linear combinations from these weightings to match the weightings for all HOT components in Eq. 6 up to a certain order. Consequently, the gradient sampling scheme design can be analytically related to the complexity of the underlying diffusion signals as described by higher order Cartesian tensors. This strategy yields very efficient solutions for achieving rotation-invariant diffusion weighting and generalizes several classic diffusion gradient sampling schemes.

IGDTI does not capture all orientational information in the diffusion signal. Rather, using efficient sampling schemes (with 3, 7 and 13 DWIs), it elegantly removes the effect of diffusion anisotropy based on the complexity of the underlying diffusion signal (as modeled by HOT models of order 2, 4, and 6, respectively), which usually increases with b-value and tissue diffusivity (Table 2). In general, denser angular sampling is required to capture all orientational information at high b-values.

A theoretical minimum number of sampling orientations required to obtain orientationally-averaged DWIs (assuming a fully symmetric rank-n HOT signal model) can be estimated based on the number of unique tensor elements $D_{n_x n_y n_z}^{(n)}$ ($n_x$, $n_y$, $n_z$ all even) with non-zero weighting (i.e., number of degrees of freedom) in the expression of the generalized Trace, $TrD^{(n)}$. For a b-value at which the diffusion signal is described by a rank-n HOT model, a minimum number of $$\frac{\left(\frac{n}{2}+1\right)\left(\frac{n}{2}+2\right)}{2}$$

orientations is generally needed to obtain a rotation-invariant DWI. Removing modulations due to anisotropy in signals described with order-2, -4, and -6 HOT models requires at least 3, 6, and 10 DWIs, respectively; while computing rotation-invariant microstructural parameters derived from HOT models of order-4 (such as $TrD^{(4)}$ and $\overline{W}$) and order-6 (such as $TrD^{(6)}$) requires at least 3+6=9 DWIs and 3+6+9=19 DWIs, respectively, in addition to one baseline image. Approximate gradient sampling schemes using the theoretical minimum number of orientations to remove anisotropy may be obtained with numerical methods.

While the representative measurements of $TrD^{(4)}$ and $\overline{W}$ shown in FIGS. 6 and 9 illustrate how IGDTI sampling schemes may be used to estimate HOT-derived parameters, particular number of b-values and gradient orientations can be selected for clinical diffusion MRL applications, such as fast diffusion kurtosis imaging (DKI) mean apparent propagator (MAP) MRI, and clinical applications such as isotropic diffusion relaxometry imaging at the whole brain level.

IGDTI gradient sampling schemes can provide orientationally-averaged measurements over a wide range of b-values, which can serve in various applications, such as estimating $TrD^{(n)}$ and $\overline{W}$. The parameter $\overline{W}$ defined in Hansen et al., "Experimentally and computationally fast method for estimation of mean kurtosis," Magn. Res. Med. 69(6):1754-1760 (2013), which is incorporated herein by reference, represents an approximation to the mean kurtosis (MK) and can be measured from two orientationally-averaged DWIs without the need to explicitly compute an entire kurtosis tensor W. As detailed in Mathematical Supplement B, for fully symmetric diffusion, the definition of W can be generalized with respect to the HOTs $D^{(n)}$ to define the dimensionless rank-n tensor $$W^{(n)} = \frac{n! \overline{D^{(n)}} \left( \Delta - \frac{(n-1)}{(n+1)} \delta \right)}{2^{\frac{n}{2}} \overline{D^{(2)}}^{\frac{n}{2}} \left( \Delta - \frac{\delta}{3} \right)^{\frac{n}{2}}} \quad (10)$$

The mean of tensor $W^{(n)}$, $\overline{W^{(n)}}$, is directly related to the mean of $D^{(n)}$, and implicitly to the generalized Trace, $TrD^{(n)}$. Images of $\overline{W^{(6)}}$ derived from both fixed-brain and clinical data sets can reveal significantly larger contrast compared to $\overline{W^{(4)}} = \overline{W}$.

In the examples discussed above, conventional spin-echo diffusion MRI sequences were used without accounting for the ramp durations of the applied diffusion gradient pulses. IGDTI sampling schemes can be extended to spin echo diffusion preparations with arbitrary gradient pulse shapes, including trapezoids with finite ramps, twice-refocused spin echo, or oscillating diffusion gradient pulses. The temporal characteristics scale $\beta_n$ in Eqs. 3 and 5, but do not affect the orientational averaging in Eq. 4.

Clinical assessment of orientationally-averaged bulk water diffusion properties in tissues could be further accelerated using advanced diffusion preparation methods. As discussed above, a selected gradient direction and its opposite produce a common diffusion sensitization. But in other examples, a series of bipolar diffusion gradient pairs with orientations given by Scheme 2 can be applied so as to cancel contributions from selected tensor elements. Such preparation can be adapted with the bipolar gradient pairs applied along the orientations in Schemes 1 and 3, and extended to larger b-values, yielding estimates of $M_3(b)$, $M_4(b)$, and $M_6(b)$ from single-shot measurements, and enabling computation of orientationally-averaged diffusion signals at high b-values from only 3 DWIs. Such single-shot preparations not only reduce the acquisition time leading to fewer quantitation errors and imaging artifacts in clinical scans, but also produce DWI signals having a smaller dynamic range due to the partial averaging of anisotropy (Eq. 8). This reduced dynamic range extends the quality of orientationally-averaged signals in anisotropic tissues to even higher b-values that are otherwise unobservable with conventional techniques due to the signal reaching the noise floor along particular directions where the diffusivity may be high.

Figure 11A:
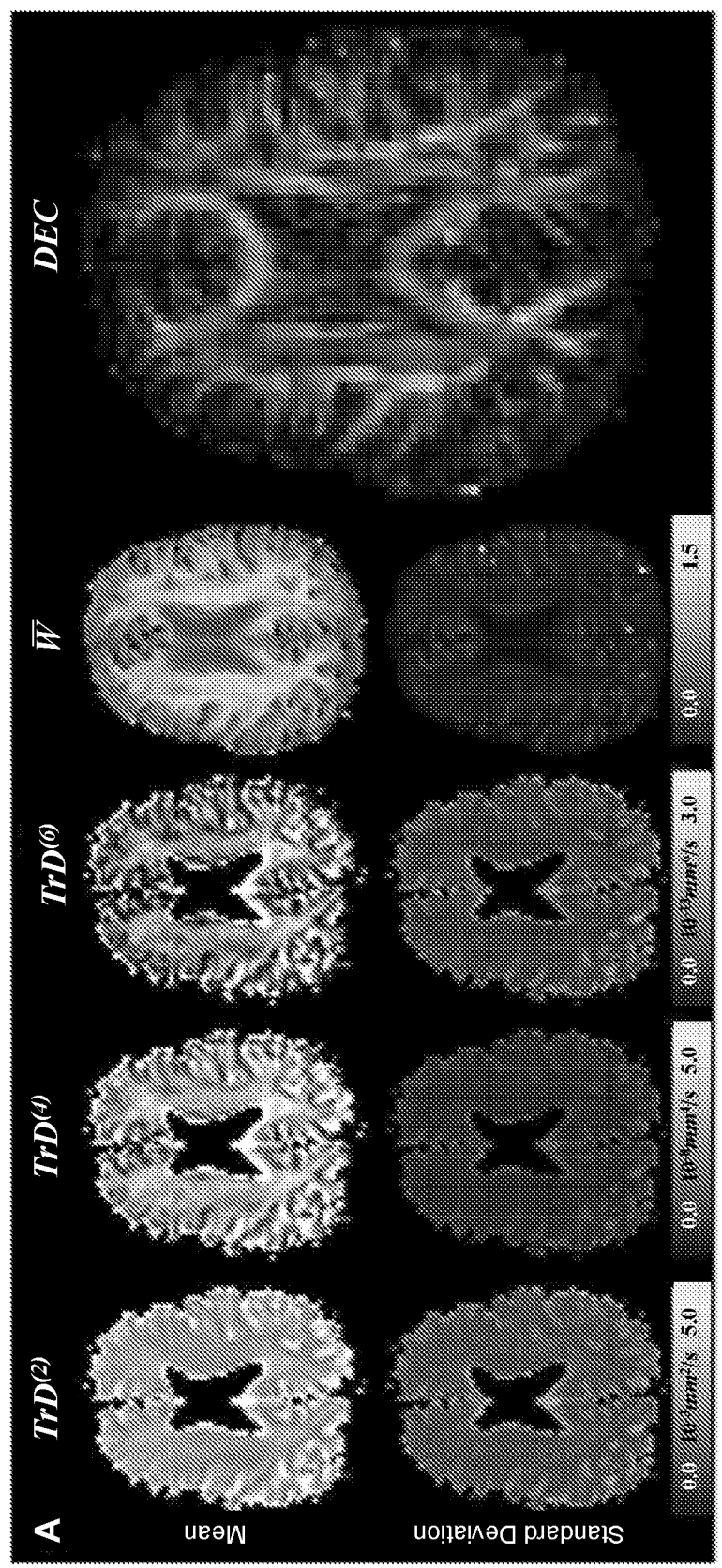
FIGS. 11A-11B illustrate numerical simulations of rotation invariance of tissue parameters $TrD^{(n)}$ and $\overline{W}$ estimated using efficient IGDTI sampling schemes. The computations assume an SNR=70 and estimate tissue parameters by reorienting the gradient sampling scheme with 256 different.
Figure 11B:
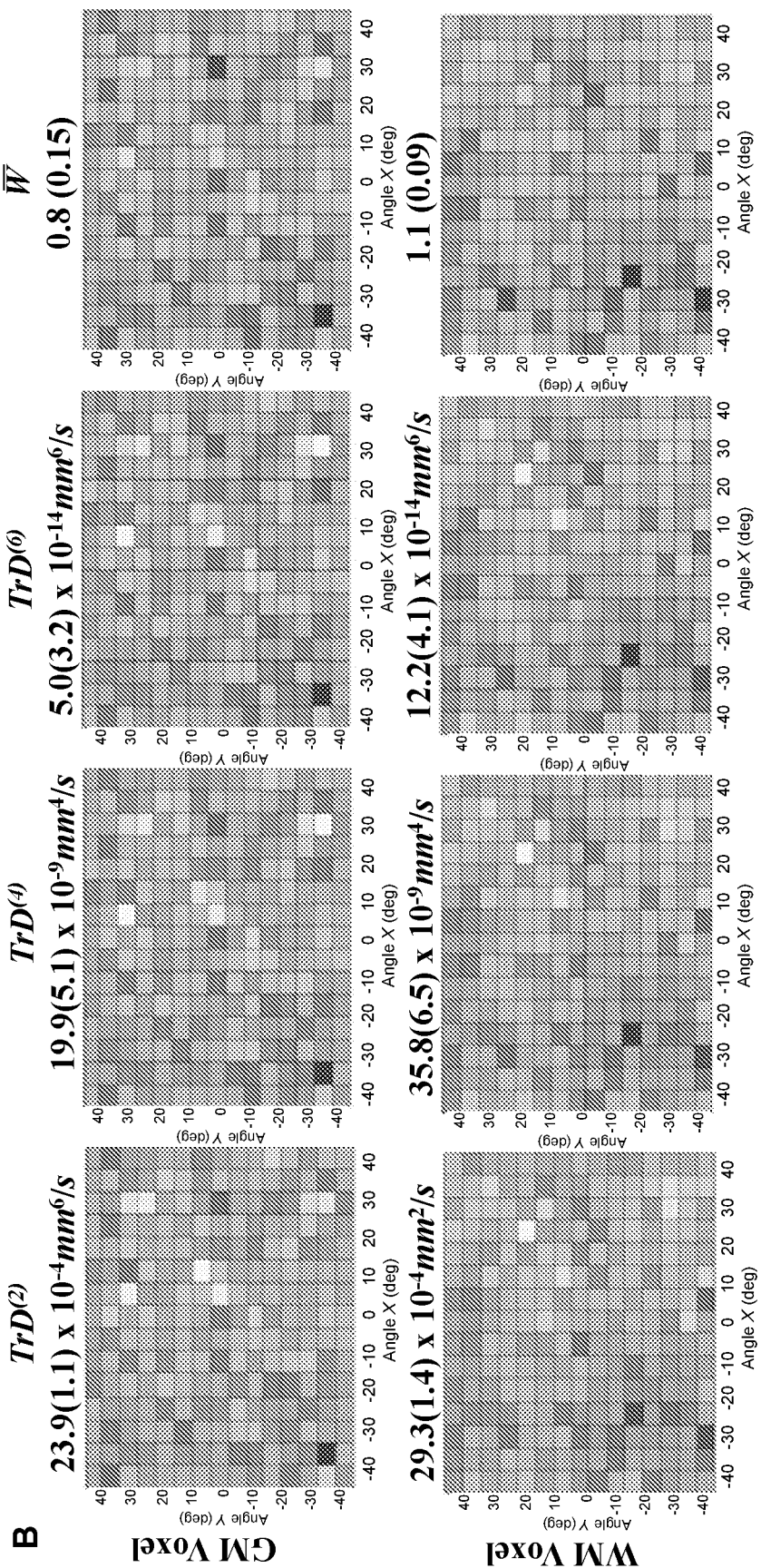

FIGS. 11A-11B illustrate numerical simulation of rotation invariance of tissue parameters $TrD^{(n)}$ and $\overline{W}$ estimated using efficient IGDTI sampling schemes. The computations assume an SNR=70 and estimate tissue parameters by reorienting the gradient sampling scheme with 256 different rotations $R = R_X(X) R_Y(Y) R_Z(0°)$, where Euler angles X, and Y were varied between −45° and 45° in 16 steps. FIG. 11A shows mean and standard deviations of the measured parameters and FIG. 11B shows 256 values of the tissue parameters (means and standard deviations included) in representative GM and WM tissue voxels estimated using different rotations of the gradient sampling scheme.

Example 7. Isotropic Diffusion Relaxometry

Figure 12:
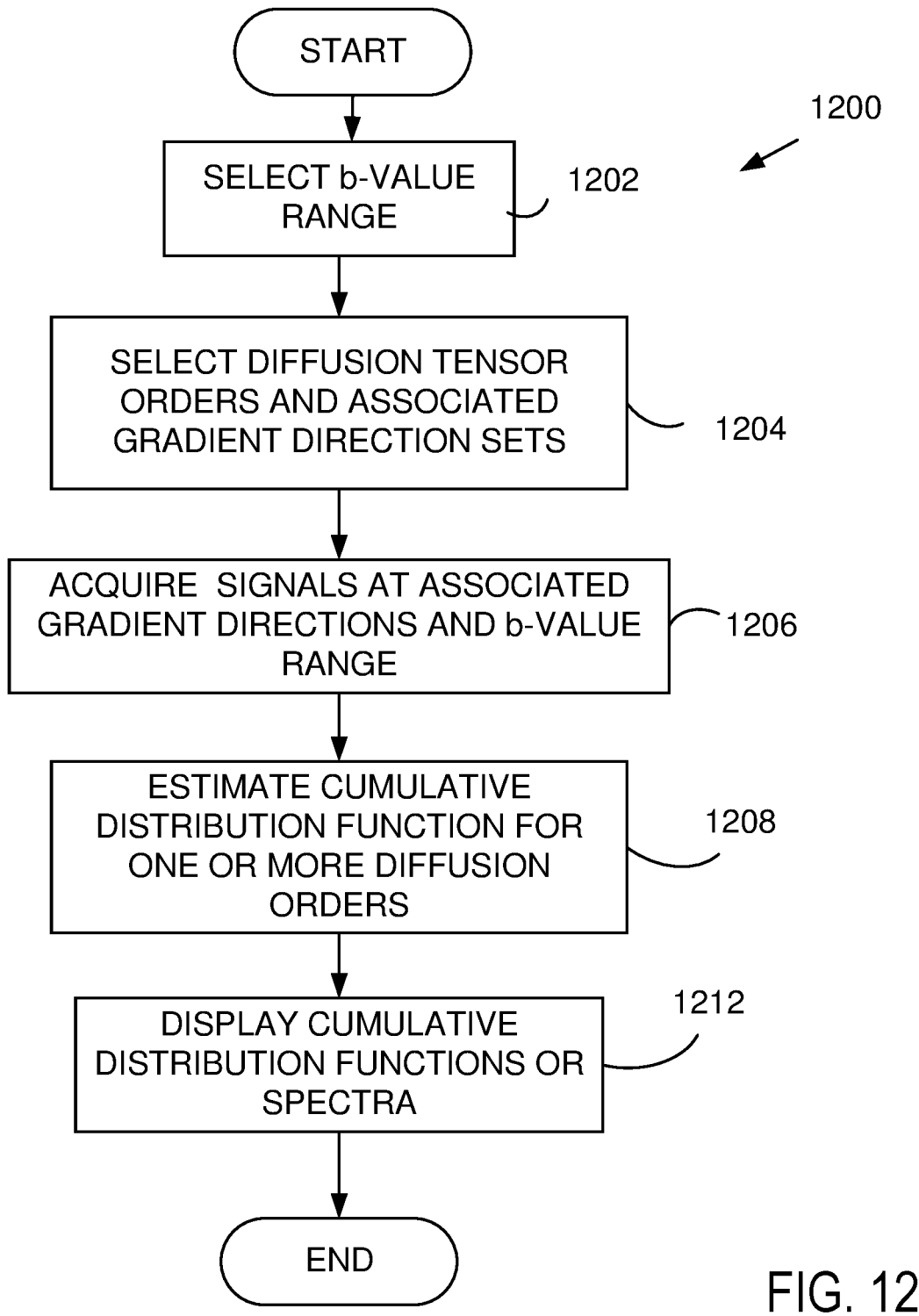
FIG. 12 illustrates a representative method of acquiring cumulative distribution functions (CDF) and spectra associated with higher-order diffusion tensors.

By obtaining mADCs associated with one or more HOTs at various b-values, associated diffusivity spectra can be obtained. Referring to FIG. 12, a method 1200 includes selecting a range of b-values at 1202 and one or more diffusion tensor orders along with associated gradient directions for IGDTI at 1204. The b-values can be selected to be in a suitable range for a particular specimen. DWIs are acquired at the plurality of b-values at 1206. For each voxel, a 1-D spectrum (i.e., probability density function) of intra-voxel diffusivities is computed at 1208 by, for example, solving the L-regularization problem with positivity constraints:

$$\arg \min_{p>0} \|Mp - s\|_2 + \lambda \|p\|_2,$$

wherein p is array of spectral/probability amplitudes as a function of diffusivity at a selected set of b-values, s is an array of isotropic (orientationally averaged) signal decay values at each of the selected set of b-values, and M is an encoding matrix that contains unknown spectral amplitudes as a series of discrete values:

$$M_{ij} = \int_{D_j - \Delta D}^{D_j + \Delta D} e^{-b_i D} dD.$$

In one example discussed below, 18 different b-values, with diffusion values ranging from 0.01 to 3600 mm²/s are used. The PDFs and cumulative distribution functions (CDFs) are displayed at 1212.

In some applications, diffusivity spectra can be determined for ROIs that include similar tissue types or other structures. For example, for brain MRI, ROIs associated with cerebrospinal fluid (CSF), white matter (WM), and gray matter (GM) are identified, and diffusivity spectra for each of these ROIs are estimated as $p_{CSF}$, $p_{WM}$, and $p_{GM}$, respectively. With such ROI diffusivity spectra, signal fractions in a DWI can be associated with suitable fractions of tissue types in these ROI as a set of three signal fractions, f, associated with $p_{CSF}$, $p_{WM}$, and $p_{GM}$. DWI data can be analyzed to compute such signal fractions based on solving:

$$\arg \min_{f>0} \|Tf - s\|_2,$$

where f contains the unknown signal fractions associated with each tissue component (in this example, $p_j$, where j is CSF, WM, or GM), and T is defined as, $$T_{ij} = \int_0^\infty e^{-b_i D} p_j(D) dD.$$

Figure 13:
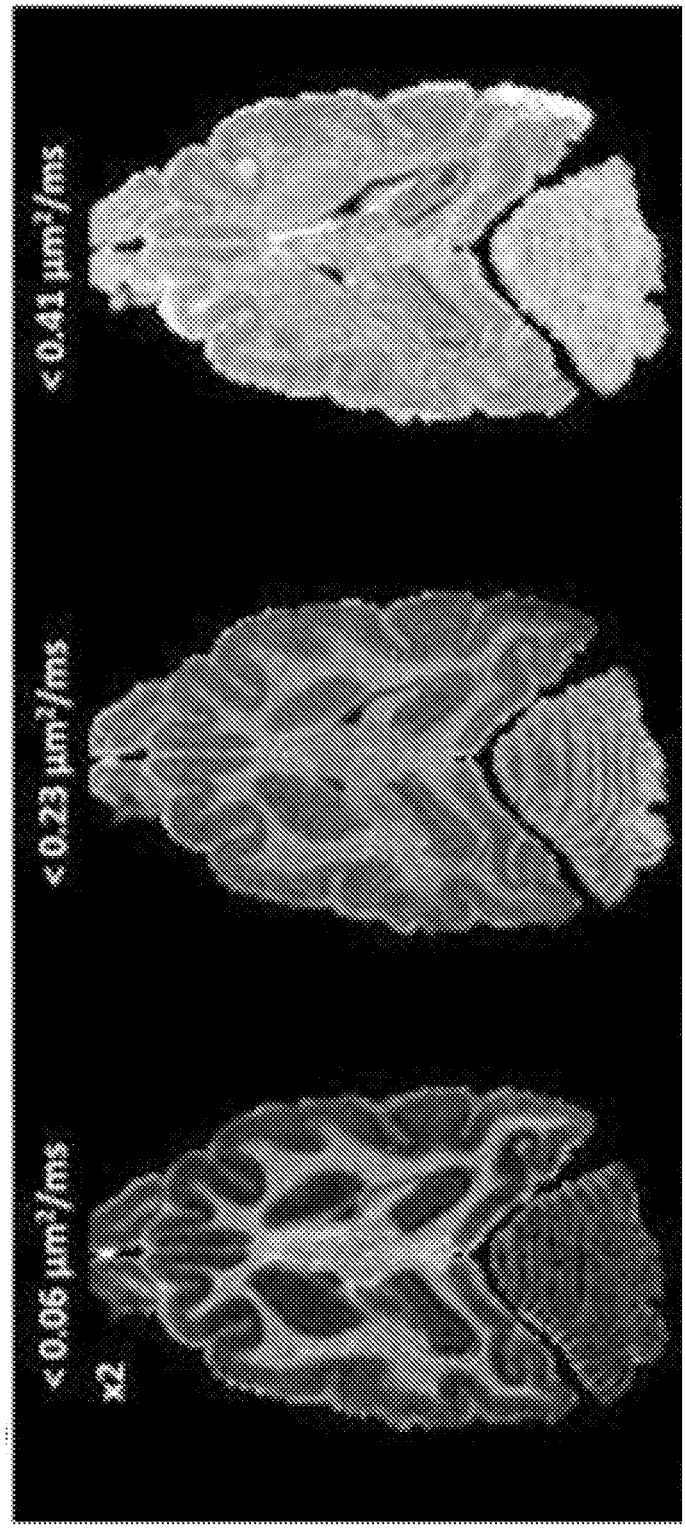
FIG. 13 illustrates CDF images of spectra of orientationally-averaged diffusivity (mADC) measured in fixed ferret brain.
Figure 15:
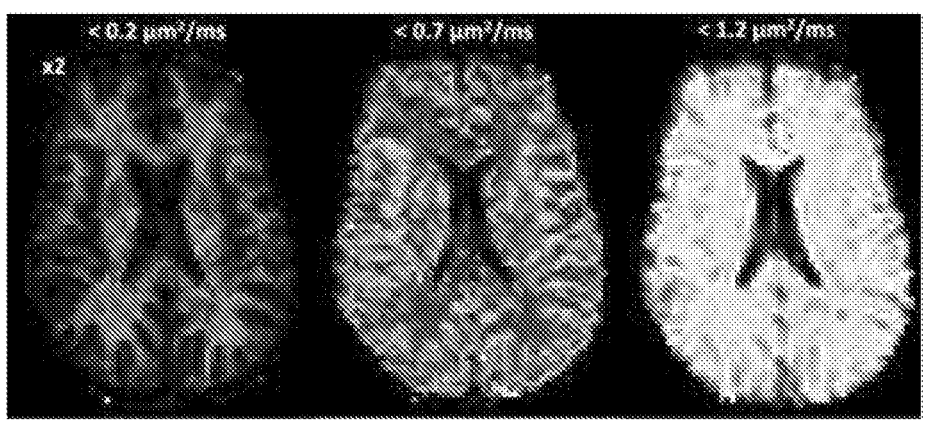
FIG. 15 illustrates CDF images or maps of spectra of orientationally-averaged diffusivity measured in live human brain.
Figure 16:
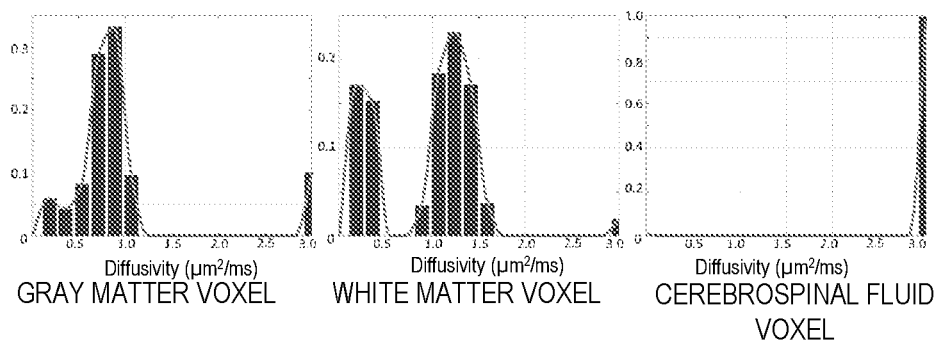
FIG. 16 illustrates fitted spectra associated with the images of FIG. 15. Peaks at 0.23 and 1.2 µm$^2$/ms are clearly discernible in the white matter spectrum.

Representative results are illustrated in FIGS. 13-16. FIG. 13 contains cumulative distribution function (CDF) images of spectra of orientationally-averaged diffusivity in fixed ferret brain (top row) in particular diffusivity ranges, and FIG. 14 shows fitted spectra p in three representative voxels containing gray matter, white matter, and mixed brain tissue corresponding to the images of FIG. 13. Two peaks at 0.015 and 0.035 μm²/ms are clearly discernible in the white matter spectrum. FIGS. 15-16 show corresponding CDF images or maps representing spectra in each voxel for live human brain associated with gray matter, white matter, and cerebrospinal fluid. Peaks at 0.23 and 1.2 μm/ms are apparent. FIGS. 17-20 illustrate additional examples of CDF images and associated spectra obtained using IGDTI.

Single Shot Isotropic Diffusometry MRI

As discussed above, mean apparent diffusion coefficient (mADC), or the mean diffusivity (MD), obtained with diffusion tensor imaging (DTI) is an eloquent and robust clinical biomarker for diagnosing and characterizing ischemic stroke, cancer, and numerous other neurological disorders and diseases. As an imaging parameter, the mADC removes signal modulations from bulk diffusion anisotropy and provides an average measure of water mobility even in anisotropic white matter. The value of mADC can depend on experimental parameters, such as diffusion sensitization (b-value) and diffusion time, and is affected by restrictions at a microscopic scale (i.e., microscopic anisotropy). Therefore, the mADC measured with conventional methods is not a proper statistical average of the intrinsic tissue water mobilities in microscopic pools, and can provide a biologically nonspecific assessment of microstructural changes in pathology.

Disclosed herein is a noninvasive, model-free, whole-brain method for quantifying the spectrum of intrinsic tissue water mobilities in human subjects. Using a single-shot spherical diffusion encoding (SDE) preparation, signal confounds caused by anisotropic diffusion (e.g., tissue architecture, cell shapes, and sizes) are reduced or eliminated, and diffusion weighted images (DWIs) can be acquired in vivo over a wide range of diffusion sensitizations. Measured SDE signal decays can be analyzed using a regularized 1-D inverse Laplace transform (ILT) to derive intravoxel tissue water mean diffusivity distributions (MDD). In some cases, whole-brain measurements are described, other specimens can be similarly evaluated.

In this example, in vivo diffusion weighted images (DWIs) with spherical diffusion encoding (SDE) are obtained over a wide range of diffusion sensitizations (b-values). From such measurements, intrinsic tissue water mean diffusivity distributions (MDD) can be estimated in, for example, healthy or diseased human brain tissue (or other in vivo or in vitro specimen) in each voxel. These distributions of rotation-invariant mean diffusivity values can be compared using region-of-interest analysis (ROIs).

Figure 21:
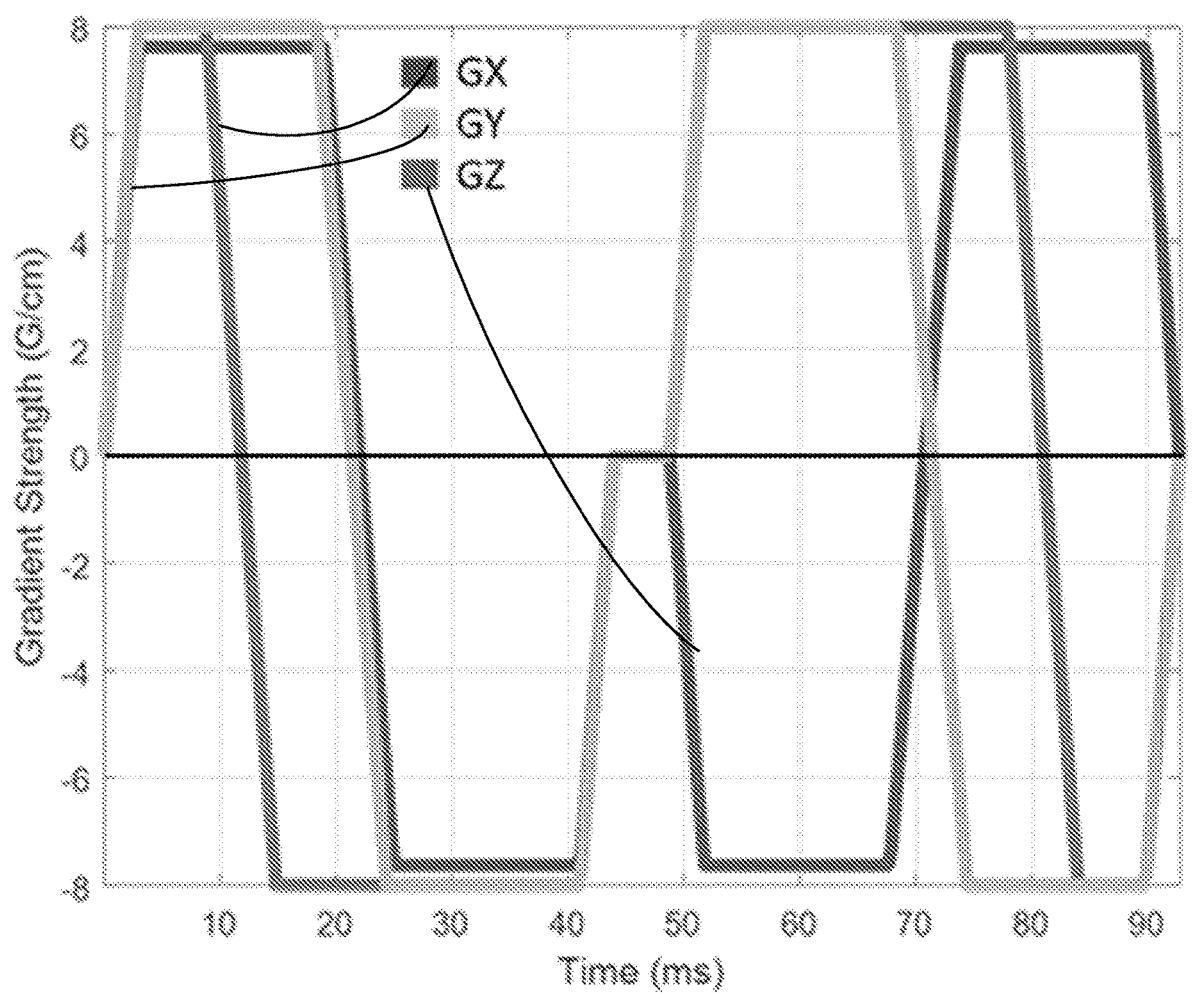
FIG. 21 illustrates a gradient pulse sequence selected to provide single shot spherical diffusion encoding (SDE).

Referring to FIG. 21, a pulse sequence 2100 selected to provide SDE over a large range of b-values in a single acquisition includes gradient sequences associated with X, Y, and Z gradients, and a 180 degree refocusing RF pulse that temporally divides the gradient sequences. Crusher gradients are also applied, but are not illustrated. The example of FIG. 21 illustrates a pulse sequence associated with a desired maximum b-value, $b_{max}$; maximum gradient amplitude, $G_{max}$; and trapezoidal ramp duration, r, pulse widths $\delta_x$, $\delta_y$, and $\delta_z$, of the first trapezoidal pulses on X, Y, and Z axes, along with the ratio R of the gradient amplitude on X to $G_{max}$ required to achieve isotropic diffusion sensitization, i.e., SDE. The resulting pulse sequence in the example of FIG. 21 uses only trapezoidal gradient pulses, which can be easily programmed and debugged on in a clinical scanner and, most importantly, achieves a very efficient SDE in a short diffusion time. FIG. 21 shows the gradient waveforms for a $b_{max}$ of 6000s/mm2, refocusing duration of 5 ms, and ramp time of 3 ms. In one example, once the fidelity of the gradient pulse shapes and timings were verified, a number of slices and a repetition time were empirically adjusted to accommodate the power dissipation and duty cycle limits of the gradient system. More general and possibly more efficient SDE pulse sequences can be designed and optimized. Procedures for pulse optimization are described in Sjölund et al., 'Constrained optimization of gradient waveforms for generalized diffusion encoding," J. Magn. Resonance 261: 157-168 (2015), which is incorporated herein by reference.

FIG. 21 illustrates an effective diffusion gradient waveform for acquiring clinical SDE DWIs with a wide range of b-values, taking into consideration the refocusing effect due to the 180 RF pulse. The gradient waveforms GX, GY, and GZ use only trapezoidal pulses with ramp times of 3 ms. Using pulse widths $\delta_x$, $\delta_y$, and $\delta_z$ of the first trapezoid pulses on X, Y, and Z, along with the ratio R of the gradient amplitude on Z to $G_{max}$, the sequence achieves a maximum b-value $b_{max}$ of 6000 s/mm² with a diffusion preparation time of 92 ms.

FIGS. 22A-22C illustrate magnetic field gradient pulse sequences such as illustrated in FIG. 21 in greater detail. Referring to FIG. 22A, a Y-gradient pulse sequence includes pulses 2202, 2203 which are of opposite sign but have similar pulse area defined as an integral of gradient amplitude over pulse duration. Y-gradient pulses 2206, 2207 are of opposite sign and typically have the same pulse amplitude, duration, and area as the pulses 2202, 2203. As shown in FIG. 22A, the gradient pulses 2202, 2203 are followed by a 180 degree pulse 2204 prior to the application of the gradient pulses 2206, 2207. The 180 degree pulse 2204 effectively inverts the applied Y-gradient, and the gradient pulses 2206, 2207 as shown include the effective inversion. Actual applied gradients after the 180 degree pulse 2204 are shown as an applied gradient pulse portion 2210 with dashed lines.

In the examples of FIGS. 21-22C, magnetic field gradient pulses associated with field components along orthogonal axes include equal areas prior to and after a refocusing pulse. In addition, pulses for each axes include equal amplitudes in a + direction and a − direction. Such pulse sequences (along with the associated refocusing pulse) are referred to herein as three-dimensional, refocusing balanced magnetic field gradient pulse sequences for convenience. In addition, a pulse sequence associated with at least one axis exhibits a temporal reflection symmetry with respect to the refocusing pulse. For example, the pulses 2212, 2217 and 2213, 2216 are the same as if applied in an opposite temporal sequence. A pulse sequence associated with at least one axis exhibits a temporal inversion symmetry, i.e., would be the same if pulse polarities were inverted and the inverted pulses applied in reverse temporal order.

The gradient pulses 2202, 2203, 2206, 2207 are typically trapezoidal for convenience, but other pulse shapes can be used, but in any case, each of these pulses preferably has the same pulse area. This is typically achieved by using the same pulse shape, pulse amplitude, and pulse duration for each gradient pulse.

Referring to FIG. 22B, a Z-gradient pulse sequence includes pulses 2212, 2213 which are of opposite sign but have substantially the same pulse area defined as an integral of gradient amplitude over pulse duration. Z-gradient pulses 2216, 2217 of opposite sign typically have the same pulse amplitude and same pulse area as the pulses 2212, 2213. All of these pulses have the same pulse area as the gradient pulses 2202, 2203, 2206, 2207 shown in FIG. 22A. As shown in FIG. 22B, the gradient pulses 2212, 2213 are followed by the 180 degree pulse 2204 prior to the application of the gradient pulses 2216, 2217. The 180 degree pulse 2204 effectively inverts the applied Z-gradient, and the gradient pulses 2216, 2217 as shown include the effective inversion. Actual applied gradients after the 180 degree pulse 2204 are shown as an applied gradient pulse portion 2220 with dashed lines. As discussed above, the gradient pulses 2212, 2213, 2216, 2217 are typically trapezoidal for convenience, but other pulse shapes can be used.

Referring to FIG. 22C, an X-gradient pulse sequence includes pulses 2222, 2223 which are of opposite sign. X-gradient pulses 2226, 2227 are of opposite sign of the pulses 2222, 2224 and typically have the same pulse amplitude, duration, and area as the pulses 2223, 2222, respectively. As shown in FIG. 22C, the gradient pulses 2222, 2223 are followed by the 180 degree pulse 2204 prior to the application of the gradient pulses 2226, 2227. The 180 degree pulse 2204 effectively inverts the applied X-gradient, and the gradient pulses 2226, 2227 as shown include the effective inversion. Actual applied gradients after the 180 degree pulse 2204 are shown as an applied gradient pulse portion 2230 with dashed lines. As discussed above, gradient pulses are typically trapezoidal for convenience, but other pulse shapes can be used.

In one example, durations for the pulses of FIGS. 22A-22C can be computed numerically to ensure isotropic encoding. Using the notation of FIGS. 22A-22C, the durations are:

FIG. 22A-Y Gradient Pulse Durations
Pulse 2202=Pulse 2207=10.7923 ms
Pulse 2203=Pulse 2207=11.2077 ms
FIG. 22B-Z Gradient Pulse Durations
Pulse 2212=Pulse 2213=Pulse 2216=Pulse 2217=11 ms
Z-gradient amplitude is scaled by R=0.9796 compared to X-, Y-gradient amplitudes
FIG. 22C-X Gradient Pulse Durations
Pulse 2222=Pulse 2227=3.5261 ms
Pulse 2223=Pulse 2226=18.4739 ms In typical examples, many gradient pulses have durations that are the same within 5%, 4%, 3%, 2%, or 1% and a ratio of pulse durations for pulses such at the pulse 2223 to the pulse duration for the pulse 2222 is greater than 2, 2.5, 3, 4, 5, or 6.

Clinical Application to Human Brain Data

Five healthy volunteers were scanned on a clinical MRI scanner equipped with a maximum gradient strength of 8 G/cm/axis and with a 32-channel RF coil under a clinical protocol approved by the institutional review board (IRB) of the Intramural Program of the National Institute of Neurological Disorders and Stroke (NINDS). Whole brain SDE DWIs were acquired with a 21-cm field-of-view (FOV), an in-plane resolution of 2.4 mm, a 5 mm slice thickness, echo time (TE) of 93 ms, and repetition time (TR) of 6s. Images were acquired at 60 b-values from 0 to 6000 s/mm$^2$, with multiple averages for images with higher b-values, in a total scan duration of 15 minutes. In addition, we also acquired a DTI scan (using the same scan parameters but a b-value of 1000 s/mm$^2$ and only 35 orientations), and a high-resolution anatomical T$_2$-weighted scan. All diffusion data sets were processed with the TORTOISE software package to correct for echo-planar imaging (EPI) distortions due to eddy currents and field inhomogeneities to register all DWI volumes to the high resolution T$_2$-weighted anatomical template and to resample the corrected images to a 2.5 mm isotropic resolution.

Monte Carlo Numerical Simulations

Numerical simulations were performed to determine the sensitivity of the disclosed approach to reconstructing model-free spectra of mean diffusivities. Starting with ground truth mean diffusivity spectra containing one or two peaks, we simulated SDE measurements at the same b-values used in our clinical experiment. We then added Gaussian noise to the real and imaginary channels and computed simulated DWIs with a signal-to-noise ratio (SNR) of 200:1 in the non-diffusion attenuated (baseline) image, which is similar to the SNR levels in our clinical data sets. We generated noisy SDE DWIs for the experimental design used for clinical scanning (number of b-values and averages) and analyzed the signal decays using the same inverse Laplace transform (ILT) method described below. We estimated mean diffusivity spectra from 500 independent instances of noisy measurements and quantified mean and standard deviations of these measurements for each spectral component. The ground truth MDDs were 1) Gaussian distribution with a mean of 0.8 μm$^2$/ms and standard deviation of 0.2 μm$^2$/ms and 2) mixtures of two Gaussian distributions with means of 0.4 and 0.9 μm$^2$/ms, respectively, standard deviations of 0.2 μm$^2$/ms, and signal fractions of 0.4 and 0.6, respectively.

Inverse Laplace Transform (ILT) Analysis

At every b-value, the SDE DWI signal in each voxel, S(b), provides isotropic weighting in each microscopic intravoxel water pool and is related to the mean diffusivity probability distribution (MDD) in these water pools, p(D), via a 1-D Laplace transform $S(b)=\int_0^\infty e^{-bD}p(D)dD$. From multiple SDE DWIs with different b-values, we can estimate p(D) using a numerical implementation of the 1-D ILT. To obtain a well-behaved solution to this ill-posed problem we used L$_2$-norm regularization with positivity constraints implemented in MATLAB:

$$\hat{p} = \arg\min_{p>0}\left\|\begin{bmatrix}M\\\lambda I\end{bmatrix}p - \begin{bmatrix}S\\0\end{bmatrix}\right\|_2^2,$$

S=S(b) and p=p(D) are vectors containing the SDE signals at different b-values and the spectrum of mean diffusivities, respectively; I is the identity matrix; M is the encoding matrix with $M_{ij} = \int_{D_j - \Delta D}^{D_j + \Delta D} e^{-b_i \cdot D} dD$; and $\lambda$ is a regularization parameter that controls the smoothness of the solution vector $\hat{p}$ and is optimized for each voxel.

ROI Analysis

To characterize differences between mean diffusivity distributions in brain tissues with improved statistical power, we quantified average MDDs in representative ROIs. We defined whole-brain ROIs in cortical gray matter (GM), subcortical gray matter (scGM) containing the basal ganglia, white matter (WM), corpus callosum (CC), and cerebrospinal fluid (CSF) by carefully excluding voxels at tissue interfaces that may be contaminated by partial volume artifacts. In each ROI we computed average tissue-specific MDDs to characterize differences between tissues. Finally, we reanalyzed the DWI data to compute signal fractions of these "pure" tissue spectra by solving a better conditioned problem:

$$\arg \min_{f>0} \|Tf - s\|_2^2,$$

where the solution f contains the three unknown signal fractions associated with the (normalized) pure tissue spectra $p_i$, (I=CSF, WM, GM) and matrix T is defined by $T_{ij} = \int_0^\infty e^{-b_i \cdot D} p_j(D) dD$.

Representative Results: Monte Carlo Simulations

Figure 23A:
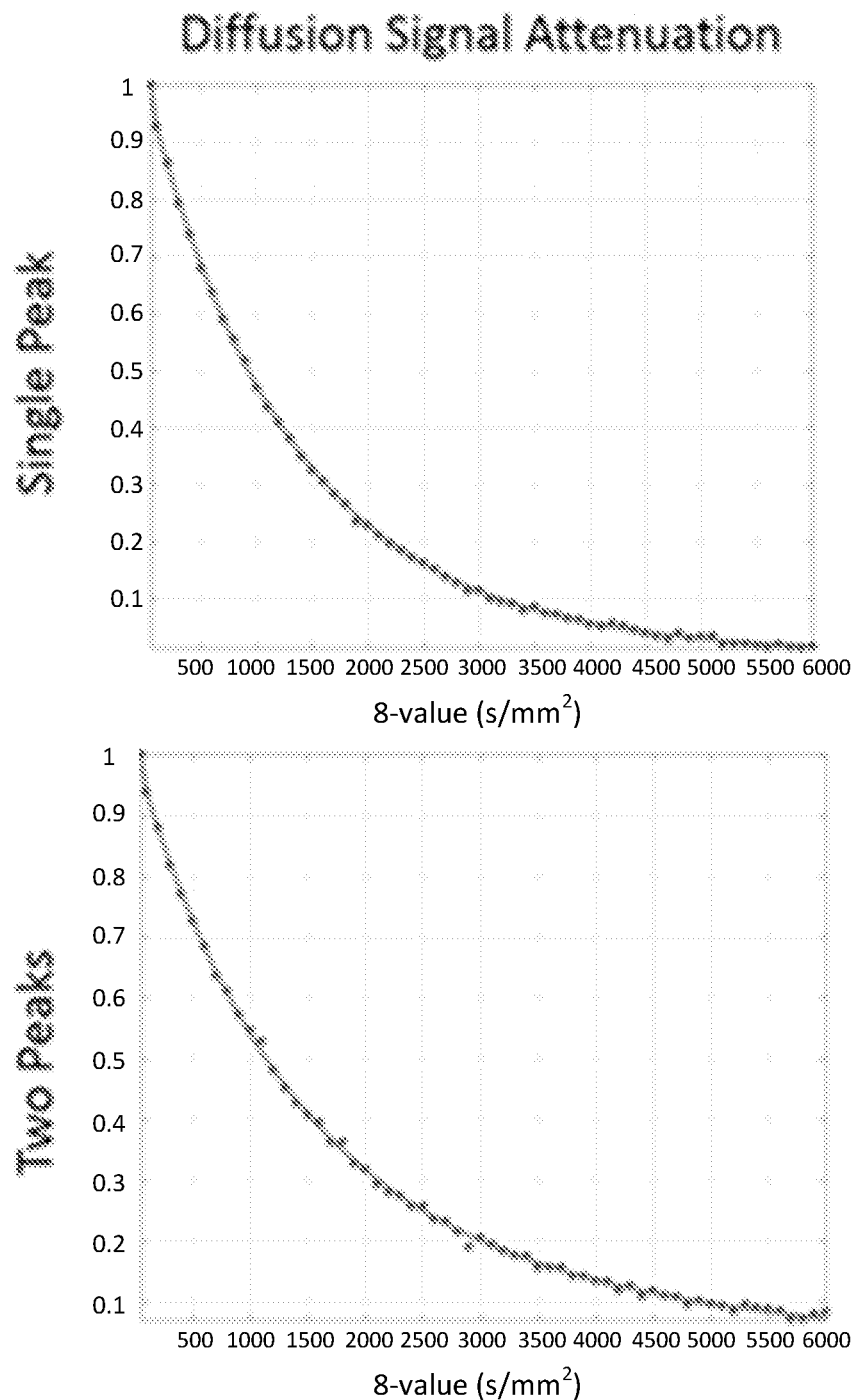
FIGS. 23A-23B illustrate numerical simulation analyses of noisy SDE signal attenuations with similar noise statistics and experimental design used in representative clinical experiments.
Figure 23B:
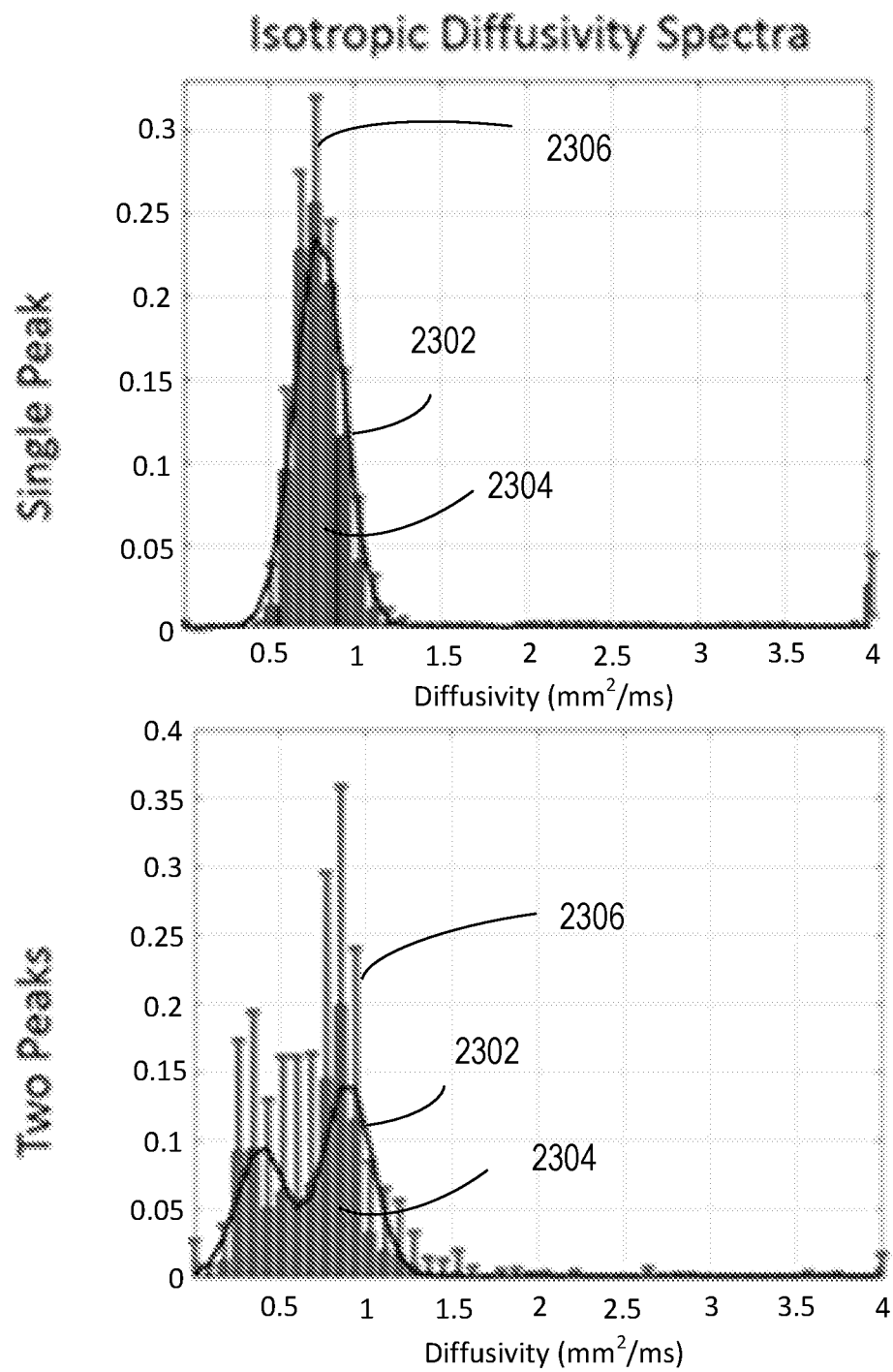

Numerical simulations using experimental designs and noisy SDE signal attenuations similar to those expected in our clinical data sets suggest that it is possible to estimate MDDs by using the regularized ILT analysis. As shown in FIGS. 23A-23B, a single peak distribution can be measured reliably with very good estimates of the peak location and width. For a bimodal distribution, the separation between the peaks in the estimated MDD is slightly smaller, potentially due to the grouping effect of $L_2$-norm regularization. Average MDDs computed from multiple instances of noisy data generally provide good approximations of the ground truth MDDs in both unimodal and bimodal distributions.

Representative Results: Mean Diffusivity Distributions (MDDs) in the Human Brain Characteristic values of SNR in the non-diffusion attenuated (i.e., baseline b=0 s/mm$^2$) images were 150 in WM, 250 in cGM, 110 in the CC, 105 in scGM, and 300 in CSF. Based on our Monte Carlo simulations, these SNR levels are sufficient for reliable estimation of MDDs in most brain tissues.

These results reveal a remarkable consistency between average water mobilities in healthy human brain tissue. MDDs in healthy brain parenchyma consistently show single-peak distributions with slight differences in peak locations and shapes. Indeed, the SDE signal decay in most of the brain parenchyma can be modeled reasonably well even with a single exponential decay (see FIGS. 27A-27B). Distributions with multiple peaks were measured primarily in CSF voxels near tissue interfaces and are likely due to significant partial volume contributions. MDDs were generally broader in GM and narrower in WM, especially in the CC. MDDs in WM reveal slightly higher average mean diffusivities than in GM. Voxels containing CSF showed a distinctive, dominant peak with significantly higher mean diffusivity, closer to 3 mm$^2$/µs of water at body temperature, as expected. The largest fractions of low diffusivity components, <0.85 mm$^2$/µs, were observed in scGM regions, in particular, in the putamen, the globus pallidum, and caudate nucleus and, to a lesser extent, the thalamus. To better visualize the interesting spatial-spectral features in the whole-brain normalized MDDs, we computed signal components in three distinct spectral regions: low diffusivity component (<0.85 mm$^2$/µs), intermediate diffusivity component (0.85-2.00 mm$^2$/µs), and high diffusivity component (>2.00 mm$^2$/µs), i.e., a CSF (free water) component (see FIGS. 25A-25B).

Tissue-Specific MDDs

Figure 24:
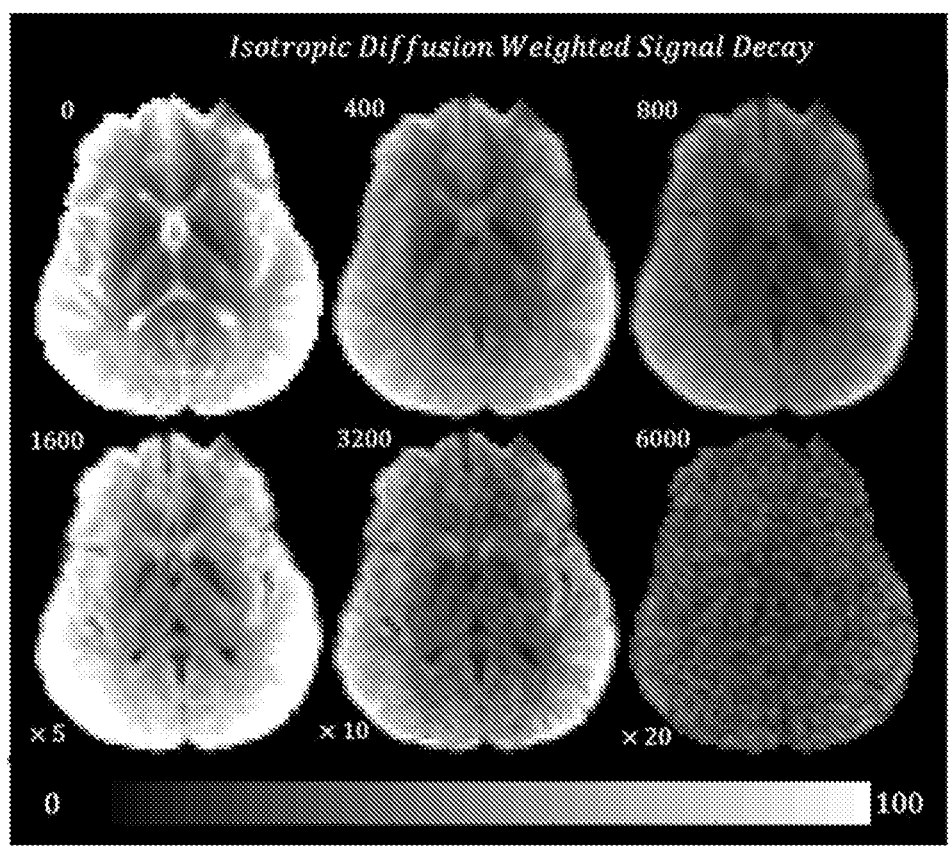
FIG. 24 illustrates SDE signal attenuations over a wide range of diffusion sensitizations.

Numerical simulation results suggest that averaging MDDs (e.g., from multiple voxels within an ROI) can improve the statistical power and provide good estimates of the ground truth distributions. While voxel-wise MDD estimates are inherently ill-conditioned, the ROI-averaged tissue-specific MDDs (FIGS. 24-25B) were very robust and reproducible with little dependence on the specific regularization strategies used for voxel-wise fitting. Average normalized MDDs computed in different ROIs showed very similar single-peak distributions of mean diffusivity values in GM, WM, scGM, and CC, with slight differences in the center locations and shapes of the distribution (FIG. 24).

By using tissue fractions computed by fitting the SDE signal decay in each voxel from tissue-specific MDDs (FIG. 5), for instance, in ROIs within the same subject (internal control) or in normative healthy populations, differences between average water mobilities in brain tissues in clinical scans may be detected from fewer measurements. These tissue fractions may reflect biologically specific differences in water diffusion properties of tissues and could provide new clinical markers for studying and assessing changes in water microdynamics in stroke, edema, cancer, or neurodegenerative disorders and diseases.

FIGS. 23A-23B illustrate numerical simulation analyses of noisy SDE signal attenuations with similar noise statistics and experimental design used in the clinical experiments. FIG. 23B shows an example of noisy diffusion signal attenuation simulated with an SNR of 200:1 at 60 b-values similar to the in vivo human brain data. FIG. 23B shows the ground truth (line 2302) and average estimated (bar graph 2304) intravoxel MDDs estimated by analyzing the 200 instances of simulated noisy data with the regularized 1-D ILT fit described herein. The ground truth MDDs were 1) a single Gaussian distribution with a mean of 0.8 µm$^2$/ms and standard deviation of 0.2 µm$^2$/ms and 2) mixtures of two Gaussian distributions with means of 0.4 and 0.9 µm$^2$/ms, respectively, standard deviations of 0.2 µm$^2$/ms, and signal fractions of 0.4 and 0.6, respectively. Lines 2306 represent error bars for each diffusivity component. These results show that the ILT analysis reliably estimates the peak location and width for single-peak distributions. FIG. 24 illustrates SDE signal attenuations over a wide range of diffusion sensitizations (b=0-6000 s/mm$^2$) measured in the live human brain. Characteristic values of SNR in the non-diffusion attenuated (b=0 s/mm$^2$) images were 150 in WM, 250 in cGM, 110 in CC, 95 in dGM, and 300 in CSF.

Figure 25A:
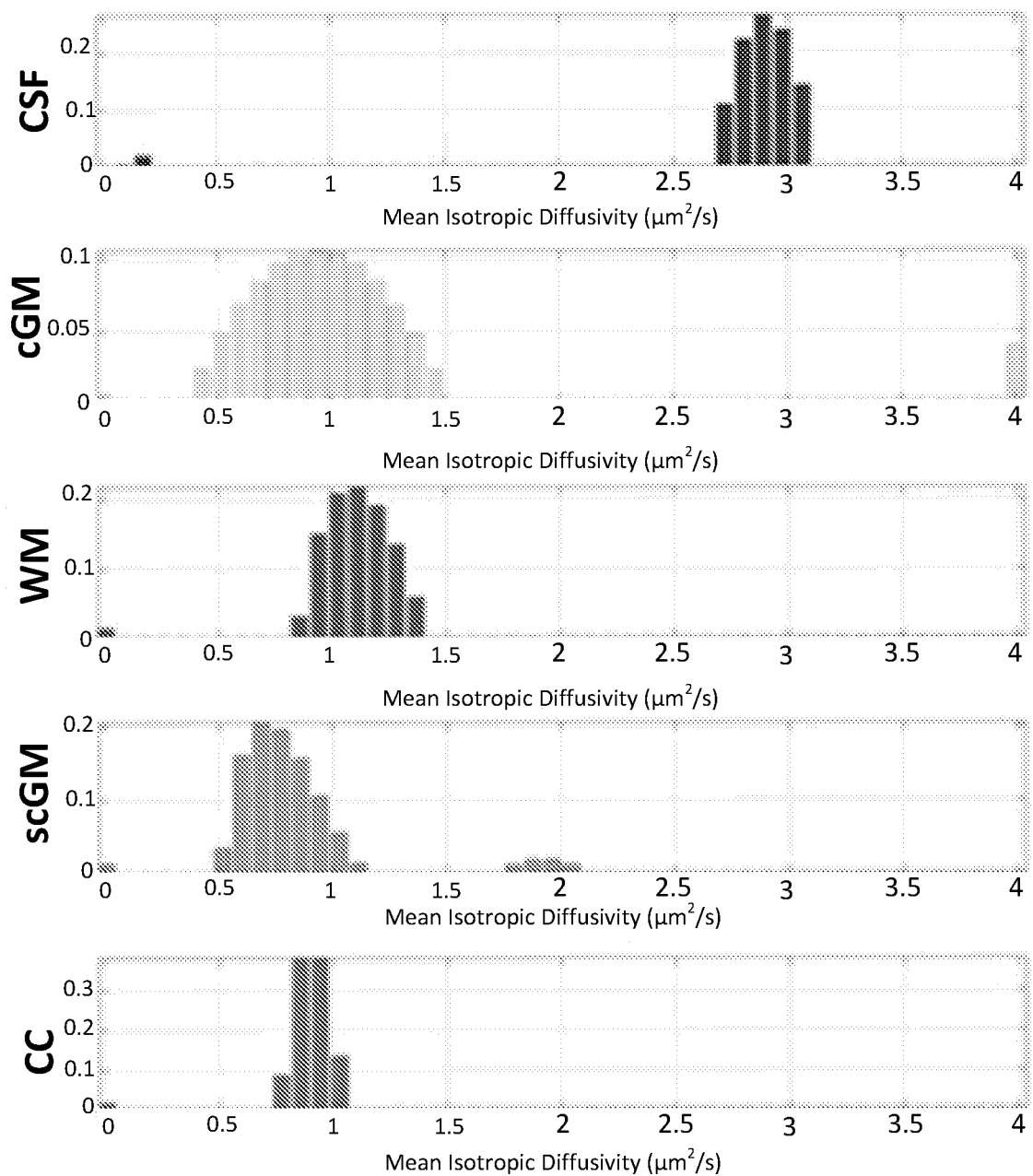
FIG. 25A illustrates estimated spectra of intravoxel mean diffusivity values in representative brain tissues.
Figure 25B:
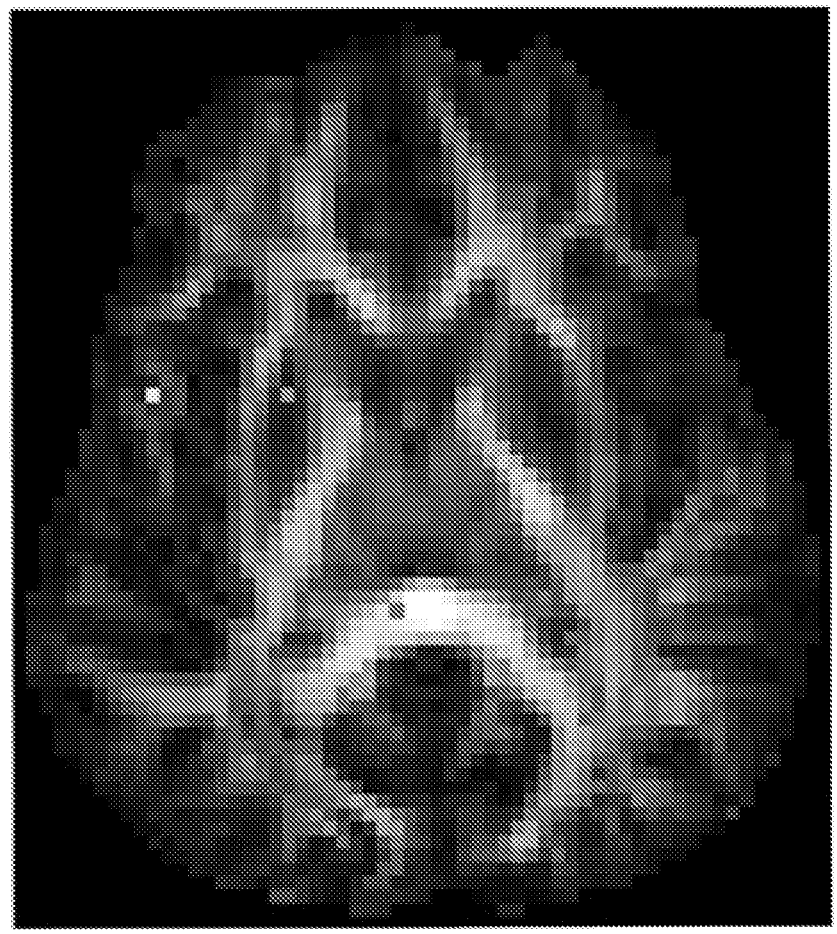
FIG. 25B is a fractional anisotropy map showing the locations of the selected voxels.

FIG. 25A illustrates estimated spectra of intravoxel mean diffusivity values in representative brain tissues. Single peaks were observed in all tissue types; multiple peaks were observed only in brain regions with significant tissue partial volume effects. The distribution was generally broader in cGM and narrower in WM, especially in the CC. Meanwhile, in regions of CSF a single narrow peak with significantly faster diffusivity was observed, as expected. MDDs in scGM voxels showed consistently lower mean values than those in cGM and WM voxels. FIG. 25B is a fractional anisotropy map showing the locations of the selected voxels.

Figure 26:
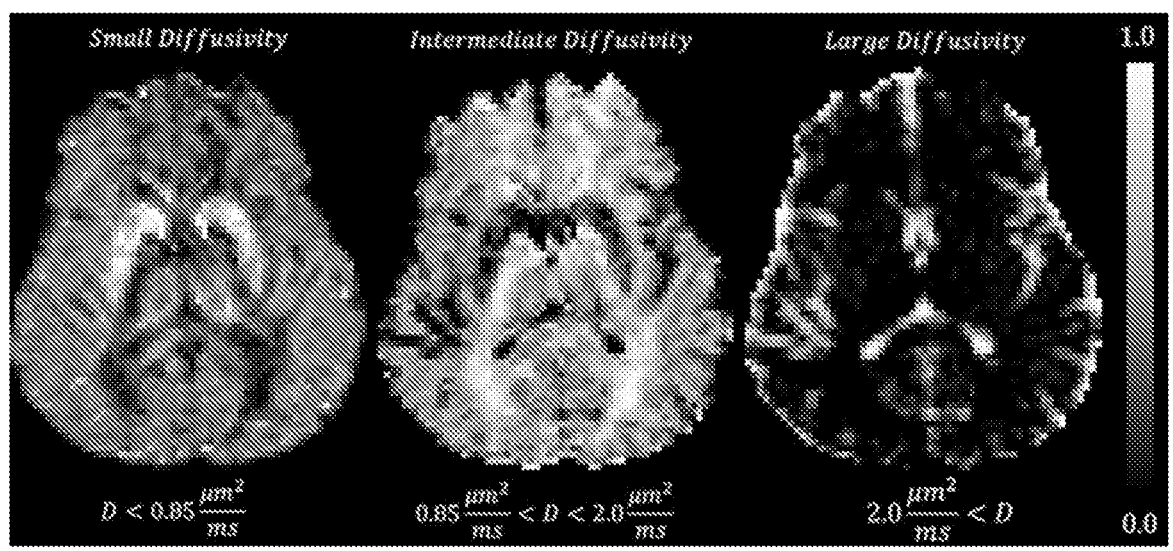
FIG. 26 illustrates low, intermediate, and large diffusivity signal components in normalized mean diffusivity distributions (MDDs) measured in the live human brain.

FIG. 26 illustrates low, intermediate, and large diffusivity signal components in normalized MDDs measured in the live human brain. Subcortical gray matter—in particular, the putamen, the globus pallidum, and caudate nucleus, and to a lesser extent the thalamus—contained mostly low diffusivity components <0.85 $\mu m^2/ms$. Brain regions containing major white matter fibers were dominated by intermediate diffusivity components in the range of 0.85 to 2.0 $\mu m^2/ms$. Meanwhile, the broad peaks in cGM revealed significant components in both low and intermediate mean diffusivity ranges. As expected, large diffusivity values were observed mainly in regions of CSF.

FIG. 27A illustrates normalized tissue-specific MDDs averaged over whole-brain ROIs defined in CSF—A; cGM—B; WM—C; scGM containing mainly the putamen, the globus pallidum, and caudate nucleus—D; and the CC—E. FIG. 27B illustrates a representative slice showing the ROIs; voxels at tissue interfaces were excluded from the ROIs to minimize contributions from partial volume effects.

Figure 28:
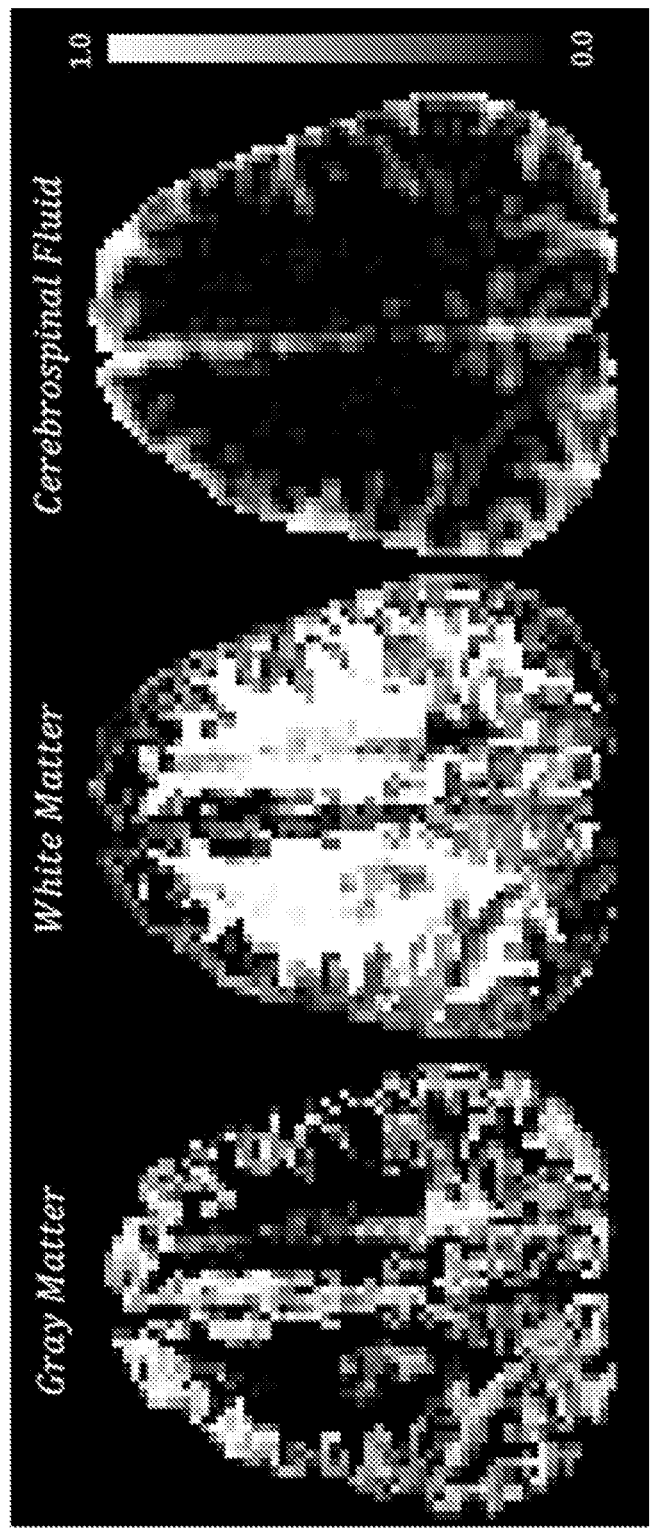
FIG. 28 illustrates tissue signal fractions obtained by fitting the SDE signal decay in each voxel with the average tissue spectra obtained from an ROI analysis.

FIG. 28 illustrates tissue signal fractions obtained by fitting the SDE signal decay in each voxel with the average tissue spectra obtained from the ROI analysis. These results show that slight differences between average water mobilities in brain tissues could be potentially detected (and accelerated). The increased partial volume of white matter in gray matter regions corresponding to the precentral and postcentral gyri, which are associated with increased levels of cortical myelination.

Spherical Diffusion Encoding

The SDE pulse sequence in FIGS. 21-22C provides isotropic diffusion encoding in an intravoxel microscopic water pool whose diffusion properties can be described with an arbitrarily oriented diffusion tensor. From the SDE signal decay over a wide range of b-values an estimate of a model-free and rotation-invariant distribution of the mean diffusivities of all intravoxel water pools.

At each b-value, the rotation-invariant SDE signal measured is different from rotation-invariant signals (e.g., mADC-weighted signal) derived from multiple DWIs acquired with the Stejskal-Tanner spin echo diffusion pulse sequence and different gradient orientations. The conventional Stejskal-Tanner diffusion preparation is not sensitive to diffusion-diffusion correlations and achieves only linear diffusion encoding (LDE) along a particular orientation. While rotation-invariant measurements (i.e., independent of tissue orientation) using both LDE and SDE can be derived, the ILT of the SDE signal decay provides a direct quantitation of the distribution of mean diffusivities in intravoxel water pools. A similar ILT analysis of orientation-averaged (i.e., mADC-weighted DWIs) can provide rotation-invariant "spectra" that, while lacking the biophysical interpretation of SDE-derived MDDs, can nevertheless be obtained with higher spectral resolution (from DWIs with higher b-values) and may provide acceptable contrast for tissue classification and clinical characterization.

The MDDs measured via the 1-D ILT of the SDE signal decay profile quantify intrinsic water diffusivities, assuming that in each non-exchanging intravoxel water pool diffusion is Gaussian. For living biological tissues, deviations from this assumption may arise due to the presence of microscopic flow, i.e., intravoxel incoherent motion exchange between water pools, the presence of magnetic inhomogeneities in the sample (e.g., iron), and microscopic restricted diffusion, likely leading to diffusion-encoding, time-dependent MDD components. In addition, MDDs are inherently $T_1$- and $T_2$-weighted by the TE and TR used for MRI data acquisition, highlighting the need for multidimensional MR relaxometry analysis.

Both SDE and ILT analysis assume that diffusion in individual microscopic water pool is Gaussian. This assumption may be violated in microenvironments where water is highly restricted over the scale of the diffusion preparation duration (~90 ms in this example).

Sources of Error in SDE Measurements

Actual diffusion encoding may vary from the expected spherical diffusion encoding, especially at high b-values, due to the several sources:
 1. Concomitant field effects that are not refocused by the 180 degree pulse.
 2. Contributions of field inhomogeneities to the b-value/b-tensor. The presence of magnetic field inhomogeneities in the sample (during the entire diffusion duration) can alter the effective diffusion encoding making it non-spherical, and voxel-dependent. This is expected to be especially important for high magnetic field imaging, (or imaging near metals).
 3. Gradient non-linearities. Nonlinearities in the magnetic field gradients generated by imperfections in the coil design, for example, can also lead to diffusion encoding values that are different than expected, potentially even not spherical. These contributions also vary spatially, usually increasing with distance from the magnet isocenter,
 4. Eddy currents can cause unwanted contributions to the diffusion encoding values in addition to causing imaging distortions (EPI distortions, as well as slice bending during refocusing). Imaging artifacts are managed in postprocessing (refocusing thicker slices), and
 5. Intravoxel incoherent motion (IVIM) due to physiological motion (e.g., pulsations, tissue perfusion) in DWIs acquired with low b-values can cause time-dependent errors throughout the scan duration and potentially manifest as signal components with high diffusivity.

While all these factors can lead to imperfect SDE especially at high b-values, the pulse sequence proposed here using trapezoidal gradient waveforms may allow an easier quantitation of these errors necessary for subsequent voxel-wise correction of diffusion encoding values.

Model-Free Assessment of MDDs

A method referred to herein as diffusional variance decomposition (DIVIDE) uses both SDE and LDE measurements to estimate microstructural parameters, such as the average mean diffusivity, and microscopic fractional anisotropy, and shows promise for clinical applications in tumors. The robustness of DIVIDE relies, in part, on assuming an analytical form for a single-peak MDD in the voxel. The examples results disclosed herein support this assumption in brain parenchyma and regions with negligible partial volume contributions, but also highlight the need for characterizing regions with partial volume and pathophysiological tissue changes by explicitly estimating MDDs with model-free approaches:

1. The shapes of these peaks appear to differ (among tissues and) from the assumed Gamma distribution used in DIVIDE.
2. Voxels with partial volumes of CSF can have bimodal distributions (38% of total voxels in the example described herein).
3. For clinical applications, where there may be pathology, the actual distributions are not known a priori and may differ significantly from any assumed parametric function.

Imaging Parameters

The examples disclosed herein are directed to obtaining measurable SDE signals with very large diffusion sensitization that allows estimation of MDDs with good spectral resolution. Additionally, an efficient SDE waveform was used that allows imaging with relatively short TEs and enhanced scan efficiency by reducing the number of slices per TR to accommodate gradient heating and duty cycle requirements. While additional optimization may be possible, the disclosed DWI sequence uses only trapezoidal gradient pulses and can be readily implemented on conventional clinical scanners.

To achieve the SNR levels required for ILT analysis predicted by Monte Carlo simulations, voxel volume was adjusted. The anisotropic voxel size (2.5 mm in plane with a 5 mm slice thickness) was chosen to minimize imaging artifacts due to Gibbs ringing in regions around CSF in images with very low diffusion sensitization. Additional improvements in SNR (shorter TE) and reductions in Gibbs ringing artifacts can be obtained with a spiral-out imaging trajectory.

Even though the temporal SNR in the disclose study was close to 200, as required for numerical simulations, additional sources of errors due to Nyquist ghosting, incomplete fat suppression, physiological and subject motion, and magnetic field inhomogeneity could lead to voxel signal instabilities that exceed 1 in 200, and therefore need to be considered carefully. The high SNR (~200) in low resolution DWIs can also be degraded by incomplete fat suppression, and ghosting can also result in a superposition of artifactual signals with a relative intensity of ~5% of the object intensity. To prevent these problems, spatial spectral excitation RF pulses were used for fat suppression and DWIs acquired with full k-space sampling. Signal instabilities that may arise due to patient and physiological motion can be mitigated by keeping the total scan duration short. The SDE scans in the example above took 15 minutes; subjects were instructed to remain still during that time.

Sources of Error in In Vivo Quantitation of CSF

Errors in the quantitation of CSF peak (shape and location) may be due to partial volume contributions from brain tissue in the 2.5×2.5×5 mm voxel used, which may vary with subject and physiological motion during the duration of the scan. In DWIs acquired with low diffusion sensitizations (b-value <200 s/mm$^2$) the signal intensity from CSF can be significantly larger than that from brain parenchyma due to the larger proton density, longer T2 (TE=105 ms used in our study), and closer proximity to the RF receiver array of voxels containing mainly CSF. This difference in signal intensity exacerbate quantitation errors caused by instabilities in voxel partial volume contributions in the presence of subject/physiological motion. In addition, this large signal difference between CSF and surrounding voxels (brain tissue, skull, etc.) in DWIs acquired with low b-values gives rise to Gibbs ringing artifacts, which are especially problematic when data with high SNR is acquired, usually in low-resolution scans. The level of Gibbs ringing in the disclosed study was ~5% in DWIs with b<100 s/mm$^2$. For some subjects (with larger head size), excluding measurements with b<100 s/mm$^2$ from the ILT analysis in voxels with high CSF content stabilizes the position of the CSF peak and prevents artifactual accumulation of diffusivity components at the upper bound of the spectral range.

Our study used a large voxel size to achieve the high SNR required for ILT analysis. However, using large imaging voxels in vivo can lead to signal artifacts in voxels with partial volume effects. Signal inconsistencies significantly larger than the noise level can arise in voxels with significant CSF partial volume contamination in low-b DWIs, where the CSF signal is not crushed. In such voxels, even small variations in the relative voxel tissue composition (CSF vs. tissue) during normal physiological or subject motion leads to significant signal variations ~2-5%, above the noise level in images with SNR=200. These signal artifacts can significantly deteriorate the fidelity of the estimated diffusivity spectra. The most contaminated voxels are at the GM/CSF boundary where the high receive sensitivity of the RF coil array further amplifies these signal variations (and SNR), and near the ventricles where physiological motion is most notable. These variations can be visualized by looking at the median and standard deviations of DWIs as a function of b-value. The effect of partial volume inconsistencies can be mitigated by:

1. removing outliers from low-b DWIs (e.g., based on the standard deviation of repeated measurements),
2. reducing the total scan duration to minimize the impact of physiological and subject motion (e.g., by acquiring fewer data), or
3. fitting spectral diffusivity components only for the range of parenchymal diffusivities (0.1-1.5 mm2/s) and have a fixed diffusivity for CSF @ 3 mm2/s. This separation of CSF is simpler and more elegant than in the conventional free water elimination technique used in DTI since the diffusion signal decay is inherently analyzed as a sum of exponential decays, without the need for computing the log of the signal attenuation.

Because these CSF-related artifacts in DWIs with high SNR appear at low-b images mitigating them, also mitigates some of the Gibbs ringing.

MDDs in Healthy Brain

The representative results disclosed herein suggest a remarkable consistency in the isotropic water mobility both across subjects and across all regions of healthy brain parenchyma, with little differences between the intravoxel water pools. The MDDs in healthy brain tissues show similar single-peak spectra with slightly different locations and shapes. These slight differences in MDDs may reflect microstructural differences in the size of cellular restrictions, packing, cellularity, properties of extracellular matrix, intracellular hindrances and structures, or differences in active physiological properties such as the microdynamics of axonal transport and water exchange. Local susceptibility gradients due to large iron concentrations in the basal ganglia may also play an important role in explaining the relatively large difference in peak locations between scGM and GM, compared with peak locations in WM and GM. Characterizing the diffusion-encoding time dependence of MDDs can reveal spectral components corresponding to restricted water pools.

The remarkable consistency of intrinsic water mobilities in healthy brain tissues may reflect a stability of water microdynamics associated with the homeostatic/energetic balance required for normal cellular metabolism.

Clinical Potential

The biological specificity that arises from measuring distributions of water mobilities in microscopic pools may find clinical applications in stroke, cancer, many neurodegenerative diseases and neuroinflammation, where conventional Trace or mADC imaging has already been shown to be clinically valuable. For example, changes in these intravoxel distributions could reflect disruption in microstructure (e.g., inflammation, dysmyelination, demyelination) or physiological changes in water exchange and transport processes in tissue (e.g., as seen in cancer). Despite the uniformity of isotropic water mobilities in healthy brain tissues, given the current clinical applications of conventional diffusion MRI to ischemia and stroke, it is likely that the MDDs measured with ID-MRI in patients may reveal significant changes in water microdynamics from healthy controls and could provide sensitive and potentially biologically specific markers for assessing cell metabolism following ischemia or in cancer.

CONCLUSION

The ability of IGDTI sampling and single shot schemes to assess rotation-invariant diffusion signals with a variety of diffusion sensitizations allows quantitation of a wide range of tissue water mobilities and opens up new avenues for pre-clinical and clinical translation, particularly for the development of new clinical applications with improved biological specificity and sensitivity to characterize stroke, cancer, and inflammatory or neurodegenerative diseases. Short IGDTI scan durations may reduce quantitation errors and imaging artifacts due to subject/physiological motion, improving the accuracy and clinical feasibility of isotropic diffusion MRI assessments for a wide range of patient populations, including non-compliant patients (e.g., elderly, agitated, fetal or pediatric patients).

The methods and apparatus discussed above can be used in isotropic diffusion relaxometry imaging (IDRI) in pre-clinical and clinical MRI applications, such as in brain imaging, studying and diagnosing ischemic stroke, tumors, neurodegenerative disorders and diseases, including inflammatory processes occurring in multiple sclerosis or traumatic brain injury (TBI). Using orientationally-averaged diffusion weighted images over a range of b-values permits estimation of mADC spectra, i.e., a distribution of mADCs in a specimen. Typically such distributions of mADC values (or other orientationally-averaged diffusion weighted quantities) are provided in specimen images, but distributions for a single ROI can be determined as well.

The example data above was obtained from fixed and living brains, but the disclosed methods and apparatus can be applied in whole-body image applications to scan organs including but not limited to the heart, placenta, liver, kidneys, spleen, colon, prostate, as well as skeletal and other muscles and peripheral nerves. The disclosed approaches can also be used in genotype/phenotype and other studies using vertebrates and other animal models as well as with non-biological materials, including foods, organic and synthetic polymers and gels, separation systems used in chemical engineering applications, soil and other samples, clay and rock, and other porous media.

In other applications, the disclosed methods and apparatus can be used in studying abnormal and normal developmental trajectories as well as a variety of disorders, diseases and sequelae of trauma, including mild traumatic brain injury, to follow and assess inflammatory responses in soft tissues, including the brain, in which immune and other cells may infiltrate into the extracellular matrix (ECM), and in evaluating and tracking wound healing and other time dependent cellular and tissue processes.

In view of the many possible embodiments to which the disclosed technology can be applied, it should be recognized that illustrated embodiments are only examples and should not be considered a limitation on the scope of the disclosure. We claim all that comes within the scope and spirit of the appended claims.

We claim:

1. A magnetic resonance imaging apparatus, comprising:
at least one gradient coil situated to produce a magnetic field gradient in a specimen in a plurality of directions, the plurality of directions including (1) three mutually orthogonal directions and (2) four directions evenly distributed over $4\pi$ steradians;
at least one signal coil situated to acquire signal attenuations corresponding to each of the directions in the plurality of directions at a plurality of b-values;
a data acquisition system coupled to the signal coil, and operable to produce a first signal attenuation average based on the signal attenuations associated with the three mutually orthogonal directions and a second signal attenuation average associated with the four directions evenly distributed over $4\pi$ steradians, at each of the plurality of b-values; and
a display coupled to the data acquisition system so as to display an image based on one or more of the first signal attenuation average and the second signal attenuation average.

2. A method, comprising:
obtaining, via a magnetic resonance imaging apparatus, isotropic gradient diffusion tensor images (IGDTIs) associated with at least one of a $2^{nd}$, $4^{th}$, or $6^{th}$-order diffusion tensor at a plurality of magnetic field gradient magnitudes;
based on the obtained IGDTIs at the plurality of magnetic field gradient magnitudes, determining, via a processor, at least one distribution of mADCs associated with at least one of a $2^{nd}$, $4^{th}$, or $6^{th}$-order diffusion tensor; and
displaying, on a display apparatus, an image based on the at least one distribution of mADCs,
wherein the IGDTIs are obtained by:
applying, via the magnetic resonance imaging apparatus, magnetic field gradients in directions associated with at least two sets of directions associated with the at least one of the $2^{nd}$, $4^{th}$, or $6^{th}$-order diffusion tensor;
combining, via the processor, the signal attenuations associated with the magnetic field gradients in each of the sets to produce a least a first signal attenuation average and a second single attenuation average; and
combining, via the processor, the first and second signal attenuation averages to determine the at least one distribution of mADCs.

3. A method, comprising:
applying, via a magnetic resonance imaging apparatus, diffusion sensitizing gradient fields having at least a first magnitude, a second magnitude, and a third magnitude along three orthogonal directions, wherein the first magnitude is less than the second magnitude and the second magnitude is less than the third magnitude, to obtain first mADC-weighted signals associated with the first, second, and third magnitudes;
applying, via the magnetic resonance imaging apparatus, diffusion sensitizing gradient fields at the second magnitude along four evenly distributed directions to obtain second mADC-weighted signals;
applying, via the magnetic resonance imaging apparatus diffusion sensitizing gradient fields at the third magnitude along four evenly distributed directions and along six directions corresponding to two mutually orthogonal directions in each of three mutually orthogonal planes to obtain corresponding third mADC-weighted signals;
combining at least two of the acquired first, second, or third mADC-weighted signals using a processor to obtain estimates of at least one of a $2^{nd}$ order mADC, a $4^{th}$ order mADC, or a $6^{th}$ order mADC; and
generating, via the processor, an image based on the estimates of the at least one of a $2^{nd}$ order mADC, a $4^{th}$ order mADC, or a $6^{th}$ order mADC.

4. A method, comprising:
applying, via a magnetic resonance imaging apparatus three-dimensional, refocusing balanced magnetic field gradient pulse sequences to a specimen at a plurality of b-values;
obtaining, via the magnetic resonance imaging apparatus, signal decays associated with a plurality of voxels of a specimen in response to the applied three-dimensional, refocusing balanced magnetic field gradient pulse sequences;
based on the obtained signal decays, estimating, via a processor, mean diffusivity distributions (MDDs) for each of the plurality of voxels; and
generating, via the processor, an image based on the mean diffusivity distributions (MDDs) for each of the plurality of voxels.

5. An apparatus, comprising:
a plurality of gradient coils that are situated to apply three-dimensional, refocusing balanced magnetic field gradient pulse sequences to a specimen at a plurality of b-values;
a receiver situated to detect signal decays associated with a plurality of voxels of a specimen in response to the applied three-dimensional, refocusing balanced magnetic field gradient pulse sequences; and
an MRI processor that estimates mean diffusivity distributions (MDDs) for each of the plurality of voxels based on the detected signal decays and generates an image based on the estimated MDDs for each of the plurality of voxels, wherein the image is displayed on a display device associated with the apparatus or transmitted over a network to a remote processor or a remote storage device.

6. The magnetic resonance imaging apparatus of claim 1, wherein the first signal attenuation average and the second signal attenuation average are combined to produce an image associated with a $4^{th}$-order mean apparent diffusion coefficient (mADC).

7. The magnetic resonance imaging apparatus of claim 1, wherein the first signal attenuation average and the second signal attenuation average are combined to produce a first image associated with a $2^{nd}$-order mADC at a low b-value, a second image associated with a $2^{nd}$-order mADC at an intermediate b-value, and a third image associated with a $4^{th}$-order mADC at the intermediate b-value.

8. The magnetic resonance imaging apparatus of claim 1, wherein the first signal attenuation average and the second signal attenuation average are combined to produce an image associated with a trace of a $4^{th\text{-}order\ diffusion\ tensor}$.

9. The magnetic resonance imaging apparatus of claim 1, wherein the data acquisition system is operable to produce a third signal attenuation average associated with gradient fields applied in six directions corresponding to two mutually orthogonal directions in each of three mutually orthogonal planes.

10. The magnetic resonance imaging apparatus of claim 9, wherein the first signal attenuation average and the third signal attenuation average are combined to produce an image associated with a $4^{th}$-ordermADC.

11. The magnetic resonance imaging apparatus of claim 9, wherein the first signal attenuation average, the second signal attenuation average, and the third signal attenuation average are combined to produce an image associated with a $6^{th}$-order mADC.

12. The magnetic resonance imaging apparatus of claim 9, wherein the first signal attenuation average and the third signal attenuation average are combined to produce an image associated with a $4^{th}$-order mADC and a $6^{th}$-order-mADC.

13. The magnetic resonance imaging apparatus of claim 9, wherein the second signal attenuation average or the third signal attenuation average are combined to produce an image associated with a $2^{nd}$-order mADC.

14. The method of claim 2, wherein the at least one distribution of mADCs is associated with the $4^{th}$ or $6^{th}$-order diffusion tensor.

15. The method of claim 3, wherein the each of the first, second, or third mADC-weighted signals are image signals for a plurality of voxels.

16. The method of claim 15, further comprising estimating a specimen motion based on the first mADC-weighted signals applied along the three orthogonal directions.

17. The method of claim 16, further comprising selecting a reference image based on mADC signal averages at a selected gradient magnitude and a selected set of the diffusion sensitizing gradient fields, and displacing an image based on the selected set of the diffusion sensitizing gradient fields and a different gradient magnitude so as to compensate for the estimated specimen motion.

18. The method of claim 17, wherein the specimen is fixed or living brain tissue, body organs and other tissues, including heart, placenta, liver, kidneys, spleen, colon, prostate, skeletal and other muscles, and peripheral nerves.

19. The method of claim 15, further comprising determining a distribution of at least one of a 2nd order mADC, a 4th order mADC, or a 6th order mADC.

20. The method of claim 4, wherein the MDDs are estimated based on a Laplace transformation of the obtained signal decays.

21. The method of claim 4, wherein the three-dimensional, refocusing balanced magnetic field gradient pulse sequences include a balanced, trapezoidal pulse sequence associated with at least one axis that is temporally symmetric as inverted.

22. The method of claim 4, wherein the three-dimensional, refocusing balanced magnetic field gradient pulse sequences include a balanced, trapezoidal pulse sequence that includes a first trapezoidal pulse having a first pulse area and a second trapezoidal pulse having a second pulse area applied prior to a refocusing pulse, wherein a ratio of the first pulse area to the second pulse area is less than 1:3.

23. The method of claim 4, wherein the three-dimensional, refocusing balanced magnetic field gradient pulse sequences include:
along a first axis and in temporal order, a balanced, trapezoidal pulse sequence that includes a first trapezoidal pulse having a first pulse area and a second trapezoidal pulse having a second pulse area applied prior to a refocusing pulse, wherein a ratio of the first pulse area to the second pulse area is about I:1, and a third trapezoidal pulse having the same pulse area and an opposite polarity as the second trapezoidal pulse and a fourth a trapezoidal pulse having the same pulse area and an opposite polarity as the first trapezoidal pulse.

24. The method of claim 4, wherein the three-dimensional, refocusing balanced magnetic field gradient pulse sequences include:
along a second axis and in temporal order, a balanced, trapezoidal pulse sequence that includes a first trapezoidal pulse having a pulse area and a second trapezoidal pulse having the pulse area applied prior to a refocusing pulse, and a third trapezoidal pulse having the pulse area and the same polarity as the second trapezoidal pulse and a fourth a trapezoidal pulse having the first pulse area and a polarity opposite to that of the first trapezoidal pulse.

25. The method of claim 24, wherein each of the trapezoidal pulses associated with the second axis has an equal pulse magnitude.

26. The method of claim 24, wherein each of the trapezoidal pulses associated with the second axis has an equal pulse duration.

27. The apparatus of claim 5, wherein the MRI processor is further configured to produce cumulative density functions based on the MDDs.

28. The method of claim 2, wherein the at least one distribution of mADCs associated with at least one of a $2^{nd}$, $4^{th}$, or $6^{th}$-order diffusion tensor is a cumulative distribution.

29. The method of claim 15, further comprising determining a cumulative distribution of at least one of a 2nd order mADC, a 4th order mADC, or a 6th order mADC.

* * * * *